US011667897B2

(12) United States Patent
Tian et al.

(10) Patent No.: US 11,667,897 B2
(45) Date of Patent: Jun. 6, 2023

(54) D-AMINO ACID OXIDATIVE ENZYME MUTANT AND APPLICATION THEREOF

(71) Applicant: SHANGHAI QIZHOU ZIYUE BIOTECHNOLOGY CO., LTD, Shanghai (CN)

(72) Inventors: Zhenhua Tian, Shanghai (CN); Zhanbing Cheng, Shanghai (CN); Yanbing Xu, Shanghai (CN)

(73) Assignee: SHANGHAI QIZHOU ZIYUE BIOTECHNOLOGY CO., LTD., Shanghai (CN)

( * ) Notice: Subject to any disclaimer, the term of this patent is extended or adjusted under 35 U.S.C. 154(b) by 41 days.

(21) Appl. No.: 17/295,676

(22) PCT Filed: Nov. 22, 2019

(86) PCT No.: PCT/CN2019/120249
§ 371 (c)(1),
(2) Date: May 20, 2021

(87) PCT Pub. No.: WO2020/013928
PCT Pub. Date: May 28, 2020

(65) Prior Publication Data
US 2022/0010342 A1 Jan. 13, 2022

(30) Foreign Application Priority Data
Nov. 23, 2018 (CN) .......................... 201811408085.1

(51) Int. Cl.
C12N 9/02 (2006.01)
C12P 9/00 (2006.01)
C12N 9/06 (2006.01)
C12N 15/00 (2006.01)

(52) U.S. Cl.
CPC ........... C12N 9/0024 (2013.01); C12N 15/00 (2013.01); C12P 9/00 (2013.01); *C12Y 104/03003* (2013.01)

(58) Field of Classification Search
CPC .................................. C12N 9/0024; C12P 9/00
See application file for complete search history.

(56) References Cited

U.S. PATENT DOCUMENTS

| | | | |
|---|---|---|---|
| 5,130,246 A | 7/1992 | Schulz et al. | |
| 5,221,737 A | 6/1993 | Bartsch et al. | |
| 6,936,444 B1 | 8/2005 | Bartsch | |
| 9,834,802 B2 | 12/2017 | Green et al. | |
| 10,081,812 B2* | 9/2018 | Ji ........................ | C12N 15/815 |
| 2008/0009052 A1 | 1/2008 | Wang et al. | |
| 2017/0253897 A1 | 9/2017 | Green et al. | |

FOREIGN PATENT DOCUMENTS

| | | |
|---|---|---|
| CN | 1680558 A | 10/2005 |
| CN | 1284858 C | 11/2006 |
| CN | 103103167 A | 5/2013 |
| CN | 106978453 A | 7/2017 |
| EP | 0344683 A | 12/1989 |

OTHER PUBLICATIONS

Studer. Residue mutations and their impact on protein structure and function: detecting beneficial and pathogenic changes. Biochem. J. (2013) 449, 581-594.*
Extended European Search Report issued in the counterpart European application No. 198873986 dated Jul. 29, 2022.
Tim Hawkes et al: "D-glufosinate as a male sterility agent for hybrid seed production", Plant Biotechnology Journal, vol. 9, No. 3, Apr. 1, 2011 (Apr. 1, 2011), pp. 301-314.
Wang et al., "Investigating Substrate Scope and Enantioselectivity of a Defluorinase by a Stereochemical Probe" J. Am. Chem. Soc., Aug. 16, 2017, 139(32), 11241-11247.

* cited by examiner

*Primary Examiner* — Yong D Pak
(74) *Attorney, Agent, or Firm* — Maschoff Brennan

(57) ABSTRACT

Provided is a D-amino acid oxidative enzyme mutant. The sequence of the mutant comprises a sequence by mutating the 54$^{th}$ amino acid residue N, the 58$^{th}$ amino acid residue F, the 211$^{th}$ amino acid residue C, and the 213$^{th}$ amino acid residue M of the sequence shown in SEQ ID NO:1 or the sequence having at least 76% identity with SEQ ID NO:1. The D-amino acid oxidative enzyme mutant has a higher enzyme activity, enzyme activity stability and/or ammonium resistance than a mild D-amino acid oxidative enzyme mutant. Also provided is an application of the D-amino acid oxidative enzyme mutant in preparing 2-oxo-4-(hydroxymethylphosphinyl)butyric acid.

13 Claims, No Drawings

Specification includes a Sequence Listing.

D-AMINO ACID OXIDATIVE ENZYME MUTANT AND APPLICATION THEREOF

The Sequence Listing is submitted concurrently with the specification as an ASCII formatted text file via EFS-Web, with a file name of "Your Ref. 36543, Our Ref [P21410166US].SEQ", a creation date of May 18, 2021, and a size of 245,275 bytes. The Sequence Listing filed via EFS-Web is part of the specification and is incorporated in its entirety by reference herein.

This application claims priority to Chinese patent application CN2018114080851, filed on Nov. 23, 2018, the contents of which are incorporated herein by its entirety.

TECHNICAL FIELD

The invention belongs to the field of biotechnology, and specifically relates to a D-amino acid oxidase mutant and a use thereof in preparing 2-oxo-4-(hydroxy(methyl)phosphinyl) butyric acid (PPO).

BACKGROUND

Glufosinate is a broad-spectrum contact herbicide developed by Hoechst in the 1980s. At present, the three major herbicides in the world are glyphosate, glufosinate and paraquat. Compared with glyphosate and paraquat, glufosinate has excellent herbicidal properties and fewer side effects. There are two optical isomers of glufosinate, namely D-glufosinate and L-glufosinate, but only L-glufosinate has herbicidal activity. Therefore, the method of developing L-glufosinate is important for improving atomic economy, reducing cost and reducing environmental pressure.

So far, L-glufosinate is mainly prepared by transaminase catalyzed 2-oxo-4-(hydroxy(methyl)phosphinyl) butyric acid (PPO). U.S. Pat. No. 5,221,737A and EP0344683A describe a method for obtaining L-glufosinate from the corresponding keto acid 4-(hydroxymethylphosphinyl)-2-oxobutyric acid by the action of an aminotransaminase derived from *Escherichia coli* using glutamic acid as amino donor. The reaction system requires an equivalent or excess amount of amino donor of glutamic acid, which makes it difficult to purify the product. CN1284858C improved the methods described above, in which L-glufosinate is obtained from the corresponding keto acid 4-(hydroxy(methyl)phosphinyl)-2-oxobutyric acid by the action of an aspartate aminotransferase using aspartic acid as amino donor. In this method, aspartic acid is converted to oxaloacetic acid, which is unstable in aqueous medium and can spontaneously decarboxylate to pyruvic acid; and pyruvic acid can be removed by an enzymatic reaction, making the reverse reaction impossible. Therefore, the reaction requires only equimolar amino donor and amino acceptor. However, the amino donors used in the method of using transaminase are mostly amino acids, resulting in a relatively high cost.

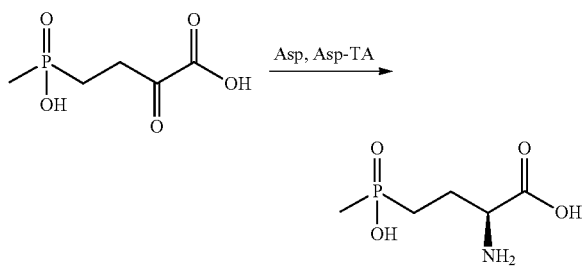

Besides, there is also a method for preparing L-glufosinate using 2-oxo-4-(hydroxy(methyl)phosphinyl) butyric acid (PPO) as substrate and catalyzing by amino acid dehydrogenase. For example, CN106978453A, which uses inorganic amino donors, making the separation of the product simple and reducing the cost.

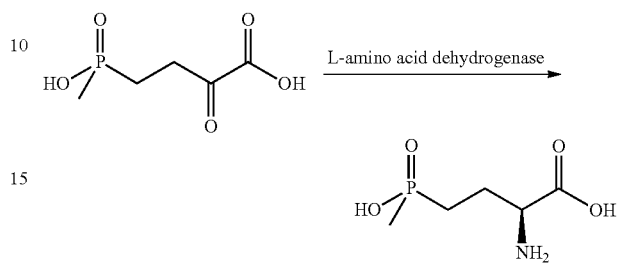

All of the methods described above use PPO as the raw material for the reaction, but the high cost of PPO leads to the expensiveness of producing L-glufosinate. While U.S. Pat. No. 9,834,802B discloses a method for preparing L-glufosinate by using D, L-glufosinate as a raw material. Firstly, D-amino acid oxidase (DAAO) oxidizes D-glufosinate to obtain PPO, and then PPO is catalyzed by transaminase to obtain L-glufosinate.

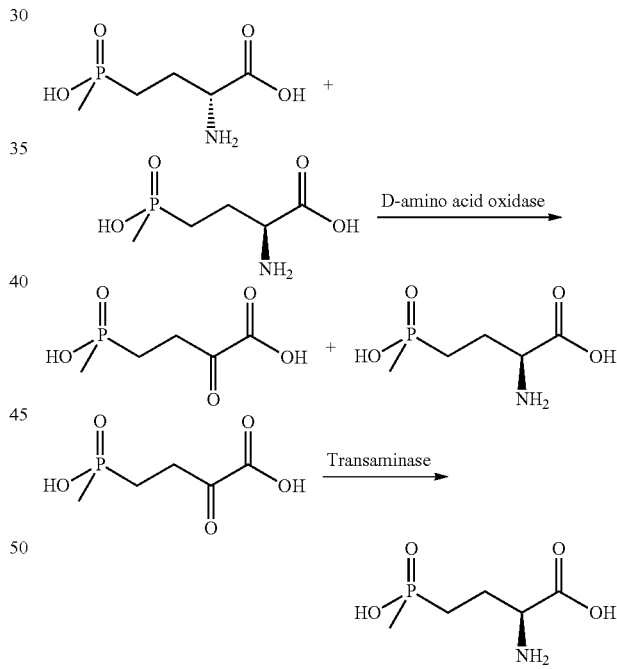

However, with D, L-glufosinate as raw materials, there is still a problem as follows: Strecker method is generally used to produce D, L-glufosinate in the market, which requires an excess of ammonium chloride. As a result, all the produced D, L-glufosinate are ammonium salts while there is an excess of ammonium chloride. The presence of ammonium ions has an inhibitory effect on the enzyme activity of DAAO, thereby reducing the enzyme activity. For example, the present inventors found that when the feed concentration of D, L-glufosinate ammonium salt was high, the high concentration of ammonium ion has a great inhibitory effect on the enzyme activity of the mutant with the best effect in U.S. Pat. No. 9,834,802B described above.

Therefore, there is an urgent need to find a DAAO that is not inhibited by ammonium ions, which has higher stability of enzyme activity and can tolerate a higher feed concentration of D, L-glufosinate ammonium salt.

Content of the Present Invention

The technical problem to be solved by the present invention is to overcome the disadvantages of low enzyme activity, poor stability of enzyme activity or poor ammonium tolerance of D-amino acid oxidase in the prior art. The present invention provides a D-amino acid oxidase mutant and a use thereof in preparing 2-oxo-4-(hydroxy(methyl)phosphinyl) butyric acid. The D-amino acid oxidase mutant of the present invention has high enzymatic activity, improved stability of enzyme activity and/or enhanced ammonium tolerance, thereby reducing costs and benefiting industrial production.

The inventors found that high concentrations of ammonium ions have a great inhibitory effect on enzyme activity at the early stage of the experiment. Mutants with mutations at positions 54, 58 and 213 of the DAAO amino acid sequence in the prior art were screened, and ammonium ion was found to have the weakest inhibitory effect on the $N_2DAAO$ sequence with 76% identity, so the $N_2DAAO$ sequence was selected for further mutation. After extensive screenings, the inventors found that when a mutation at position C211 was introduced, the enzyme activity of the resulting mutant was increased under the action of ammonium ions, and then combined mutations at positions including C211 were proceeded to construct a mutant library, from which the D-amino acid oxidase mutants described in the present invention were screened. Subsequently, the inventors proceeded the same combined mutation at positions including C211 on other DAAO amino acid sequences in the prior art, and it was surprisingly found that the resulting mutants did have improved ammonium ions tolerance, thus verifying that position C211 site has a great impact on the ammonium tolerance of different D-amino acid oxidase, and the mutations at position C211 together with positions 54, 58 and 213 can remarkably improve the enzyme activity and stability of D-amino acid oxidase in the presence of ammonium ions.

In order to solve the technique problem described above, the present invention aims to provide a D-amino acid oxidase mutant having a sequence comprising mutations of amino acid residue N at position 54, amino acid residue F at position 58, amino acid residue C at position 211 and amino acid residue M at position 213 on SEQ ID NO: 1 or on a sequence having at least 76% identity with SEQ ID NO: 1; the D-amino acid oxidase mutant has higher enzyme activity, stability of enzyme activity and/or ammonium tolerance than wild-type D-amino acid oxidase. The at least 76% identity is preferably at least 80% identity, at least 85% identity, at least 90% identity, at least 95% identity, at least 96% identity, at least 97% identity, at least 98% identity or at least 99% identity.

The ammonium tolerance of the present invention refers to the enhanced tolerance of the mutants of the present invention to ammonium ions in the reaction process, and the enhanced tolerance is mainly reflected in the fact that the mutants of the present invention remain stable when concentration of ammonium ion is high (i.e., the loss of enzyme activity is small), and the enzyme activity is still high.

Preferably, the sequence having at least 76% identity with SEQ ID NO: 1 is shown in SEQ ID NO: 3.

Preferably, the D-amino acid oxidase mutant comprises the following mutations on the sequence of SEQ ID NO:1: mutation of amino acid residue N at position 54 to A, C, G, S, T or V; and/or, mutation of amino acid residue F at position 58 to a hydrophilic amino acid residue or amino acid residue with small steric hindrance; and/or, mutation of amino acid residue C at position 211 to A, D, G, H, L, M, S or Y; and/or, mutation of amino acid residue M at position 213 to A, C, F, L, R, S, T, V or W.

According to the present invention, the hydrophilicity or small steric hindrance refers to that the amino acid residues after mutation are more hydrophilic or have less steric hindrance than the amino acid residues in wild sequence. The amino acids can be modified or unmodified natural amino acids; the present invention takes natural amino acids as an example.

Preferably, the amino acid residue N at position 54 is mutated to V, the amino acid residue F at position 58 is mutated to Q, the amino acid residue C at position 211 is mutated to A, D, G, H, L, M, S or Y, and the amino acid residue M at position 213 is mutated to A, C, F, L, R, S, T, V or W; more preferably, the amino acid residue C at position 211 is mutated to A, G, M, S, Y or L, and/or the amino acid residue M at position 213 is mutated to F, L, R, T or W; even more preferably, the amino acid residue C at position 211 is mutated to L or M, and/or the amino acid residue M at position 213 is mutated to T.

Preferably, wherein the amino acid residue C at position 211 is mutated to L, the amino acid residue M at position 213 is mutated to T, the amino acid residue N at position 54 is mutated to A, C, G, S, T or V, and the amino acid residue F at position 58 is mutated to A, G, H, K or Q; more preferably, the amino acid residue N at position 54 is mutated to A, G, S or T, and/or the amino acid residue F at position 58 is mutated to H, K or Q; even more preferably, the amino acid residue N at position 54 is mutated to A, and/or the amino acid residue F at position 58 is mutated to H or K; even more preferably, the sequence of the D-amino acid oxidase mutant further comprises mutation of amino acid residue T at position 56 of SEQ ID NO: 1 to N, S or L, the amino acid residue T at position 56 is preferably mutated to N.

The capital English single letters mentioned above represent amino acids as well known to those skilled in the art. According to the present invention, the capital English single letters represent corresponding amino acid residues herein.

Preferably, the D-amino acid oxidase mutant has an amino acid sequence of SEQ ID NO.5, SEQ ID NO.7, SEQ ID NO.9, SEQ ID NO.11, SEQ ID NO.13, SEQ ID NO.15, SEQ ID NO.17, SEQ ID NO.19, SEQ ID NO.21, SEQ ID NO.23, SEQ ID NO.25, SEQ ID NO.27, SEQ ID NO.29, SEQ ID NO.31, SEQ ID NO.33, SEQ ID NO.35, SEQ ID NO.37 SEQ ID NO.39, SEQ ID NO.41, SEQ ID NO.43, SEQ ID NO.45, SEQ ID NO.47, SEQ ID NO.49, SEQ ID NO.51, SEQ ID NO.53, SEQ ID NO.55, SEQ ID NO.57, SEQ ID NO.59, SEQ ID NO.61, SEQ ID NO.63, SEQ ID NO.65, SEQ ID NO.68, SEQ ID NO.70, SEQ ID NO.72, SEQ ID NO.75, SEQ ID NO.79, SEQ ID NO.82, SEQ ID NO.90, SEQ ID NO.100 or SEQ ID NO.102.

Preferably, the D-amino acid oxidase mutant is encoded by a nucleotide sequence of SEQ ID NO.6, SEQ ID NO.8, SEQ ID NO.10, SEQ ID NO.12, SEQ ID NO.14, SEQ ID NO.16, SEQ ID NO.18, SEQ ID NO.20, SEQ ID NO.22, SEQ ID NO.24, SEQ ID NO.26, SEQ ID NO.28, SEQ ID NO.30, SEQ ID NO.32, SEQ ID NO.34, SEQ ID NO.36, SEQ ID NO.38, SEQ ID NO.40, SEQ ID NO.42, SEQ ID NO.44, SEQ ID NO.46, SEQ ID NO.48, SEQ ID NO.50, SEQ ID NO.52, SEQ ID NO.54, SEQ ID NO.56, SEQ ID NO.58, SEQ ID NO.60, SEQ ID NO.62, SEQ ID NO.64, SEQ ID NO.66, SEQ ID NO.67, SEQ ID NO.69, SEQ ID NO.71, SEQ ID NO.73, SEQ ID NO.74, SEQ ID NO.76, SEQ ID NO.77, SEQ ID NO.78, SEQ ID NO.80, SEQ ID NO.81, SEQ ID NO.83, SEQ ID NO.84, SEQ ID NO.85, SEQ ID NO.86, SEQ ID NO.87, SEQ ID NO.88, SEQ ID NO.89, SEQ ID NO.91, SEQ ID NO.101 or SEQ ID NO.103.

In order to solve the technique problem described above, the present invention aims to provide an isolated nucleic acid, wherein the nucleic acid encodes the D-amino acid oxidase mutant defined above.

In order to solve the technique problem described above, the present invention aims to provide a recombinant expression vector comprising the nucleic acid defined above.

In order to solve the technique problem described above, the present invention aims to provide a transformant comprising the nucleic acid defined above or the recombinant expression vector defined above.

In order to solve the technique problem described above, the present invention aims to provide a use of the D-amino acid oxidase mutant defined above in preparing 2-oxo-4-(hydroxy(methyl)phosphinyl) butyric acid.

The enzyme activity of the present invention includes the properties of specific enzyme activity and enzyme activity.

On the basis of conforming to common knowledge in the field, the preferred conditions defined above can be combined arbitrarily to obtain preferred embodiments of the present invention.

The reagents and raw materials used in the present invention are all commercially available.

The positive and progressive effects of the present invention are: the D-amino acid oxidase mutant of the present invention has high enzyme activity, improved stability of enzyme activity and/or enhanced ammonium tolerance, thereby reducing costs and facilitating industrial production.

DETAILED DESCRIPTION OF THE PREFERRED EMBODIMENT

The present invention is further illustrated by the following examples, but is not thereby limited to the scope described hereto. The experimental methods for which specific conditions are not indicated in the following examples are usually selected in accordance with the conventional methods and conditions, or in accordance with the instruction of commodity.

The experimental methods in the present invention are conventional methods unless otherwise specified, and specific gene cloning operations can refer to "Molecular Cloning: A Laboratory Manual" edited by J. Sambrook et al.

The abbreviations of amino acids in the present invention are conventional in the art unless otherwise specified, and the amino acids corresponding to the specific abbreviations are shown in Table 1.

TABLE 1

| Name of amino acid | Three-letter symbol | One-letter symbol |
|---|---|---|
| alanine | Ala | A |
| arginine | Arg | R |
| asparagine | Asn | N |
| aspartic acid | Asp | D |
| cysteine | Cys | C |
| glutamine | Gln | Q |
| glutamic acid | Glu | E |
| Glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophan | Trp | W |
| tyrosine | Tyr | Y |
| valine | Val | V |

The codons corresponding to the amino acids are also conventional in the art, and the correspondence between specific amino acids and codons is shown in Table 2.

TABLE 2

| The first nucleotide | The second nucleotide | | | | The Third nucleotide |
|---|---|---|---|---|---|
| | T | C | A | G | |
| T | phenylalanine F | serine S | tyrosine Y | cysteine C | T |
| | phenylalanine F | serine S | tyrosine Y | cysteine C | C |
| | leucine L | serine S | termination codon | termination codon | A |
| | leucine L | serine S | termination codon | tryptophan W | G |
| C | leucine L | proline P | histidine H | arginine R | T |
| | leucine L | proline P | histidine H | arginine R | C |
| | leucine L | proline P | glutamine Q | arginine R | A |
| | leucine L | proline P | glutamine Q | arginine R | G |
| A | isoleucine I | threonine T | asparagine N | serine S | T |
| | isoleucine I | threonine T | asparagine N | serine S | C |
| | isoleucine I | threonine T | lysine K | arginine R | A |
| | methionine M | threonine T | lysine K | arginine R | G |
| G | valine V | alanine A | aspartic acid D | glycine G | T |
| | valine V | alanine A | aspartic acid D | glycine G | C |
| | valine V | alanine A | glutamic acid E | glycine G | A |
| | valine V | alanine A | glutamic acid E | glycine G | G |

Pet28a and bugbuster protein extraction reagent were purchased from Novagen; NdeI enzyme and HindIII enzyme were purchased from Thermo Fisher, BL21 competent cells were purchased from Beijing Dingguo Changsheng Biotechnology Co., Ltd.; catalase was purchased from Shandong Fengtai Biotechnology Co., Ltd.

Example 1 Preparation of Wild-Type D-Amino Acid Oxidase (DAAO)

Wild-type (wt) $N_2$DAAO enzyme gene (with GenBank accession number KWU45700, from *Rhodotorula* sp. JG-1b) was fully synthesized by Suzhou GENEWIZ Biotechnology Co., Ltd. (Bio-Nano Technology Park Building B1 and C3, 218 Xinghu Road, Suzhou Industrial Park, Suzhou).

Synthesized DAAO gene was ligated to pET28a (see J. Am. Chem. Soc., 2017, 139(32), 11241-11247 for specific methods), at restriction sites NdeI & HindIII, and the ligated vector was transformed into host *E. coli* BL21 (DE3) competent cells. The cells were inoculated in LB liquid medium and incubated in a shaker at 200 rpm, 37° C. When the $OD_{600}$ reached about 0.8, the cells broth was added with sterile glycerin at a final concentration of 25%, numbered and stored in a low-temperature refrigerator at −80° C. for later use.

The composition of LB liquid medium is as follows: peptone 10 g/L, yeast powder 5 g/L, NaCl 10 g/L, dissolved with deionized water and diluted to a final volume, sterilized at 121° C. for 20 minutes for later use.

After resuscitating the engineered strain containing the enzyme gene which was store in a low-temperature refrigerator at −80° C. described above by streaking on a plate, a single colony was inoculated into 5 ml of LB liquid medium containing 50 μg/ml kanamycin, and incubated at 37° C. for 12 h with shaking. 2% of inoculum was transferred to 150 ml of fresh LB liquid medium containing 50 μg/ml kanamycin, then incubated at 37° C. with shaking until the $OD_{600}$ value reached about 0.8, followed by cooling to 30° C. IPTG was added to a final concentration of 0.5 mM for induced culturing for 16 h. After cultivation, the culture solution was centrifuged at 10,000 rpm for 10 min, the supernatant was discarded, and the cells were collected and stored in an ultra-low temperature refrigerator at −20° C. for later use.

After culturing, the cells were collected and washed twice with 50 mM phosphate buffer solution with pH 8.0, and then resuspended in phosphate buffer solution, pH 8.0, followed by lysing homogeneously. The lysis liquid was centrifuged to remove cell debris, thus obtaining a crude enzyme solution containing recombinant wt$N_2$DAAO.

Example 2 Construction of D-Amino Acid Oxidase (DAAO) Mutant Library (Position 211, 213)

After mutating positions 54 and 58 (specifically N54V, F58Q) on the wt$N_2$DAAO sequence described in Example 1, a mutated D-amino acid oxidase sequence was obtained, and gene $N_2$DAAO (N54V, F58Q) was synthesized according to the sequence by Suzhou GENEWIZ Biotechnology Co., Ltd. (Bio-Nano Technology Park Building B1 and C3, 218 Xinghu Road, Suzhou Industrial Park, Suzhou). Then the gene was ligated to plasmid pET28a at restriction sites NdeI and HindIII to construct plasmid pET28a-$N_2$DAAO (see J. Am. Chem. Soc., 2017, 139(32), 11241-11247 for the plasmid construction method). The target band was amplified by PCR using plasmid pET28a-N2DAAO as template.

Wherein, PCR primer sequences were designed for the construction of mutant libraries with mutations at positions 211 and 213 of the mutated D-amino acid oxidase sequence (N54V, F58Q), as shown in Table 3:

TABLE 3

| No. | Mutation position and primer name | Primer sequence | SEQ ID NO: |
|---|---|---|---|
| 1 | 211-213 forward primer | AGCAACTGTAAACGCNNKAC CNNKGACAGTAGTGACCCG | 104 |
| 2 | 211-213 reverse primer | CGGGTCACTACTGTCMNNGG TMNNGCGTTTACAGTTGCT | 105 |

Wherein, N represents any of the nucleotides A, G, C and T, M represents A or C, and K represents G or T; it is selected according to the nucleotide encoding the amino acid to which the site needs to be mutated. For example, NNK in the A166-forward primer can represent AAG (lysine), AAT (aspartic acid), AGG (arginine) or AGT (serine), etc. The nucleotides corresponding to specific amino acids can be found in Table 2.

PCR amplification system is as follows:

| Reagent | Volume (μL) |
|---|---|
| 2 × PCR buffer (Contains high-fidelity enzyme) | 25 |
| forward primer | 1 |
| reverse primer | 1 |
| template | 1 |
| deionized water | 22 |

PCR amplification procedure is as follows:

| | | |
|---|---|---|
| 95° C. | 5 min | |
| 95° C. | 30 s | |
| 50° C. | 30 s | } 30 cycles |
| 72° C. | 5 min | |
| 72° C. | 10 min | |
| 12° C. | ∞ | |

PCR products were digested with DpnI at 37° C. for 2 h. After that, the digested product was transformed into BL21 competent cells, which were then spread on LB medium containing 50 μg/mL kanamycin, and incubated overnight at 37° C. Cells were harvested and transformants containing the mutant library were obtained.

Example 3 High-Throughput Screening of Mutant Libraries

Screening was performed according to the following experimental steps:

The transformants obtained in Example 2 were inoculated and incubated in 96-wells plate, inducing with IPTG at 30° C. overnight. The cells were then harvested, and lysed by bugbuster protein extraction reagent, thus obtaining the enzyme solution by centrifugation.

Detection method of microplate reader is as follows: 100 μL of 100 mM substrate (racemic glufosinate, purchased from Shanghai Aladdin Biochemical Technology Co., Ltd.) with a pH of 8.0 was added with 50 μL of chromogenic substrate solution (containing 60 mg/mL TBHBA (3-hydroxy-2,4,6-tribromobenzoic acid), 100 mg/mL 4-AAP (4-aminoantipyrine) and 25 μL HRP (horseradish peroxidase, 0.1 mg/mL), and finally added with 25 μL of the DAAO mutant enzyme solution described above, to obtain a 200 μL microplate reaction system. It was analyzed at 30° C., pH 8.0. The absorbance at 510 nm at 0 min and 20 min was recorded respectively, and the difference between the two absorbance values was taken to screen positive clones using wild type as a reference.

The selected positive clones were cultured as follows:

The composition of LB liquid medium is as follows: 10 g/L of peptone, 5 g/L of yeast powder and 10 g/L of NaCl were dissolved in deionized water and diluted to a final volume, and sterilized at 121° C. for 20 minutes for later use.

A single colony was inoculated into 5 ml LB liquid medium containing 50 μg/ml kanamycin, and incubated at 37° C. for 12 h with shaking. 2% of inoculum was transferred to 150 ml fresh LB liquid medium containing 50 μg/ml kanamycin and incubated at 37° C. with shaking until OD$_{600}$ value reached about 0.8. IPTG was added to a final concentration of 0.5 mM for induced culturing at 30° C. for 16 h. After cultivation, the culture solution was centrifuged at 10,000 rpm for 10 min, the supernatant was discarded, and the cells were collected and stored in an ultra-low temperature refrigerator at −20° C. for later use.

The collected cells were washed twice with 50 mM phosphate buffer solution, pH 8.0, and then resuspended in phosphate buffer solution, pH 8.0, followed by lysing homogeneously at low temperature and high pressure. The lysis liquid was centrifuged to remove cell debris, thus obtaining a crude enzyme solution containing recombinant DAAO mutant.

Detection method of enzyme activity for mutant re-screening is as follows:

1 mL of 500 mM D, L-Glufosinate ammonium salt, 0.25 mL of the preliminary crude enzyme solution containing recombinant DAAO mutant described above, 1.25 mL of horseradish peroxidase (HRP), and 2.5 mL of chromogenic substrate solution (containing 60 mg/mL TBHBA and 100 mg/mL 4-AAP) were added to form a 5 mL reaction system, with disodium hydrogen phosphate-sodium dihydrogen phosphate buffer, pH 8.0, as the reaction medium. The reaction was performed in a shaker at 30° C. Every 2 minutes, the reaction solution was scanned at 510 nm for absorbance value, and the kinetic curve of the enzyme reaction was plotted for absorbance and time (min), thus calculating the enzyme activity according to the slope of the curve. The results are shown in Table 4.

Definition of unit enzyme activity: under specific reaction conditions (30° C.), the amount of enzyme required to generate 1 μmol H$_2$O$_2$ per minute, wherein the unit of enzyme activity is U.

Specific enzyme activity is the number of activity unit per milligram of enzyme protein, which is equal to enzyme activity/protein content, and the unit is U/mg or U/g.

TABLE 4

| Number of enzymes | Mutation position | Specific enzyme activity (U/mg) | Amino acid SEQ ID NO: | Nucleotide SEQ ID NO: |
|---|---|---|---|---|
| 1 | wt(N$_2$DAAO) | * | 1 | 2 |
| 2 | N$_2$DAAO(N54V-F58Q-M213S) | ** | 5 | 6 |
| 3 | N54V-F58Q-C211S-M213T | ** | 7 | 8 |
| 4 | N54V-F58Q-C211A-M213T | *** | 9 | 10 |
| 5 | N54V-F58Q-C211G-M213F | *** | 11 | 12 |
| 6 | N54V-F58Q-C211M-M213R | *** | 13 | 14 |
| 7 | N54V-F58Q-C211G-M213T | *** | 15 | 16 |
| 8 | N54V-F58Q-C211A-M213R | ** | 17 | 18 |
| 9 | N54V-F58Q-C211G-M213S | *** | 19 | 20 |
| 10 | N54V-F58Q-C211D-M213V | *** | 21 | 22 |
| 11 | N54V-F58Q-C211L-M213T | **** | 23 | 24 |
| 12 | N54V-F58Q-C211A-M213C | ** | 25 | 26 |
| 13 | N54V-F58Q-C211A-M213L | ** | 27 | 28 |
| 14 | N54V-F58Q-C211G-M213L | ** | 29 | 30 |
| 15 | N54V-F58Q-C211M-M213S | *** | 31 | 32 |
| 16 | N54V-F58Q-C211A-M213S | *** | 33 | 34 |
| 17 | N54V-F58Q-C211H-M213L | *** | 35 | 36 |
| 18 | N54V-F58Q-C211S-M213C | *** | 37 | 38 |
| 19 | N54V-F58Q-C211M-M213L | *** | 39 | 40 |
| 20 | N54V-F58Q-C211S-M213L | *** | 41 | 42 |
| 21 | N54V-F58Q-C211Y-M213F | *** | 43 | 44 |
| 22 | N54V-F58Q-C211S-M213V | *** | 45 | 46 |
| 23 | N54V-F58Q-C211M-M213T | *** | 47 | 48 |
| 24 | N54V-F58Q-C211G-M213W | *** | 49 | 50 |
| 25 | N54V-F58Q-C211A-M213A | *** | 51 | 52 |
| 26 | N54V-F58Q-C211A-M213V | *** | 53 | 54 |

Note:
in the above Table, * represents specific enzyme activity between 0-0.10 U/mg,  represents specific enzyme activity between 0.1-1.0 U/mg, * represents specific enzyme activity between 1.0-20 U/mg, **** represents specific enzyme activity between 20-50 U/mg.

It can be seen from Table 4 that the specific enzyme activities of the obtained mutants were all higher than that of wild-type N$_2$DAAO. Among them, the DAAO oxidase mutant 11 has the highest specific enzyme activity, which has such mutation: N at position 54 was mutated to V, F at position 58 was mutated to Q, C at position 211 was mutated to L and M at position 213 was mutated to T.

Example 4 Construction of a Mutant Library for Mutations at Positions 54, 56 and 58 of DAAO Oxidase Mutant 11 in Example 3

The primer sequences designed for the construction of mutant library with mutations at positions 54, 56 and 58 of DAAO oxidase mutant 11 are shown in Table 5.

TABLE 5

| No. | Mutation positions and name of primers | Primer sequences | SEQ ID NO: |
|---|---|---|---|
| 1 | 54-56-58 forward primer | CCCTTGGGCCGGTGCNNKTTGNN KCCCNNKGATGAGCAAAGAAGC | 106 |
| 2 | 54-56-58 reverse primer | GCTTCTTTGCTCATCMNNGGGMN NCAAMNNGCACCGGCCCAAGGG | 107 |

Wherein, N represents any of nucleotide A, G, C and T, M represents A or C, and K represents G or T; it is selected according to the nucleotide encoding the amino acid to which the site needs to be mutated. For example, NNK in the A166-forward primer can represent AAG (lysine), AAT (aspartic acid), AGG (arginine) or AGT (serine), etc. The nucleotides corresponding to specific amino acids can be found in Table 2.

The plasmid template pET28a-DAAO oxidase mutant 12 was constructed according to the method disclosed in J. Am. Chem. Soc, 2017, 139(32), 11241-11247. The target band was amplified by PCR using plasmid pET28a-DAAO oxidase mutant 11 as template.

The amplification reaction system is as follows:

| Reagent | Volume (µL) |
|---|---|
| 2 × PCR buffer (Contains high-fidelity enzyme) | 25 |
| forward primer | 1 |
| reverse primer | 1 |
| template | 1 |
| deionized water | 22 |

The amplification procedure is as follows:

| | | |
|---|---|---|
| 95° C. | 5 min | |
| 95° C. | 30 s | |
| 50° C. | 30 s | 30 cycles |
| 72° C. | 5 min | |
| 72° C. | 10 min | |
| 12° C. | ∞ | |

PCR products were digested with DpnI at 37° C. for 2 h. After the reaction, the digested product was transformed into BL21 competent cells, which was then spread on LB medium containing 50 µg/mL kanamycin. After incubating overnight at 37° C., the cells were harvested, and transformants containing the mutant library were obtained.

Example 5 Detections of the Stability of Enzyme Activity and the Influence of $NH_4^+$ Ion Concentration The transformants obtained in Example 4 was inoculated and incubated in a 96-well plate, inducing by IPTG at 30° C. overnight. After completing the induction, the cells were harvested and lysed with bugbuster protein extraction reagent, and centrifuged to obtain enzyme solution of the mutants.

The enzyme solution of the mutants was treated at 50° C. for 2 h. According to the detection method of microplate reader described in Example 3, the thermostability effect of the mutations of the positive clones was analyzed for screening of the positive clones.

Selected positive clones were cultured as follows:

The composition of LB liquid medium is as follows: 10 g/L of peptone, 5 g/L of yeast powder and 10 g/L of NaCl were dissolved in deionized water and diluted to a final volume, and sterilized at 121° C. for 20 minutes for later use.

A single colony was picked and inoculated into 5 ml LB liquid medium containing 50 µg/ml kanamycin, and incubated with shaking at 37° C. for 12 h. 2% of inoculum was transferred to 150 ml fresh LB liquid medium containing 50 µg/ml kanamycin and incubated with shaking at 37° C. until $OD_{600}$ value reached about 0.8. IPTG was added to a final concentration of 0.5 mM for induced culturing at 30° C. for 16 h. After cultivation, the culture solution was centrifuged at 10,000 rpm for 10 min, the supernatant was discarded, and the cells were collected and stored in an ultra-low temperature refrigerator at −20° C. for later use.

After cultivation, cells were collected and washed twice with 50 mM phosphate buffer solution, pH 8.0, and then resuspended in phosphate buffer solution, pH 8.0, followed by lysing homogeneously at low temperature and high pressure. The lysis liquid was centrifuged to remove cell debris, thus obtaining a crude enzyme solution containing recombinant DAAO mutant.

The enzyme activity of the obtained crude enzyme solution containing DAAO mutant was detected for mutant re-screening by the same method described in Example 3. The results obtained are shown in Table 6, wherein the % value of remaining enzyme activity after 2 h reflects the stability of the mutant enzyme activity.

TABLE 6

| No. of enzyme | Mutation position | Enzyme activity (U/ml) | % value of remaining enzyme activity after 2 h | Amino acid SEQ ID NO: | Nucleotide SEQ ID NO: |
|---|---|---|---|---|---|
| 1 | WT(N₂DAAO) | * | # | 1 | 2 |
| 11 | N54V- T56T- F58Q- C211L-M213T | *** | # | 23 | 24 |
| 27 | N54C- T56T- F58G- C211L-M213T | *** | # | 55 | 56 |
| 28 | N54S- T56T- F58H- C211L-M213T | *** | ## | 57 | 58 |
| 29 | N54G- T56T- F58K- C211L-M213T | *** | ### | 59 | 60 |
| 30 | N54A- T56T- F58H- C211L-M213T | *** | ### | 61 | 62 |
| 31 | N54A- T56T- F58K- C211L-M213T | ** | ### | 63 | 64 |
| 32 | N54C- T56T- F58A- C211L-M213T | *** | # | 65 | 66 |

TABLE 6-continued

| No. of enzyme | Mutation position | Enzyme activity (U/ml) | % value of remaining enzyme activity after 2 h | Amino acid SEQ ID NO: | Nucleotide SEQ ID NO: |
|---|---|---|---|---|---|
| 33 | N54A- T56T- F58H- C211L-M213T | ** | ### | 61 | 67 |
| 34 | N54G- T56T- F58A- C211L-M213T | * | # | 68 | 69 |
| 35 | N54V- T56T- F58H- C211L-M213T | *** | # | 70 | 71 |
| 36 | N54T- T56T- F58Q- C211L-M213T | **** | ### | 72 | 73 |
| 37 | N54A- T56T- F58H- C211L-M213T | ** | ### | 61 | 74 |
| 38 | N54A- T56T- F58Q- C211L-M213T | ** | ## | 75 | 76 |
| 39 | N54A- T56T- F58K- C211L-M213T | ** | ### | 63 | 77 |
| 40 | N54A- T56T- F58K- C211L-M213T | ** | ### | 63 | 78 |
| 41 | N54A- T56N- F58H- C211L-M213T | **** | ## | 79 | 80 |
| 42 | N54A- T56N- F58H- C211L-M213T | **** | ### | 79 | 81 |
| 43 | N54A- T56S- F58H- C211L-M213T | **** | ### | 82 | 83 |
| 44 | N54A- T56S- F58H- C211L-M213T | **** | # | 82 | 84 |
| 45 | N54A- T56S- F58H- C211L-M213T | **** | ### | 82 | 85 |
| 46 | N54A- T56T- F58H- C211L-M213T | **** | ### | 61 | 86 |
| 47 | N54A- T56T- F58H- C211L-M213T | *** | ## | 61 | 87 |
| 48 | N54A- T56S- F58H- C211L-M213T | *** | ## | 82 | 88 |
| 49 | N54A- T56N- F58H- C211L-M213T | **** | ### | 79 | 89 |
| 50 | N54A- T56L- F58H- C211L-M213T | **** | ## | 90 | 91 |

Note:
In the column of enzyme activity in the above Table, * represents the enzyme activity between 0-0.10 U/mg,  represents the specific enzyme activity between 0.1-2.0 U/mg, * represents the specific enzyme activity between 2.0-3.5 U/mg, and **** represents the specific enzyme activity between 3.5-10 U/mg.
In the column of remaining enzyme activity after 2 h, # represents the remaining enzyme activity after 2 h is between 0-50%, ## represents the remaining enzyme activity after 2 h is between 50-80%, ### represents the remaining enzyme activity after 2 h is between 80-100%.

Some mutants in the above Table (such as mutants 39 and 40, mutants 43-45, etc.) have the same amino acid sequence, but different DNA sequence, since their codons are not the same. The relevant amino acid sequences and DNA sequences are listed in the Sequence Listing.

The results showed that all the above mutants except mutant 34 have higher enzyme activity and stability of enzyme activity than those of the wild type. Wherein, the enzyme activity of mutant 36, mutant 41, mutant 42, mutant 43, mutant 45, mutant 46, mutant 49 and mutant 50 is much greater than that of mutant 11, and the stability of enzyme activity improved a lot. In addition, it can be seen from the Table that although the mutants described above have the same amino acid sequence, their ammonium ions tolerance is different due to different nucleotide sequences.

Then the mutants obtained above were tested for the influence of $NH_4^+$ ion concentration as follows:

$NH_4Cl$ with a final concentration of 2 M was added into the 200 μL microplate reaction system in the detection method of microplate reader described in Example 3, and the enzyme activity before and after the addition of $NH_4Cl$ was analyzed to determine the influence of the $NH_4Cl$ concentration on the enzyme activity. The obtained enzyme activity data are shown in Table 7:

TABLE 7

| No. of enzyme | Mutation position | Ratio of remaining enzyme activity after adding 2M $NH_4Cl$ | Amino acid SEQ ID NO: | Nucleotide SEQ ID NO: |
|---|---|---|---|---|
| 1 | WT($N_2$DAAO) | + | 1 | 2 |
| 27 | 54C-56T-58G-C211L-M213T | +++ | 55 | 56 |
| 28 | 54S-56T-58H-C211L-M213T | +++ | 57 | 58 |
| 29 | 54G-56T-58K-C211L-M213T | ++ | 59 | 60 |
| 30 | 54A-56T-58H-C211L-M213T | + | 61 | 62 |
| 31 | 54A-56T-58K-C211L-M213T | ++++ | 63 | 64 |

TABLE 7-continued

| No. of enzyme | Mutation position | Ratio of remaining enzyme activity after adding 2M NH₄Cl | Amino acid SEQ ID NO: | Nucleotide SEQ ID NO: |
|---|---|---|---|---|
| 32 | 54C-56T-58A-C211L-M213T | ++ | 65 | 66 |
| 33 | 54A-56T-58H-C211L-M213T | + | 61 | 67 |
| 35 | 54V-56T-58H-C211L-M213T | + | 70 | 71 |
| 36 | 54T-56T-58Q-C211L-M213T | +++ | 72 | 73 |
| 37 | 54A-56T-58H-C211L-M213T | + | 61 | 74 |
| 39 | 54A-56T-58K-C211L-M213T | ++++ | 63 | 77 |
| 40 | 54A-56T-58K-C211L-M213T | ++++ | 63 | 78 |
| 41 | 54A-56N-58H-C211L-M213T | +++ | 79 | 80 |
| 42 | 54A-56N-58H-C211L-M213T | ++++ | 79 | 81 |
| 43 | 54A-56S-58H-C211L-M213T | +++ | 82 | 83 |
| 44 | 54A-56S-58H-C211L-M213T | ++++ | 82 | 84 |
| 45 | 54A-56S-58H-C211L-M213T | +++ | 82 | 85 |
| 46 | 54A-56T-58H-C211L-M213T | ++ | 61 | 86 |
| 47 | 54A-56T-58H-C211L-M213T | ++ | 61 | 87 |
| 48 | 54A-56S-58H-C211L-M213T | ++ | 82 | 88 |
| 49 | 54A-56N-58H-C211L-M213T | ++++ | 79 | 89 |
| 50 | 54A-56L-58H-C211L-M213T | ++ | 90 | 91 |

Note:
In the above table, + represents the ratio of remaining enzyme activity between 0-0.30, ++ represents the ratio of remaining enzyme activity between 0.3-0.5, +++ represents the ratio of remaining enzyme activity between 0.5-0.6, and ++++ represents the ratio of remaining enzyme activity between 0.6-1.

The above results show that the above mutants have higher ammonium ions tolerance than the wild type. Among them, the enzyme activity, the stability of enzyme activity, and the ammonium ions tolerance of mutant 42 and mutant 49 were greatly improved compared with mutant 11. In addition, it can be seen from the Table that although the mutants described above have the same amino acid sequence, their ammonium ions tolerance is different due to different nucleotide sequences.

Example 6 Enzyme Activity of Other DAAO Enzymes with Combined Mutations at Positions 211 and 213

The rtDAAO enzyme from *Rhodosporidium toruloides* UniProtKB/Swiss-Prot P80324 has 76% identity to the sequence of GenBank accession number KWU45700 (SEQ ID NO: 1), and the sequence of which is shown in SEQ ID NO:3. After mutating positions 54, 58 and 213 (specifically N54V, F58Q, M213 S) on the basis of this sequence, a mutated D-amino acid oxidase sequences was obtained, and the gene rtDAAO (N54V-F58Q-M213S) was synthesized according to this sequence. Gene was synthesized by the same company described above. Point mutation was performed in this rtDAAO (N54V-F58Q-M213S) enzyme, wherein position 54 was mutated to A, position 56 was mutated to N, position 58 was mutated to H, position 211 was mutated to L, and position 213 was mutated to T, thus obtaining mutants shown in Table 8. These obtained mutants were subjected to detection of enzyme activity for mutant re-screening, and the method was the same as that in Example 3. The calculated enzyme activity and specific enzyme activity data are shown in Table 8.

The ammonium tolerance of the mutants was tested using the 200 μL microplate reaction system according to the detection method of microplate reader described in Example 3. NH₄Cl was added to a final concentration of 2 M, and the enzyme activity before and after the addition of NH₄Cl was analyzed to determine the influence of the NH₄Cl concentration on the enzyme activity. The obtained enzyme activity data are shown in Table 9.

TABLE 8

| No. of enzyme | Mutation position | Enzyme activity (U/ml) | Specific enzyme activity (U/mg) | Amino acid SEQ ID NO: | Nucleotide SEQ ID NO: |
|---|---|---|---|---|---|
| 51 | wt(rtDAAO) | 0.015 | 0.009046 | 3 | 4 |
| 52 | rtDAAO(N54V-F58Q-M213S) | 20.49 | 3.21 | 92 | 93 |
| 53 | rtDAAO(N54A-F58H) | 2.96 | 3.69 | 94 | 95 |
| 54 | rtDAAO(N54A-56N-F58H) | 13.33 | 4.29 | 96 | 97 |
| 55 | rtDAAO(C211L-M213T) | 6.30 | 2.21 | 98 | 99 |
| 56 | rtDAAO(N54A-F58H-C211L-M213T) | 3.46 | 0.75 | 100 | 101 |
| 57 | rtDAAO(N54A-T56N-F58H-C211L-M213T) | 12.96 | 2.99 | 102 | 103 |

TABLE 9

| No. of enzyme | Mutation position | Ratio of remaining enzyme activity after adding 2M NH₄Cl | Amino acid SEQ ID NO: | Nucleotide SEQ ID NO: |
|---|---|---|---|---|
| 51 | wt(rtDAAO) | 0 | 3 | 4 |
| 52 | rtDAAO(N54V-F58Q-M213S) | 0.14 | 92 | 93 |
| 53 | rtDAAO(N54A-F58H) | 0.98 | 94 | 95 |
| 54 | rtD AAO(N54A-T56N-F58H) | 0.29 | 96 | 97 |
| 55 | rtDAAO(C211L-M213T) | 0.10 | 98 | 99 |
| 56 | rtDAAO(N54A-F58H-C211L-M213T) | 0.78 | 100 | 101 |
| 57 | rtDAAO(N54A-T56N-F58H-C211L-M213T) | 0.43 | 102 | 103 |

It can be seen from the above Table that the ammonium tolerance of mutant 56 (N54A-F58H-C211L-M213T) is improved; the ammonium tolerance of mutant 57 (N54A-T56N-F58H-C211L-M213T) is improved with little change in enzyme activity.

What is claimed is:

1. A D-amino acid oxidase mutant, wherein the amino acid sequence of the D-amino acid oxidase mutant is SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 70, SEQ ID NO: 72, SEQ ID NO: 75, SEQ ID NO: 79, SEQ ID NO: 82, SEQ ID NO: 90, SEQ ID NO: 100, or SEQ ID NO: 102.

2. An isolated nucleic acid, wherein the nucleic acid encodes the D-amino acid oxidase mutant of claim 1.

3. A recombinant expression vector comprising the nucleic acid of claim 2.

4. A transformant comprising the nucleic acid of claim 2.

5. A method for preparing 2-oxo-4-(hydroxymethylphosphinyl) butyric acid comprising:
using the D-amino acid oxidase mutant of claim 1 to prepare the 2-oxo-4-(hydroxymethylphosphinyl) butyric acid.

6. The nucleic acid of claim 2, wherein the nucleic acid is SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 67, SEQ ID NO: 69, SEQ ID NO: 71, SEQ ID NO: 73, SEQ ID NO: 74, SEQ ID NO: 76, SEQ ID NO: 77, SEQ ID NO: 78, SEQ ID NO: 80, SEQ ID NO: 81, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 91, SEQ ID NO: 101 or SEQ ID NO: 103.

7. A transformant comprising the recombinant expression vector of claim 3.

8. The D-amino acid oxidase mutant of claim 1, wherein the amino acid sequence of the D-amino acid oxidase mutant is SEQ ID NO: 9, SEQ ID NO: 11, SEQ ID NO: 13, SEQ ID NO: 15, SEQ ID NO: 19, SEQ ID NO: 21, SEQ ID NO: 23, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 70, SEQ ID NO: 72, SEQ ID NO: 75, SEQ ID NO: 79, SEQ ID NO: 82 or SEQ ID NO: 90.

9. The D-amino acid oxidase mutant of claim 8, wherein the amino acid sequence of the D-amino acid oxidase mutant is SEQ ID NO: 61, SEQ ID NO: 63, SEQ ID NO: 72, SEQ ID NO: 79, SEQ ID NO: 82 or SEQ ID NO: 90.

10. The D-amino acid oxidase mutant of claim 1, wherein the amino acid sequence of the D-amino acid oxidase mutant is SEQ ID NO: 100 or SEQ ID NO: 102.

11. The nucleic acid of claim 6, wherein the nucleic acid is SEQ ID NO: 10, SEQ ID NO: 12, SEQ ID NO: 14, SEQ ID NO: 16, SEQ ID NO: 20, SEQ ID NO: 22, SEQ ID NO:32, SEQ ID NO:34, SEQ ID NO: 24, SEQ ID NO:32, SEQ ID NO:34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 67, SEQ ID NO: 71, SEQ ID NO: 73, SEQ ID NO: 74, SEQ ID NO: 77, SEQ ID NO: 78, SEQ ID NO: 80, SEQ ID NO: 81, SEQ ID NO: 83, SEQ ID NO: 84, SEQ ID NO: 85, SEQ ID NO: 86, SEQ ID NO: 87, SEQ ID NO: 88, SEQ ID NO: 89 or SEQ ID NO: 91.

12. The nucleic acid of claim 6, wherein the nucleic acid is SEQ ID NO: 64, SEQ ID NO: 73, SEQ ID NO: 77, SEQ ID NO: 78, SEQ ID NO: 80, SEQ ID NO: 81, SEQ ID NO: 83, SEQ ID NO: 84, SEQ ID NO: 85, SEQ ID NO: 86, SEQ ID NO: 89 or SEQ ID NO: 91.

13. The nucleic acid of claim 6, wherein the nucleic acid is SEQ ID NO: 101 or SEQ ID NO: 103.

* * * * *

SEQUENCE LISTING

<160> NUMBER OF SEQ ID NOS: 107

<210> SEQ ID NO 1
<211> LENGTH: 372
<212> TYPE: PRT
<213> ORGANISM: Rhodotorula sp. JG-1b

<400> SEQUENCE: 1

Met Thr Gln Asn Lys Arg Val Val Leu Gly Ser Gly Val Ile Gly
1               5                  10                 15

Leu Ser Cys Ala Leu Ala Leu Ala Gln Lys Gly Tyr Lys Val His Val
            20                 25                 30

Val Ala Arg Asp Leu Pro Glu Asp Thr Val Ala Gln Thr Phe Ala Ser
        35                 40                 45

Pro Trp Ala Gly Ala Asn Trp Thr Pro Phe Met Ser Lys Glu Ala Gly
    50                 55                 60

Pro Arg Gln Ala Lys Trp Glu Glu Ala Thr Phe Lys Gln Trp Val Asp
65                 70                 75                 80

Phe Val Pro Gln Gly Leu Ala Met Trp Leu Lys Gly Thr Arg Arg Phe
                85                 90                 95

Ala Glu Thr Glu Ala Asp Leu Leu Gly His Trp Tyr Lys Asp Ile Val
            100                105                110

Pro Asn Tyr Arg His Leu Asn Pro Ser Asp Cys Pro Pro Gly Ala Ile
        115                120                125

Gly Val Thr Tyr Asp Thr Leu Ser Val Asn Ala Pro Lys Phe Cys Gln
    130                135                140

Tyr Leu Gln Arg Glu Ala Gln Lys Leu Gly Val Thr Phe Glu Arg Arg
145                150                155                160

Leu Val Thr Ser Leu Glu Gln Ile Ala Asp Gly Ala Asp Leu Ile Val
                165                170                175

Asn Ala Thr Gly Leu Gly Ala Lys Ser Ile Ala Gly Val Glu Asp Gln
            180                185                190

Glu Val Glu Pro Ile Arg Gly Gln Thr Val Leu Ile Lys Ser Asn Cys
        195                200                205

Lys Arg Cys Thr Met Asp Ser Ser Asp Pro Lys Ser Pro Ala Tyr Ile
    210                215                220

Ile Pro Arg Pro Gly Gly Glu Val Ile Cys Gly Gly Thr Tyr Leu Val
225                230                235                240

Gly Asn Tyr Asp Leu Ser Val Asp Pro Ala Thr Ile Pro Arg Ile Leu
            245                 250                 255

Lys His Cys Leu Arg Leu Asp Pro Ser Ile Ser Thr Asp Gly Thr Leu
        260                 265                 270

Glu Gly Ile Glu Ile Leu Arg His Asn Val Gly Leu Arg Pro Ala Arg
    275                 280                 285

Arg Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 2
<211> LENGTH: 1116
<212> TYPE: DNA
<213> ORGANISM: Rhodotorula sp. JG-1b

<400> SEQUENCE: 2

```
atgacccaga caaacgtgt tgttgttctg ggttctggtg ttatcggtct gtcttgcgct    60
ctggctctgg ctcagaaagg ttacaaagtt cacgttgttg ctcgtgaccct gccggaagac   120
accgttgctc agaccttcgc ttctccgtgg gctggtgcta actggacccc gttcatgtct   180
aaagaagctg gtccgcgtca ggctaaatgg gaagaagcta ccttcaaaca gtgggttgac   240
ttcgttccgc agggtctggc tatgtggctg aaaggtaccc gtcgtttcgc tgaaaccgaa   300
gctgacctgc tgggtcactg gtacaaagac atcgttccga actaccgtca cctgaacccg   360
tctgactgcc cgccgggtgc tatcggtgtt acctacgaca ccctgtctgt taacgctccg   420
aaattctgcc agtacctgca gcgtgaagct cagaaactgg gtgttacctt cgaacgtcgt   480
ctggttacct ctctggaaca gatcgctgac ggtgctgacc tgatcgttaa cgctaccggt   540
ctgggtgcta atctatcgc tggtgttgaa gaccaggaag ttgaaccgat ccgtggtcag   600
accgttctga tcaaatctaa ctgcaaacgt tgcaccatgg actcttctga cccgaaatct   660
ccggcttaca tcatcccgcg tccgggtggt gaagttatct gcggtggtac ctacctggtt   720
ggtaactacg acctgtctgt tgacccgggct accatcccgc gtatcctgaa acactgcctg   780
cgtctggacc cgtctatctc taccgacggt accctggaag gtatcgaaat cctgcgtcac   840
aacgttggtc tgcgtccggc tcgtcgtggt ggtccgcgtg ttgaactgga acgtgtttct   900
ttcccgctga acgtggtca gtctctgctg gctctgggta ccgctaaagc tgctgaaggt   960
aaagcttctc gtaccgttcc ggttgttcac gcttacggtt tctcttctgc tggttaccag  1020
cagggttggg gtgctgctct ggaagttcgt gacctggttg accaggctat cggttcttct  1080
tcttctgctt cttctggtcg ttacctggct aaactg                            1116
```

<210> SEQ ID NO 3
<211> LENGTH: 368
<212> TYPE: PRT
<213> ORGANISM: Rhodosporidium toruloides

<400> SEQUENCE: 3

```
Met His Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Asn Trp Thr Pro Phe Met Thr Leu Thr Asp Gly
    50                  55                  60

Pro Arg Gln Ala Lys Trp Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Arg Cys Thr Met Asp Ser Ser Asp Pro Ala Ser Pro Ala Tyr Ile
210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
    290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365
```

<210> SEQ ID NO 4
<211> LENGTH: 1104
<212> TYPE: DNA
<213> ORGANISM: Rhodosporidium toruloides

<400> SEQUENCE: 4

```
atgcactctc agaaacgtgt tgttgttctg ggttctggtg ttatcggtct gtcttctgct    60
ctgatcctgg ctcgtaaagg ttactctgtt cacatcctgg ctcgtgacct gccggaagac   120
gtttcttctc agaccttcgc ttctccgtgg gctggtgcta actggacccc gttcatgacc   180
ctgaccgacg tccgcgtca ggctaaatgg aagaatcta ccttcaaaaa atgggttgaa    240
ctggttccga ccggtcacgc tatgtggctg aaaggtaccc gtcgtttcgc tcagaacgaa   300
gacggtctgc tgggtcactg gtacaaagac atcaccccga actaccgtcc gctgccgtct   360
tctgaatgcc cgccgggtgc tatcggtgtt acctacgaca ccctgtctgt tcacgctccg   420
aaatactgcc agtacctggc tcgtgaactg cagaaactgg gtgctacctt cgaacgtcgt   480
accgttacct ctctggaaca ggctttcgac ggtgctgacc tggttgttaa cgctaccggt   540
ctgggtgcta atctatcgc tggtatcgac gaccaggctg ctgaaccgat ccgtggtcag   600
accgttctgg ttaaatctcc gtgcaaacgt tgcaccatgg actcttctga cccggcttct   660
ccggcttaca tcatcccgcg tccgggtggt gaagttatct gcggtggtac ctacggtgtt   720
ggtgactggg acctgtctgt taacccggaa accgttcagc gtatcctgaa acactgcctg   780
cgtctggacc cgaccatctc ttctgacggt accatcgaag gtatcgaagt tctgcgtcac   840
aacgttggtc tgcgtccggc tcgtcgtggt ggtccgcgtg ttgaagctga acgtatcgtt   900
ctgccgctgg accgtaccaa atctccgctg tctctgggtc gtggttctgc tcgtgctgct   960
aaagaaaaag aagttaccct ggttcacgct tacggtttct cttctgctgg ttaccagcag  1020
tcttggggtg ctgctgaaga cgttgctcag ctggttgacg aagcttttca gcgttaccac  1080
ggtgctgctc gtgaatctaa actg                                         1104
```

<210> SEQ ID NO 5
<211> LENGTH: 372
<212> TYPE: PRT
<213> ORGANISM: Artificial Sequence
<220> FEATURE:
<223> OTHER INFORMATION: N2DAAO(N54V-F58Q-M213S)

<400> SEQUENCE: 5

```
Met Thr Gln Asn Lys Arg Val Val Leu Gly Ser Gly Val Ile Gly
 1               5                  10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
            35                  40                  45

Pro Trp Ala Gly Ala Val Trp Thr Pro Gln Met Ser Lys Glu Ala Gly
        50                  55                  60

Pro Arg Gln Ala Lys Trp Glu Glu Ala Thr Phe Lys Gln Trp Val Asp
    65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
               100                 105                 110

Pro Asn Tyr Arg His Leu Asn Pro Ser Asp Cys Pro Pro Gly Ala Ile
            115                 120                 125

Gly Val Thr Tyr Asp Thr Leu Ser Val Asn Ala Pro Lys Phe Cys Gln
        130                 135                 140

Tyr Leu Gln Arg Glu Ala Gln Lys Leu Gly Val Thr Phe Glu Arg Arg
    145                 150                 155                 160
```

```
Leu Val Thr Ser Leu Glu Gln Ile Ala Asp Gly Ala Asp Leu Ile Val
            165                 170                 175
Asn Ala Thr Gly Leu Gly Ala Lys Ser Ile Ala Gly Val Glu Asp Gln
        180                 185                 190
Glu Val Glu Pro Ile Arg Gly Gln Thr Val Leu Ile Lys Ser Asn Cys
    195                 200                 205
Lys Arg Cys Thr Ser Asp Ser Ser Asp Pro Lys Ser Pro Ala Tyr Ile
210                 215                 220
Ile Pro Arg Pro Gly Glu Val Ile Cys Gly Thr Tyr Leu Val
225                 230                 235                 240
Gly Asn Tyr Asp Leu Ser Val Asp Pro Ala Thr Ile Pro Arg Ile Leu
            245                 250                 255
Lys His Cys Leu Arg Leu Asp Pro Ser Ile Ser Thr Asp Gly Thr Leu
        260                 265                 270
Glu Gly Ile Glu Ile Leu Arg His Asn Val Gly Leu Arg Pro Ala Arg
    275                 280                 285
Arg Gly Gly Pro Arg Val Glu Leu Glu Arg Val Ser Phe Pro Leu Lys
290                 295                 300
Arg Gly Gln Ser Leu Leu Ala Leu Gly Thr Ala Lys Ala Ala Glu Gly
305                 310                 315                 320
Lys Ala Ser Arg Thr Val Pro Val Val His Ala Tyr Gly Phe Ser Ser
            325                 330                 335
Ala Gly Tyr Gln Gln Gly Trp Gly Ala Ala Leu Glu Val Arg Asp Leu
        340                 345                 350
Val Asp Gln Ala Ile Gly Ser Ser Ser Ser Ala Ser Ser Gly Arg Tyr
    355                 360                 365
Leu Ala Lys Leu
    370

<210> SEQ ID NO 6
<211> LENGTH: 1116
<212> TYPE: DNA
<213> ORGANISM: Artificial Sequence
<220> FEATURE:
<223> OTHER INFORMATION: N2DAAO(N54V-F58Q-M213S)

<400> SEQUENCE: 6
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag tttggacccc gcagatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata cttttaagcg taacgccccg     420
aagttctgtc agtatctgca gcgcgaagca cagaaactgg gcgtgacctt cgaacgcgt      480 ttagttacct ctttagagca gattgcagat ggcgccgatc tgatcgttaa tgcaaccggt     540
ctgggcgcca aaagcatcgc cggtgtggaa gatcaagaag tggaacctat ccgcggccaa     600
acagtgctga ttaagagcaa ctgtaaacgc tgtaccagcg acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcattttaaa acattgtctg     780
cgtttagacc cgagtattag caccgacggc acactggaag gcatcgaaat tttacgccat     840
```

```
aacgttggtc tgcgtcccgc tcgtcgtggt ggtccgcgtg tggaattaga acgcgtgagc    900
ttcccgctga agcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg gcgcagcttt agaagttcgt gatctggtgg accaagctat tggtagcagc   1080
agtagtgcca gtagtggccg ttatttagcc aaactg                             1116
```

<210> SEQ ID NO 7
<211> LENGTH: 372
<212> TYPE: PRT
<213> ORGANISM: Artificial Sequence
<220> FEATURE:
<223> OTHER INFORMATION: N54V-F58Q-C211S-M213T

<400> SEQUENCE: 7

```
Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Ser Thr Thr Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
```

```
                305                 310                 315                 320
Lys Ala Ser Arg Thr Val Pro Val Val His Ala Tyr Gly Phe Ser Ser
                    325                 330                 335

Ala Gly Tyr Gln Gln Gly Trp Gly Ala Ala Leu Glu Val Arg Asp Leu
                340                 345                 350

Val Asp Gln Ala Ile Gly Ser Ser Ser Ala Ser Ser Gly Arg Tyr
            355                 360                 365

Leu Ala Lys Leu
    370

<210> SEQ ID NO 8
<211> LENGTH: 1116
<212> TYPE: DNA
<213> ORGANISM: Artificial Sequence
<220> FEATURE:
<223> OTHER INFORMATION: N54V-F58Q-C211S-M213T

<400> SEQUENCE: 8
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag tttggacccc gcagatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata ctttaagcgt taacgccccg     420
aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtggaa gatcaagaag tggaacctat ccgcggccaa     600
acagtgctga ttaagagcaa ctgtaaacgc agtaccacgg acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcattttaaa acattgtctg     780
cgtttagacc cgagtattag caccgacggc acactggaag gcatcgaaat tttacgccat     840
aacgttggtc tgcgtcccgc tcgtcgtggt ggtccgcgtg tggaattaga acgcgtgagc     900
ttcccgctga agcgcggtca gagtctgtta gctttaggca ccgccaaagc agcagaaggt     960
aaagcaagcc gtaccgtgcc ggttgttcat gcctatggct tcagcagcgc cggttaccaa    1020
caaggttggg gcgcagcttt agaagttcgt gatctggtgg accaagctat tggtagcagc    1080
agtagtgcca gtagtggccg ttatttagcc aaactg                              1116

<210> SEQ ID NO 9
<211> LENGTH: 372
<212> TYPE: PRT
<213> ORGANISM: Artificial Sequence
<220> FEATURE:
<223> OTHER INFORMATION: N54V-F58Q-C211A-M213T

<400> SEQUENCE: 9

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
```

```
            35                  40                  45
Pro Trp Ala Gly Ala Val Trp Thr Pro Gln Met Ser Lys Glu Ala Gly
 50                  55                  60

Pro Arg Gln Ala Lys Trp Glu Glu Ala Thr Phe Lys Gln Trp Val Asp
 65                  70                  75                  80

Phe Val Pro Gln Gly Leu Ala Met Trp Leu Lys Gly Thr Arg Arg Phe
                 85                  90                  95

Ala Glu Thr Glu Ala Asp Leu Leu Gly His Trp Tyr Lys Asp Ile Val
                100                 105                 110

Pro Asn Tyr Arg His Leu Asn Pro Ser Asp Cys Pro Pro Gly Ala Ile
                115                 120                 125

Gly Val Thr Tyr Asp Thr Leu Ser Val Asn Ala Pro Lys Phe Cys Gln
                130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
                180                 185                 190

Glu Val Glu Pro Ile Arg Gly Gln Thr Val Leu Ile Lys Ser Asn Cys
                195                 200                 205

Lys Arg Ala Thr Thr Asp Ser Ser Asp Pro Lys Ser Pro Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
                260                 265                 270

Glu Gly Ile Glu Ile Leu Arg His Asn Val Gly Leu Arg Pro Ala Arg
                275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val His Ala Tyr Gly Phe Ser Ser
                325                 330                 335

Ala Gly Tyr Gln Gln Gly Trp Gly Ala Ala Leu Glu Val Arg Asp Leu
                340                 345                 350

Val Asp Gln Ala Ile Gly Ser Ser Ser Ala Ser Ser Gly Arg Tyr
                355                 360                 365

Leu Ala Lys Leu
    370

<210> SEQ ID NO 10
<211> LENGTH: 1116
<212> TYPE: DNA
<213> ORGANISM: Artificial Sequence
<220> FEATURE:
<223> OTHER INFORMATION: N54V-F58Q-C211A-M213T

<400> SEQUENCE: 10
atgacccaga ataagcgcgt ggttgttctg ggcagtggcg ttattggtct gagctgtgct    60
ttagctttag cccagaaggg ctataaagtg catgtggttg cccgcgatct gccggaagac   120
```

-continued

```
acagtggccc agacctttgc aagcccttgg gccggtgcag tttggacccc gcagatgagc    180
aaagaagctg gtccgcgtca agctaaatgg gaggaagcaa ccttcaaaca gtgggtggac    240
ttcgttccgc aaggtctggc aatgtggctg aaaggtaccc gccgctttgc agaaaccgaa    300
gccgatctgc tgggccattg gtataaggac atcgtgccga attaccgcca tctgaacccg    360
agcgattgtc cgccgggcgc aattggcgtg acctacgata ctttaagcgt taacgccccg    420
aagttctgtc agtatctgca gcgcgaagca cagaaactgg gcgtgacctt cgaacgccgt    480
ttagttacct ctttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc gcgaccactg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcatttttaaa acattgtctg    780 cgtttagacc cgagtattag caccgacggc acactggaag catcgaaat tttacgccat    840 aacgttggtc tgcgtcccgc tcgtcgtggt ggtccgcgtg tggaattaga acgcgtgagc    900
ttcccgctga agcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg gcgcagcttt agaagttcgt gatctggtgg accaagctat tggtagcagc   1080
agtagtgcca gtagtggccg ttatttagcc aaactg                             1116
```

<210> SEQ ID NO 11
<211> LENGTH: 372
<212> TYPE: PRT
<213> ORGANISM: Artificial Sequence
<220> FEATURE:
<223> OTHER INFORMATION: N54V-F58Q-C211G-M213F

<400> SEQUENCE: 11

```
Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190
```

```
Glu Val Glu Pro Ile Arg Gly Gln Thr Val Leu Ile Lys Ser Asn Cys
            195                 200                 205
Lys Arg Gly Thr Phe Asp Ser Ser Asp Pro Lys Ser Pro Ala Tyr Ile
    210                 215                 220
Ile Pro Arg Pro Gly Gly Glu Val Ile Cys Gly Gly Thr Tyr Leu Val
225                 230                 235                 240
Gly Asn Tyr Asp Leu Ser Val Asp Pro Ala Thr Ile Pro Arg Ile Leu
                245                 250                 255
Lys His Cys Leu Arg Leu Asp Pro Ser Ile Ser Thr Asp Gly Thr Leu
            260                 265                 270
Glu Gly Ile Glu Ile Leu Arg His Asn Val Gly Leu Arg Pro Ala Arg
        275                 280                 285
Arg Gly Gly Pro Arg Val Glu Leu Glu Arg Val Ser Phe Pro Leu Lys
290                 295                 300
Arg Gly Gln Ser Leu Leu Ala Leu Gly Thr Ala Lys Ala Ala Glu Gly
305                 310                 315                 320
Lys Ala Ser Arg Thr Val Pro Val Val His Ala Tyr Gly Phe Ser Ser
                325                 330                 335
Ala Gly Tyr Gln Gln Gly Trp Gly Ala Ala Leu Glu Val Arg Asp Leu
            340                 345                 350
Val Asp Gln Ala Ile Gly Ser Ser Ser Ala Ser Ser Gly Arg Tyr
        355                 360                 365
Leu Ala Lys Leu
        370

<210> SEQ ID NO 12
<211> LENGTH: 1116
<212> TYPE: DNA
<213> ORGANISM: Artificial Sequence
<220> FEATURE:
<223> OTHER INFORMATION: N54V-F58Q-C211G-M213F

<400> SEQUENCE: 12
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag tttggacccc gcagatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata ctttaagcgt taacgccccg     420
aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtggaa gatcaagaag tggaacctat ccgcggccaa     600
acagtgctga ttaagagcaa ctgtaaacgc ggtacctttg acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcattttaaa acattgtctg     780
cgtttagacc cgagtattag caccgacggc acactggaag gcatcgaaat tttacgccat     840
aacgttggtc tgcgtcccgc tcgtcgtggt ggtccgcgtg tggaattaga acgcgtgagc     900
ttcccgctga gcgcggtca gagtctgtta gctttaggca ccgccaaagc agcagaaggt     960
```

```
aaagcaagcc gtaccgtgcc ggttgttcat gcctatggct tcagcagcgc cggttaccaa    1020
caaggttggg gcgcagcttt agaagttcgt gatctggtgg accaagctat tggtagcagc    1080
agtagtgcca gtagtggccg ttatttagcc aaactg                              1116
```

<210> SEQ ID NO 13
<211> LENGTH: 372
<212> TYPE: PRT
<213> ORGANISM: Artificial Sequence
<220> FEATURE:
<223> OTHER INFORMATION: N54V-F58Q-C211M-M213R

<400> SEQUENCE: 13

```
Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Met Thr Arg Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335
```

Ala Gly Tyr Gln Gln Gly Trp Gly Ala Ala Leu Glu Val Arg Asp Leu
                340                 345                 350

Val Asp Gln Ala Ile Gly Ser Ser Ser Ala Ser Ser Gly Arg Tyr
            355                 360                 365

Leu Ala Lys Leu
        370

<210> SEQ ID NO 14
<211> LENGTH: 1116
<212> TYPE: DNA
<213> ORGANISM: Artificial Sequence
<220> FEATURE:
<223> OTHER INFORMATION: N54V-F58Q-C211M-M213R

<400> SEQUENCE: 14

```
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag tttggacccc gcagatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata cttttaagcg taacgccccg     420
aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtggaa gatcaagaag tggaacctat ccgcggccaa     600
acagtgctga ttaagagcaa ctgtaaacgc acgacccatg acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcatttttaaa acattgtctg     780
cgtttagacc cgagtattag caccgacggc acactggaag gcatcgaaat tttacgccat     840
aacgttggtc tgcgtcccgc tcgtcgtggt ggtccgcgtg tggaattaga acgcgtgagc     900
ttcccgctga gcgcggtca gagtctgtta gctttaggca ccgccaaagc agcagaaggt     960
aaagcaagcc gtaccgtgcc ggttgttcat gcctatggct tcagcagcgc cggttaccaa    1020
caaggttggg gcgcagcttt agaagttcgt gatctggtgg accaagctat tggtagcagc    1080
agtagtgcca gtagtggccg ttatttagcc aaactg                              1116
```

<210> SEQ ID NO 15
<211> LENGTH: 372
<212> TYPE: PRT
<213> ORGANISM: Artificial Sequence
<220> FEATURE:
<223> OTHER INFORMATION: N54V-F58Q-C211G-M213T

<400> SEQUENCE: 15

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
 65                  70                  75                  80

Phe Val Pro Gln Gly Leu Ala Met Trp Leu Lys Gly Thr Arg Arg Phe
             85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Gly Thr Thr Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 16
<211> LENGTH: 1116
<212> TYPE: DNA
<213> ORGANISM: Artificial Sequence
<220> FEATURE:
<223> OTHER INFORMATION: N54V-F58Q-C211G-M213T

<400> SEQUENCE: 16
atgacccaga ataagcgcgt ggttgttctg ggcagtggcg ttattggtct gagctgtgct     60
ttagctttag cccagaaggg ctataaagtg catgtggttg cccgcgatct gccggaagac    120
acagtggccc agacctttgc aagcccttgg gccggtgcag tttggacccc gcagatgagc    180
aaagaagctg tccgcgtcaa agctaaatgg gaggaagcaa ccttcaaaca gtgggtggac    240
ttcgttccgc aaggtctggc aatgtggctg aaaggtaccc gccgctttgc agaaaccgaa    300

-continued

```
gccgatctgc tgggccattg gtataaggac atcgtgccga attaccgcca tctgaacccg    360
agcgattgtc cgccgggcgc aattggcgtg acctacgata ctttaagcgt taacgccccg    420
aagttctgtc agtatctgca gcgcgaagca cagaaactgg gcgtgacctt cgaacgccgt    480
ttagttacct ctttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc gggaccactg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag gcatcgaaat tttacgccat    840
aacgttggtc tgcgtcccgc tcgtcgtggt ggtccgcgtg tggaattaga acgcgtgagc    900
ttcccgctga gcgcggtca gagtctgtta gctttaggca ccgccaaagc agcagaaggt    960
aaagcaagcc gtaccgtgcc ggttgttcat gcctatggct tcagcagcgc cggttaccaa    1020
caaggttggg gcgcagcttt agaagttcgt gatctggtgg accaagctat tggtagcagc    1080
agtagtgcca gtagtggccg ttatttagcc aaactg                              1116
```

<210> SEQ ID NO 17
<211> LENGTH: 372
<212> TYPE: PRT
<213> ORGANISM: Artificial Sequence
<220> FEATURE:
<223> OTHER INFORMATION: N54V-F58Q-C211A-M213R

<400> SEQUENCE: 17

```
Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
                35                  40                  45

Pro Trp Ala Gly Ala Val Trp Thr Pro Gln Met Ser Lys Glu Ala Gly
        50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                        85                  90                  95

Ala Glu Thr Glu Ala Asp Leu Leu Gly His Trp Tyr Lys Asp Ile Val
                100                 105                 110

Pro Asn Tyr Arg His Leu Asn Pro Ser Asp Cys Pro Pro Gly Ala Ile
                115                 120                 125

Gly Val Thr Tyr Asp Thr Leu Ser Val Asn Ala Pro Lys Phe Cys Gln
        130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                        165                 170                 175

Asn Ala Thr Gly Leu Gly Ala Lys Ser Ile Ala Gly Val Glu Asp Gln
                180                 185                 190

Glu Val Glu Pro Ile Arg Gly Gln Thr Val Leu Ile Lys Ser Asn Cys
                195                 200                 205

Lys Arg Ala Thr Arg Asp Ser Ser Asp Pro Lys Ser Pro Ala Tyr Ile
```

```
                210               215               220
Ile Pro Arg Pro Gly Gly Glu Val Ile Cys Gly Gly Thr Tyr Leu Val
225               230               235               240

Gly Asn Tyr Asp Leu Ser Val Asp Pro Ala Thr Ile Pro Arg Ile Leu
            245               250               255

Lys His Cys Leu Arg Leu Asp Pro Ser Ile Ser Thr Asp Gly Thr Leu
            260               265               270

Glu Gly Ile Glu Ile Leu Arg His Asn Val Gly Leu Arg Pro Ala Arg
        275               280               285

Arg Gly Gly Pro Arg Val Glu Leu Glu Arg Val Ser Phe Pro Leu Lys
290               295               300

Arg Gly Gln Ser Leu Leu Ala Leu Gly Thr Ala Lys Ala Ala Glu Gly
305               310               315               320

Lys Ala Ser Arg Thr Val Pro Val Val His Ala Tyr Gly Phe Ser Ser
                325               330               335

Ala Gly Tyr Gln Gln Gly Trp Gly Ala Ala Leu Glu Val Arg Asp Leu
            340               345               350

Val Asp Gln Ala Ile Gly Ser Ser Ser Ala Ser Ser Gly Arg Tyr
        355               360               365

Leu Ala Lys Leu
    370

<210> SEQ ID NO 18
<211> LENGTH: 1116
<212> TYPE: DNA
<213> ORGANISM: Artificial Sequence
<220> FEATURE:
<223> OTHER INFORMATION: N54V-F58Q-C211A-M213R

<400> SEQUENCE: 18
atgacccaga taagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag tttggacccc gcagatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc gccgggcgc aattggcgtg acctacgata ctttaagcgt taacccccg      420 aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtggaa gatcaagaag tggaacctat ccgcggccaa     600
acagtgctga ttaagagcaa ctgtaaacgc gctacccgag acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcattttaaa acattgtctg     780
cgtttagacc cgagtattag caccgacggc acactggaag gcatcgaaat tttacgccat     840
aacgttggtc tgcgtcccgc tcgtcgtggt ggtccgcgtg tggaattaga acgcgtgagc     900
ttcccgctga agcgcggtca gagtctgtta gctttaggca ccgccaaagc agcagaaggt     960
aaagcaagcc gtaccgtgcc ggttgttcat gcctatggct tcagcagcgc cggttaccaa    1020
caaggttggg gcgcagcttt agaagttcgt gatctggtgg accaagctat tggtagcagc    1080
agtagtgcca gtagtggccg ttatttagcc aaactg                              1116
```

<210> SEQ ID NO 19
<211> LENGTH: 372
<212> TYPE: PRT
<213> ORGANISM: Artificial Sequence
<220> FEATURE:
<223> OTHER INFORMATION: N54V-F58Q-C211G-M213S

<400> SEQUENCE: 19

```
Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
            35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Gly Thr Ser Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ser Ala Ser Ser Gly Arg Tyr
        355                 360                 365
```

```
<210> SEQ ID NO 20
<211> LENGTH: 1116
<212> TYPE: DNA
<213> ORGANISM: Artificial Sequence
<220> FEATURE:
<223> OTHER INFORMATION: N54V-F58Q-C211G-M213S

<400> SEQUENCE: 20
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag tttggacccc gcagatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata cttaagcgt taacgccccg     420
aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtgaa gatcaagaag tggaacctat ccgcggccaa     600
acagtgctga ttaagagcaa ctgtaaacgc gggacctcgg acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcattttaaa acattgtctg     780
cgtttagacc cgagtattag caccgacggc acactggaag gcatcgaaat tttacgccat     840
aacgttggtc tgcgtcccgc tcgtcgtggt ggtccgcgtg tggaattaga acgcgtgagc     900
ttcccgctga gcgcggtca gagtctgtta gctttaggca ccgccaaagc agcagaaggt     960
aaagcaagcc gtaccgtgcc ggttgttcat gcctatggct cagcagcgc cggttaccaa    1020
caaggttggg cgcagctttt agaagttcgt gatctggtgg accaagctat tggtagcagc    1080
agtagtgcca gtagtggccg ttatttagcc aaactg                              1116

<210> SEQ ID NO 21
<211> LENGTH: 372
<212> TYPE: PRT
<213> ORGANISM: Artificial Sequence
<220> FEATURE:
<223> OTHER INFORMATION: N54V-F58Q-C211D-M213V

<400> SEQUENCE: 21
```

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

```
Ala Glu Thr Glu Ala Asp Leu Leu Gly His Trp Tyr Lys Asp Ile Val
            100                 105                 110
Pro Asn Tyr Arg His Leu Asn Pro Ser Asp Cys Pro Pro Gly Ala Ile
        115                 120                 125
Gly Val Thr Tyr Asp Thr Leu Ser Val Asn Ala Pro Lys Phe Cys Gln
    130                 135                 140
Tyr Leu Gln Arg Glu Ala Gln Lys Leu Gly Val Thr Phe Glu Arg Arg
145                 150                 155                 160
Leu Val Thr Ser Leu Glu Gln Ile Ala Asp Gly Ala Asp Leu Ile Val
                165                 170                 175
Asn Ala Thr Gly Leu Gly Ala Lys Ser Ile Ala Gly Val Glu Asp Gln
            180                 185                 190
Glu Val Glu Pro Ile Arg Gly Gln Thr Val Leu Ile Lys Ser Asn Cys
        195                 200                 205
Lys Arg Asp Thr Val Asp Ser Ser Asp Pro Lys Ser Pro Ala Tyr Ile
    210                 215                 220
Ile Pro Arg Pro Gly Gly Glu Val Ile Cys Gly Gly Thr Tyr Leu Val
225                 230                 235                 240
Gly Asn Tyr Asp Leu Ser Val Asp Pro Ala Thr Ile Pro Arg Ile Leu
                245                 250                 255
Lys His Cys Leu Arg Leu Asp Pro Ser Ile Ser Thr Asp Gly Thr Leu
            260                 265                 270
Glu Gly Ile Glu Ile Leu Arg His Asn Val Gly Leu Arg Pro Ala Arg
        275                 280                 285
Arg Gly Gly Pro Arg Val Glu Leu Arg Val Ser Phe Pro Leu Lys
    290                 295                 300
Arg Gly Gln Ser Leu Leu Ala Leu Gly Thr Ala Lys Ala Ala Glu Gly
305                 310                 315                 320
Lys Ala Ser Arg Thr Val Pro Val Val His Ala Tyr Gly Phe Ser Ser
                325                 330                 335
Ala Gly Tyr Gln Gln Gly Trp Gly Ala Ala Leu Glu Val Arg Asp Leu
            340                 345                 350
Val Asp Gln Ala Ile Gly Ser Ser Ser Ala Ser Ser Gly Arg Tyr
        355                 360                 365
Leu Ala Lys Leu
    370

<210> SEQ ID NO 22
<211> LENGTH: 1116
<212> TYPE: DNA
<213> ORGANISM: Artificial Sequence
<220> FEATURE:
<223> OTHER INFORMATION: N54V-F58Q-C211D-M213V

<400> SEQUENCE: 22
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag tttggacccc gcagatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata ctttaagcgt taacgccccg     420
```

-continued

```
aagttctgtc agtatctgca gcgcgaagca cagaaactgg gcgtgacctt cgaacgccgt    480
ttagttacct ctttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc gataccgtgg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag gcatcgaaat tttacgccat    840
aacgttggtc tgcgtcccgc tcgtcgtggt ggtccgcgtg tggaattaga acgcgtgagc    900
ttcccgctga agcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg gcgcagcttt agaagttcgt gatctggtgg accaagctat tggtagcagc   1080
agtagtgcca gtagtggccg ttatttagcc aaactg                              1116
```

<210> SEQ ID NO 23
<211> LENGTH: 372
<212> TYPE: PRT
<213> ORGANISM: Artificial Sequence
<220> FEATURE:
<223> OTHER INFORMATION: N54V-F58Q-C211L-M213T

<400> SEQUENCE: 23

```
Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                      45

Pro Trp Ala Gly Ala Val Trp Thr Pro Gln Met Ser Lys Glu Ala Gly
50                  55                      60

Pro Arg Gln Ala Lys Trp Glu Glu Ala Thr Phe Lys Gln Trp Val Asp
65                      70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Leu Thr Thr Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240
```

```
Gly Asn Tyr Asp Leu Ser Val Asp Pro Ala Thr Ile Pro Arg Ile Leu
            245                 250                 255

Lys His Cys Leu Arg Leu Asp Pro Ser Ile Ser Thr Asp Gly Thr Leu
        260                 265                 270

Glu Gly Ile Glu Ile Leu Arg His Asn Val Gly Leu Arg Pro Ala Arg
            275                 280                 285

Arg Gly Gly Pro Arg Val Glu Leu Glu Arg Val Ser Phe Pro Leu Lys
        290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
            355                 360                 365

Leu Ala Lys Leu
        370

<210> SEQ ID NO 24
<211> LENGTH: 1116
<212> TYPE: DNA
<213> ORGANISM: Artificial Sequence
<220> FEATURE:
<223> OTHER INFORMATION: N54V-F58Q-C211L-M213T

<400> SEQUENCE: 24
atgacccaga taagcgcgt ggttgttctg ggcagtggcg ttattggtct gagctgtgct      60
ttagctttag cccagaaggg ctataaagtg catgtggttg cccgcgatct gccggaagac    120
acagtggccc agacctttgc aagcccttgg gccggtgcag tttggacccc gcagatgagc    180
aaagaagctg gtccgcgtca gctaaatgg gaggaagcaa ccttcaaaca gtgggtggac    240
ttcgttccgc aaggtctggc aatgtggctg aaaggtaccc gccgctttgc agaaaccgaa    300
gccgatctgc tgggccattg gtataaggac atcgtgccga attaccgcca tctgaacccg    360
agcgattgtc cgccgggcgc aattggcgtg acctacgata cttttaagcg taacgccccg    420
aagttctgtc agtatctgca gcgcgaagca cagaaactgg gcgtgacctt cgaacgccgt    480
ttagttacct ctttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc ctgaccactg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag gcatcgaaat tttacgccat    840
aacgttggtc tgcgtcccgc tcgtcgtggt ggtccgcgtg tggaattaga acgcgtgagc    900
ttcccgctga gcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg gcgcagcttt agaagttcgt gatctggtgg accaagctat tggtagcagc   1080
agtagtgcca gtagtggccg ttatttagcc aaactg                              1116

<210> SEQ ID NO 25
<211> LENGTH: 372
<212> TYPE: PRT
```

<213> ORGANISM: Artificial Sequence
<220> FEATURE:
<223> OTHER INFORMATION: N54V-F58Q- C211A-M213C

<400> SEQUENCE: 25

```
Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
            35                  40                  45

Pro Trp Ala Gly Ala Val Trp Thr Pro Gln Met Ser Lys Glu Ala Gly
        50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Ala Thr Cys Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370
```

<210> SEQ ID NO 26
<211> LENGTH: 1116
<212> TYPE: DNA
<213> ORGANISM: Artificial Sequence
<220> FEATURE:
<223> OTHER INFORMATION: N54V-F58Q- C211A-M213C

<400> SEQUENCE: 26

| | | |
|---|---|---|
| atgacccaga taagcgcgt ggttgttctg ggcagtggcg ttattggtct gagctgtgct | 60 |
| ttagctttag cccagaaggg ctataaagtg catgtggttg cccgcgatct gccggaagac | 120 |
| acagtggccc agacctttgc aagcccttgg gccggtgcag tttggacccc gcagatgagc | 180 |
| aaagaagctg gtccgcgtca agctaaatgg gaggaagcaa ccttcaaaca gtgggtggac | 240 |
| ttcgttccgc aaggtctggc aatgtggctg aaaggtaccc gccgctttgc agaaaccgaa | 300 |
| gccgatctgc tgggccattg gtataaggac atcgtgccga attaccgcca tctgaacccg | 360 |
| agcgattgtc cgccgggcgc aattggcgtg acctacgata cttttaagcg taacgccccg | 420 |
| aagttctgtc agtatctgca gcgcgaagca cagaaactgg gcgtgacctt cgaacgccgt | 480 |
| ttagttacct ctttagagca gattgcagat ggcgccgatc tgatcgttaa tgcaaccggt | 540 |
| ctgggcgcca aaagcatcgc cggtgtggaa gatcaagaag tggaacctat ccgcggccaa | 600 |
| acagtgctga ttaagagcaa ctgtaaacgc gctacctgtg acagtagtga cccgaaaagc | 660 |
| ccggcctaca ttattccgcg cccgggtggt gaagtgatct gtggtggtac ctatttagtg | 720 |
| ggtaactatg atttaagcgt ggatccggcc accattccgc gcatttttaaa acattgtctg | 780 |
| cgtttagacc cgagtattag caccgacggc acactggaag catcgaaat tttacgccat | 840 |
| aacgttggtc tgcgtccgcc tcgtcgtggt ggtccgcgtg tggaattaga acgcgtgagc | 900 |
| ttcccgctga gcgcggtca gagtctgtta gctttaggca ccgccaaagc agcagaaggt | 960 |
| aaagcaagcc gtaccgtgcc ggttgttcat gcctatggct tcagcagcgc cggttaccaa | 1020 |
| caaggttggg cgcagctttt agaagttcgt gatctggtgg accaagctat tggtagcagc | 1080 |
| agtagtgcca gtagtggccg ttatttagcc aaactg | 1116 |

<210> SEQ ID NO 27
<211> LENGTH: 372
<212> TYPE: PRT
<213> ORGANISM: Artificial Sequence
<220> FEATURE:
<223> OTHER INFORMATION: N54V-F58Q- C211A-M213L

<400> SEQUENCE: 27

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile

```
                115                 120                 125
Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Ala Thr Leu Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 28
<211> LENGTH: 1116
<212> TYPE: DNA
<213> ORGANISM: Artificial Sequence
<220> FEATURE:
<223> OTHER INFORMATION: N54V-F58Q- C211A-M213L

<400> SEQUENCE: 28
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag tttggacccc gcagatgagc     180
aaagaagctg gtccgcgtca agctaaatgg gaggaagcaa ccttcaaaca gtgggtggac     240
ttcgttccgc aaggtctggc aatgtggctg aaaggtaccc ccgctttgc agaaaccgaa      300 gccgatctgc tgggccattg gtataaggac atcgtgccga attaccgcca tctgaacccg     360
agcgattgtc gccgggcgc aattggcgtg acctacgata ctttaagcgt taacgccccg      420
aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtggaa gatcaagaag tggaacctat ccgcggccaa     600
```

```
acagtgctga ttaagagcaa ctgtaaacgc gcgacccttg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag gcatcgaaat tttacgccat    840
aacgttggtc tgcgtcccgc tcgtcgtggt ggtccgcgtg tggaattaga acgcgtgagc    900
ttcccgctga agcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg gcgcagcttt agaagttcgt gatctggtgg accaagctat tggtagcagc   1080
agtagtgcca gtagtggccg ttatttagcc aaactg                              1116
```

<210> SEQ ID NO 29
<211> LENGTH: 372
<212> TYPE: PRT
<213> ORGANISM: Artificial Sequence
<220> FEATURE:
<223> OTHER INFORMATION: N54V-F58Q- C211G-M213L

<400> SEQUENCE: 29

```
Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Gly Thr Leu Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270
```

Glu Gly Ile Glu Ile Leu Arg His Asn Val Gly Leu Arg Pro Ala Arg
            275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
                355                 360                 365

Leu Ala Lys Leu
    370

<210> SEQ ID NO 30
<211> LENGTH: 1116
<212> TYPE: DNA
<213> ORGANISM: Artificial Sequence
<220> FEATURE:
<223> OTHER INFORMATION: N54V-F58Q- C211G-M213L

<400> SEQUENCE: 30

| | | |
|---|---|---|
| atgacccaga ataagcgcgt ggttgttctg ggcagtggcg ttattggtct gagctgtgct | 60 |
| ttagctttag cccagaaggg ctataaagtg catgtggttg cccgcgatct gccggaagac | 120 |
| acagtggccc agacctttgc aagcccttgg gccggtgcag tttggacccc gcagatgagc | 180 |
| aaagaagctg gtccgcgtca agctaaatgg gaggaagcaa ccttcaaaca gtgggtggac | 240 |
| ttcgttccgc aaggtctggc aatgtggctg aaaggtaccc gccgctttgc agaaaccgaa | 300 |
| gccgatctgc tgggccattg gtataaggac atcgtgccga attaccgcca tctgaacccg | 360 |
| agcgattgtc cgccgggcgc aattggcgtg acctacgata cttttaagcg taacgccccg | 420 |
| aagttctgtc agtatctgca gcgcgaagca cagaaactgg gcgtgacctt cgaacgccgt | 480 |
| ttagttacct ctttagagca gattgcagat ggcgccgatc tgatcgttaa tgcaaccggt | 540 |
| ctgggcgcca aaagcatcgc cggtgtggaa gatcaagaag tggaacctat ccgcggccaa | 600 |
| acagtgctga ttaagagcaa ctgtaaacgc gggaccattg acagtagtga cccgaaaagc | 660 |
| ccggcctaca ttattccgcg cccgggtggt gaagtgatct gtggtggtac ctatttagtg | 720 |
| ggtaactatg atttaagcgt ggatccggcc accattccgc gcattttaaa acattgtctg | 780 |
| cgtttagacc cgagtattag caccgacggc acactggaag gcatcgaaat tttacgccat | 840 |
| aacgttggtc tgcgtcccgc tcgtcgtggt ggtccgcgtg tggaattaga acgcgtgagc | 900 |
| ttcccgctga gcgcggtca gagtctgtta gctttaggca ccgccaaagc agcagaaggt | 960 |
| aaagcaagcc gtaccgtgcc ggttgttcat gcctatggct tcagcagcgc cggttaccaa | 1020 |
| caaggttggg gcgcagcttt agaagttcgt gatctggtgg accaagctat tggtagcagc | 1080 |
| agtagtgcca gtagtggccg ttatttagcc aaactg | 1116 |

<210> SEQ ID NO 31
<211> LENGTH: 372
<212> TYPE: PRT
<213> ORGANISM: Artificial Sequence
<220> FEATURE:
<223> OTHER INFORMATION: N54V-F58Q- C211M-M213S

<400> SEQUENCE: 31

Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
            35                  40                  45

Pro Trp Ala Gly Ala Val Trp Thr Pro Gln Met Ser Lys Glu Ala Gly
        50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Met Thr Ser Asp Ser Ser Asp Pro Lys Ser Pro Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 32
<211> LENGTH: 1116
<212> TYPE: DNA
<213> ORGANISM: Artificial Sequence
<220> FEATURE:

<223> OTHER INFORMATION: N54V-F58Q- C211M-M213S

<400> SEQUENCE: 32

```
atgacccaga taagcgcgt ggttgttctg ggcagtggcg ttattggtct gagctgtgct      60
ttagctttag cccagaaggg ctataaagtg catgtggttg cccgcgatct gccggaagac    120
acagtggccc agacctttgc aagcccttgg gccggtgcag tttggacccc gcagatgagc    180
aaagaagctg gtccgcgtca agctaaatgg gaggaagcaa ccttcaaaca gtgggtggac    240
ttcgttccgc aaggtctggc aatgtggctg aaaggtaccc gccgctttgc agaaaccgaa    300
gccgatctgc tgggccattg gtataaggac atcgtgccga attaccgcca tctgaacccg    360
agcgattgtc cgccgggcgc aattggcgtg acctacgata cttttaagcg taacgccccg    420
aagttctgtc agtatctgca gcgcgaagca cagaaactgg gcgtgacctt cgaacgccgt    480
ttagttacct ctttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc atgacctctg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcatttttaaa acattgtctg    780
cgtttagacc cgagtattag caccgacggc acactggaag gcatcgaaat tttacgccat    840
aacgttggtc tgcgtcccgc tcgtcgtggt ggtccgcgtg tggaattaga acgcgtgagc    900
ttcccgctga gcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg gcgcagcttt agaagttcgt gatctggtgg accaagctat tggtagcagc   1080
agtagtgcca gtagtggccg ttatttagcc aaactg                              1116
```

<210> SEQ ID NO 33
<211> LENGTH: 372
<212> TYPE: PRT
<213> ORGANISM: Artificial Sequence
<220> FEATURE:
<223> OTHER INFORMATION: N54V-F58Q- C211A-M213S

<400> SEQUENCE: 33

```
Met Thr Gln Asn Lys Arg Val Val Leu Gly Ser Gly Val Ile Gly
1               5                  10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
            35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140
```

| | | | | | | | | | | | | |
|---|---|---|---|---|---|---|---|---|---|---|---|---|
|Tyr|Leu|Gln|Arg|Glu|Ala|Gln|Lys|Leu|Gly|Val|Thr|Phe|Glu|Arg|Arg|
|145| | | | |150| | | | |155| | | | |160|

Leu Val Thr Ser Leu Glu Gln Ile Ala Asp Gly Ala Asp Leu Ile Val
165 170 175

Asn Ala Thr Gly Leu Gly Ala Lys Ser Ile Ala Gly Val Glu Asp Gln
180 185 190

Glu Val Glu Pro Ile Arg Gly Gln Thr Val Leu Ile Lys Ser Asn Cys
195 200 205

Lys Arg Ala Thr Ser Asp Ser Asp Pro Lys Ser Pro Ala Tyr Ile
210 215 220

Ile Pro Arg Pro Gly Gly Glu Val Ile Cys Gly Gly Thr Tyr Leu Val
225 230 235 240

Gly Asn Tyr Asp Leu Ser Val Asp Pro Ala Thr Ile Pro Arg Ile Leu
245 250 255

Lys His Cys Leu Arg Leu Asp Pro Ser Ile Ser Thr Asp Gly Thr Leu
260 265 270

Glu Gly Ile Glu Ile Leu Arg His Asn Val Gly Leu Arg Pro Ala Arg
275 280 285

Arg Gly Gly Pro Arg Val Glu Leu Glu Arg Val Ser Phe Pro Leu Lys
290 295 300

Arg Gly Gln Ser Leu Leu Ala Leu Gly Thr Ala Lys Ala Ala Glu Gly
305 310 315 320

Lys Ala Ser Arg Thr Val Pro Val Val His Ala Tyr Gly Phe Ser Ser
325 330 335

Ala Gly Tyr Gln Gln Gly Trp Gly Ala Ala Leu Glu Val Arg Asp Leu
340 345 350

Val Asp Gln Ala Ile Gly Ser Ser Ser Ser Ala Ser Ser Gly Arg Tyr
355 360 365

Leu Ala Lys Leu
370

<210> SEQ ID NO 34
<211> LENGTH: 1116
<212> TYPE: DNA
<213> ORGANISM: Artificial Sequence
<220> FEATURE:
<223> OTHER INFORMATION: N54V-F58Q- C211A-M213S

<400> SEQUENCE: 34

```
atgacccaga ataagcgcgt ggttgttctg ggcagtggcg ttattggtct gagctgtgct    60
ttagctttag cccagaaggg ctataaagtg catgtggttg cccgcgatct gccggaagac   120
acagtggccc agacctttgc aagcccttgg gccggtgcag tttggacccc gcagatgagc   180
aaagaagctg tccgcgtca gctaaatgg aggaagcaa ccttcaaaca gtgggtggac     240
ttcgttccgc aaggtctggc aatgtggctg aaaggtaccc gccgctttgc agaaaccgaa   300
gccgatctgc tgggccattg gtataaggac atcgtgccga attaccgcca tctgaacccg   360
agcgattgtc cgccgggcgc aattggcgtg acctacgata cctttaagcgt taacgccccg   420
aagttctgtc agtatctgca gcgcgaagca cagaaactgg gcgtgacctt cgaacgccgt   480
ttagttacct ctttagagca gattgcagat ggcgccgatc tgatcgttaa tgcaaccggt   540
ctgggcgcca aaagcatcgc cggtgtggaa gatcaagaag tggaacctat ccgcggccaa   600
acagtgctga ttaagagcaa ctgtaaacgc gcgaccagtg acagtagtga cccgaaaagc   660
ccggcctaca ttattccgcg cccgggtggt gaagtgatct gtggtggtac ctatttagtg   720
```

```
ggtaactatg atttaagcgt ggatccggcc accattccgc gcattttaaa acattgtctg   780
cgtttagacc cgagtattag caccgacggc acactggaag gcatcgaaat tttacgccat   840
aacgttggtc tgcgtcccgc tcgtcgtggt ggtccgcgtg tggaattaga acgcgtgagc   900
ttcccgctga agcgcggtca gagtctgtta gctttaggca ccgccaaagc agcagaaggt   960
aaagcaagcc gtaccgtgcc ggttgttcat gcctatggct tcagcagcgc cggttaccaa  1020
caaggttggg cgcagctttt agaagttcgt gatctggtgg accaagctat tggtagcagc  1080
agtagtgcca gtagtggccg ttatttagcc aaactg                            1116
```

<210> SEQ ID NO 35
<211> LENGTH: 372
<212> TYPE: PRT
<213> ORGANISM: Artificial Sequence
<220> FEATURE:
<223> OTHER INFORMATION: N54V-F58Q- C211H-M213L

<400> SEQUENCE: 35

```
Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg His Thr Leu Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
```

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
                340                 345                 350

Val Asp Gln Ala Ile Gly Ser Ser Ser Ala Ser Ser Gly Arg Tyr
            355                 360                 365

Leu Ala Lys Leu
    370

<210> SEQ ID NO 36
<211> LENGTH: 1116
<212> TYPE: DNA
<213> ORGANISM: Artificial Sequence
<220> FEATURE:
<223> OTHER INFORMATION: N54V-F58Q- C211H-M213L

<400> SEQUENCE: 36

```
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag tttggacccc gcagatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata ctttaagcgt taacgccccg     420
aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtggaa gatcaagaag tggaacctat ccgcggccaa     600
acagtgctga ttaagagcaa ctgtaaacgc atacccctgg acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcattttaaa acattgtctg     780
cgtttagacc cgagtattag caccgacggc acactggaag catcgaaaat tttacgccat     840
aacgttggtc tgcgtcccgc tcgtcgtggt ggtccgcgtg tggaattaga acgcgtgagc     900
ttcccgctga agcgcggtca gagtctgtta gctttaggca ccgccaaagc agcagaaggt     960
aaagcaagcc gtaccgtgcc ggttgttcat gcctatggct tcagcagcgc cggttaccaa    1020
caaggttggg gcgcagcttt agaagttcgt gatctggtgg accaagctat tggtagcagc    1080
agtagtgcca gtagtggccg ttatttagcc aaactg                              1116
```

<210> SEQ ID NO 37
<211> LENGTH: 372
<212> TYPE: PRT
<213> ORGANISM: Artificial Sequence
<220> FEATURE:
<223> OTHER INFORMATION: N54V-F58Q-C211S-M213C

<400> SEQUENCE: 37

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val

```
            20                  25                  30
Val Ala Arg Asp Leu Pro Glu Asp Thr Val Ala Gln Thr Phe Ala Ser
    35                  40                  45

Pro Trp Ala Gly Ala Val Trp Thr Pro Gln Met Ser Lys Glu Ala Gly
50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Ser Thr Cys Asp Ser Ser Asp Pro Lys Ser Pro Ala Tyr Ile
    210                 215                 220

Ile Pro Arg Pro Gly Gly Glu Val Ile Cys Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 38
<211> LENGTH: 1116
<212> TYPE: DNA
<213> ORGANISM: Artificial Sequence
<220> FEATURE:
<223> OTHER INFORMATION: N54V-F58Q-C211S-M213C

<400> SEQUENCE: 38
atgacccaga ataagcgcgt ggttgttctg ggcagtggcg ttattggtct gagctgtgct      60
```

```
ttagctttag cccagaaggg ctataaagtg catgtggttg cccgcgatct gccggaagac    120
acagtggccc agacctttgc aagcccttgg gccggtgcag tttggacccc gcagatgagc    180
aaagaagctg gtccgcgtca agctaaatgg gaggaagcaa ccttcaaaca gtgggtggac    240
ttcgttccgc aaggtctggc aatgtggctg aaaggtaccc gccgctttgc agaaaccgaa    300
gccgatctgc tgggccattg gtataaggac atcgtgccga attaccgcca tctgaacccg    360
agcgattgtc cgccgggcgc aattggcgtg acctacgata ctttaagcgt taacgccccg    420
aagttctgtc agtatctgca gcgcgaagca cagaaactgg gcgtgacctt cgaacgccgt    480
ttagttacct ctttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc tcgacctgtg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag gcatcgaaat tttacgccat    840
aacgttggtc tgcgtcccgc tcgtcgtggt ggtccgcgtg tggaattaga acgcgtgagc    900
ttcccgctga gcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg gcgcagcttt agaagttcgt gatctggtgg accaagctat tggtagcagc   1080
agtagtgcca gtagtggccg ttatttagcc aaactg                              1116
```

```
<210> SEQ ID NO 39
<211> LENGTH: 372
<212> TYPE: PRT
<213> ORGANISM: Artificial Sequence
<220> FEATURE:
<223> OTHER INFORMATION: N54V-F58Q-C211M-M213L

<400> SEQUENCE: 39

Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175
```

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Met Thr Leu Asp Ser Ser Asp Pro Lys Ser Pro Ala Tyr Ile
    210                 215                 220

Ile Pro Arg Pro Gly Gly Glu Val Ile Cys Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 40
<211> LENGTH: 1116
<212> TYPE: DNA
<213> ORGANISM: Artificial Sequence
<220> FEATURE:
<223> OTHER INFORMATION: N54V-F58Q-C211M-M213L

<400> SEQUENCE: 40
atgacccaga taagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag tttggacccc gcagatgagc     180
aaagaagctg gtccgcgtca gctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata ctttaagcgt taacgccccg     420
aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtggaa gatcaagaag tggaacctat ccgcggccaa     600
acagtgctga ttaagagcaa ctgtaaacgc atgaccctgg acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcattttaaa acattgtctg     780
cgtttagacc cgagtattag caccgacggc acactggaag catcgaaat tttacgccat     840 aacgttggtc tgcgtcccgc tcgtcgtggt ggtccgcgtg tggaattaga acgcgtgagc     900

```
ttcccgctga agcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg gcgcagcttt agaagttcgt gatctggtgg accaagctat tggtagcagc   1080
agtagtgcca gtagtggccg ttatttagcc aaactg                             1116
```

<210> SEQ ID NO 41
<211> LENGTH: 372
<212> TYPE: PRT
<213> ORGANISM: Artificial Sequence
<220> FEATURE:
<223> OTHER INFORMATION: N54V-F58Q-C211S-M213L

<400> SEQUENCE: 41

```
Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Ser Thr Leu Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320
```

Lys Ala Ser Arg Thr Val Pro Val Val His Ala Tyr Gly Phe Ser Ser
            325                 330                 335

Ala Gly Tyr Gln Gln Gly Trp Gly Ala Ala Leu Glu Val Arg Asp Leu
        340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 42
<211> LENGTH: 1116
<212> TYPE: DNA
<213> ORGANISM: Artificial Sequence
<220> FEATURE:
<223> OTHER INFORMATION: N54V-F58Q-C211S-M213L

<400> SEQUENCE: 42

```
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag tttggacccc gcagatgagc     180
aaagaagctg tccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata cttttaagcgt taacgccccg     420
aagttctgtc agtatctgca gcgcgaagca cagaaactgg gcgtgacctt cgaacgccgt     480
ttagttacct cttttagagca gattgcagat ggcgccgatc tgatcgttaa tgcaaccggt     540
ctgggcgcca aaagcatcgc cggtgtgaa gatcaagaag tggaacctat ccgcggccaa     600
acagtgctga ttaagagcaa ctgtaaacgc tctaccttgg acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcattttaaa acattgtctg     780
cgtttagacc cgagtattag caccgacggc acactggaag gcatcgaaat ttacgccat     840
aacgttggtc tgcgtcccgc tcgtcgtggt ggtccgcgtg tggaattaga acgcgtgagc     900
ttcccgctga agcgcggtca gagtctgtta gctttaggca ccgccaaagc agcagaaggt     960
aaagcaagcc gtaccgtgcc ggttgttcat gcctatggct cagcagcgc cggttaccaa    1020
caaggttggg gcgcagcttt agaagttcgt gatctggtgg accaagctat tggtagcagc    1080
agtagtgcca gtagtggccg ttatttagcc aaactg                              1116
```

<210> SEQ ID NO 43
<211> LENGTH: 372
<212> TYPE: PRT
<213> ORGANISM: Artificial Sequence
<220> FEATURE:
<223> OTHER INFORMATION: N54V-F58Q-C211Y-M213F

<400> SEQUENCE: 43

Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

| | | | | | | | | | | | | |
|---|---|---|---|---|---|---|---|---|---|---|---|---|
|Pro|Trp|Ala|Gly|Ala|Val|Trp|Thr|Pro|Gln|Met|Ser|Lys|Glu|Ala|Gly|
| |50| | | | |55| | | | |60| | | | |

Pro Trp Ala Gly Ala Val Trp Thr Pro Gln Met Ser Lys Glu Ala Gly
    50                        55                      60

Pro Arg Gln Ala Lys Trp Glu Glu Ala Thr Phe Lys Gln Trp Val Asp
65                    70                      75                      80

Phe Val Pro Gln Gly Leu Ala Met Trp Leu Lys Gly Thr Arg Arg Phe
                 85                      90                      95

Ala Glu Thr Glu Ala Asp Leu Leu Gly His Trp Tyr Lys Asp Ile Val
                100                    105                  110

Pro Asn Tyr Arg His Leu Asn Pro Ser Asp Cys Pro Pro Gly Ala Ile
                115                    120                  125

Gly Val Thr Tyr Asp Thr Leu Ser Val Asn Ala Pro Lys Phe Cys Gln
    130                    135                    140

Tyr Leu Gln Arg Glu Ala Gln Lys Leu Gly Val Thr Phe Glu Arg Arg
145                    150                    155                160

Leu Val Thr Ser Leu Glu Gln Ile Ala Asp Gly Ala Asp Leu Ile Val
                165                    170                  175

Asn Ala Thr Gly Leu Gly Ala Lys Ser Ile Ala Gly Val Glu Asp Gln
            180                    185                  190

Glu Val Glu Pro Ile Arg Gly Gln Thr Val Leu Ile Lys Ser Asn Cys
                195                    200                  205

Lys Arg Tyr Thr Phe Asp Ser Ser Asp Pro Lys Ser Pro Ala Tyr Ile
    210                    215                    220

Ile Pro Arg Pro Gly Glu Val Ile Cys Gly Gly Thr Tyr Leu Val
225                    230                    235                240

Gly Asn Tyr Asp Leu Ser Val Asp Pro Ala Thr Ile Pro Arg Ile Leu
                245                    250                  255

Lys His Cys Leu Arg Leu Asp Pro Ser Ile Ser Thr Asp Gly Thr Leu
            260                    265                  270

Glu Gly Ile Glu Ile Leu Arg His Asn Val Gly Leu Arg Pro Ala Arg
                275                    280                  285

Arg Gly Gly Pro Arg Val Glu Leu Glu Arg Val Ser Phe Pro Leu Lys
    290                    295                    300

Arg Gly Gln Ser Leu Leu Ala Leu Gly Thr Ala Lys Ala Ala Glu Gly
305                    310                    315                320

Lys Ala Ser Arg Thr Val Pro Val Val His Ala Tyr Gly Phe Ser Ser
            325                    330                  335

Ala Gly Tyr Gln Gln Gly Trp Gly Ala Ala Leu Glu Val Arg Asp Leu
                340                    345                  350

Val Asp Gln Ala Ile Gly Ser Ser Ser Ala Ser Ser Gly Arg Tyr
            355                    360                  365

Leu Ala Lys Leu
    370

<210> SEQ ID NO 44
<211> LENGTH: 1116
<212> TYPE: DNA
<213> ORGANISM: Artificial Sequence
<220> FEATURE:
<223> OTHER INFORMATION: N54V-F58Q-C211Y-M213F

<400> SEQUENCE: 44

```
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag tttggacccc gcagatgagc     180
```

```
aaagaagctg gtccgcgtca agctaaatgg gaggaagcaa ccttcaaaca gtgggtggac    240
ttcgttccgc aaggtctggc aatgtggctg aaaggtaccc gccgctttgc agaaaccgaa    300
gccgatctgc tgggccattg gtataaggac atcgtgccga attaccgcca tctgaacccg    360
agcgattgtc cgccgggcgc aattggcgtg acctacgata ctttaagcgt taacgccccg    420
aagttctgtc agtatctgca gcgcgaagca cagaaactgg gcgtgacctt cgaacgccgt    480
ttagttacct ctttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc tatacctttg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag gcatcgaaat tttacgccat    840
aacgttggtc tgcgtcccgc tcgtcgtggt ggtccgcgtg tggaattaga acgcgtgagc    900
ttcccgctga gcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg gcgcagcttt agaagttcgt gatctggtgg accaagctat tggtagcagc   1080
agtagtgcca gtagtggccg ttatttagcc aaactg                             1116
```

```
<210> SEQ ID NO 45
<211> LENGTH: 372
<212> TYPE: PRT
<213> ORGANISM: Artificial Sequence
<220> FEATURE:
<223> OTHER INFORMATION: N54V-F58Q-C211S-M213V

<400> SEQUENCE: 45
```

```
Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
```

```
              195                 200                 205
Lys Arg Ser Thr Val Asp Ser Ser Asp Pro Lys Ser Pro Ala Tyr Ile
    210                 215                 220

Ile Pro Arg Pro Gly Gly Glu Val Ile Cys Gly Thr Tyr Leu Val
225                 230                 235                 240

Gly Asn Tyr Asp Leu Ser Val Asp Pro Ala Thr Ile Pro Arg Ile Leu
                    245                 250                 255

Lys His Cys Leu Arg Leu Asp Pro Ser Ile Ser Thr Asp Gly Thr Leu
                260                 265                 270

Glu Gly Ile Glu Ile Leu Arg His Asn Val Gly Leu Arg Pro Ala Arg
            275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
                340                 345                 350

Val Asp Gln Ala Ile Gly Ser Ser Ser Ala Ser Ser Gly Arg Tyr
            355                 360                 365

Leu Ala Lys Leu
    370

<210> SEQ ID NO 46
<211> LENGTH: 1116
<212> TYPE: DNA
<213> ORGANISM: Artificial Sequence
<220> FEATURE:
<223> OTHER INFORMATION: N54V-F58Q-C211S-M213V

<400> SEQUENCE: 46
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag tttggacccc gcagatgagc     180
aaagaagctg gtccgcgtca agctaaatga ggaagcaa ccttcaaaca gtgggtggac       240
ttcgttccgc aaggtctggc aatgtggctg aaaggtaccc gccgctttgc agaaaccgaa    300
gccgatctgc tgggccattg gtataaggac atcgtgccga attaccgcca tctgaacccg    360
agcgattgtc cgccgggcgc aattggcgtg acctacgata ctttaagcgt taacgccccg    420
aagttctgtc agtatctgca gcgcgaagca cagaaactgg gcgtgacctt cgaacgccgt    480
ttagttacct ctttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc tctaccgtgg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag catcgaaat tttacgccat    840 aacgttggtc tgcgtccgc tcgtcgtggt ggtccgcgtg tggaattaga acgcgtgagc    900
ttcccgctga agcgcggtca gagtctgtta gctttaggca ccgccaaagc agcagaaggt    960
aaagcaagcc gtaccgtgcc ggttgttcat gcctatggct tcagcagcgc cggttaccaa   1020
```

```
caaggttggg gcgcagcttt agaagttcgt gatctggtgg accaagctat tggtagcagc      1080
agtagtgcca gtagtggccg ttatttagcc aaactg                                1116
```

<210> SEQ ID NO 47
<211> LENGTH: 372
<212> TYPE: PRT
<213> ORGANISM: Artificial Sequence
<220> FEATURE:
<223> OTHER INFORMATION: N54V-F58Q-C211M-M213T

<400> SEQUENCE: 47

```
Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
            35                  40                  45

Pro Trp Ala Gly Ala Val Trp Thr Pro Gln Met Ser Lys Glu Ala Gly
50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
            115                 120                 125

Gly Val Thr Tyr Asp Thr Leu Ser Val Asn Ala Pro Lys Phe Cys Gln
130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
            195                 200                 205

Lys Arg Met Thr Thr Asp Ser Ser Asp Pro Lys Ser Pro Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
            275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350
```

Val Asp Gln Ala Ile Gly Ser Ser Ser Ala Ser Ser Gly Arg Tyr
        355                 360                 365

Leu Ala Lys Leu
    370

<210> SEQ ID NO 48
<211> LENGTH: 1116
<212> TYPE: DNA
<213> ORGANISM: Artificial Sequence
<220> FEATURE:
<223> OTHER INFORMATION: N54V-F58Q-C211M-M213T

<400> SEQUENCE: 48

| | | |
|---|---|---|
| atgacccaga ataagcgcgt ggttgttctg ggcagtggcg ttattggtct gagctgtgct | 60 |
| ttagctttag cccagaaggg ctataaagtg catgtggttg cccgcgatct gccggaagac | 120 |
| acagtggccc agacctttgc aagcccttgg gccggtgcag tttggacccc gcagatgagc | 180 |
| aaagaagctg gtccgcgtca agctaaatgg gaggaagcaa ccttcaaaca gtgggtggac | 240 |
| ttcgttccgc aaggtctggc aatgtggctg aaaggtaccc gccgctttgc agaaaccgaa | 300 |
| gccgatctgc tgggccattg gtataaggac atcgtgccga attaccgcca tctgaacccg | 360 |
| agcgattgtc cgccgggcgc aattggcgtg acctacgata ctttaagcgt taacgccccg | 420 |
| aagttctgtc agtatctgca gcgcgaagca cagaaactgg gcgtgacctt cgaacgccgt | 480 |
| ttagttacct ctttagagca gattgcagat ggcgccgatc tgatcgttaa tgcaaccggt | 540 |
| ctgggcgcca aaagcatcgc cggtgtggaa gatcaagaag tggaacctat ccgcggccaa | 600 |
| acagtgctga ttaagagcaa ctgtaaacgc atgaccacgg acagtagtga cccgaaaagc | 660 |
| ccggcctaca ttattccgcg cccgggtggt gaagtgatct gtggtggtac ctatttagtg | 720 |
| ggtaactatg atttaagcgt ggatccggcc accattccgc gcattttaaa acattgtctg | 780 |
| cgtttagacc cgagtattag caccgacggc acactggaag catcgaaat tttacgccat | 840 |
| aacgttggtc tgcgtcccgc tcgtcgtggt ggtccgcgtg tggaattaga acgcgtgagc | 900 |
| ttcccgctga gcgcggtca gagtctgtta gctttaggca ccgccaaagc agcagaaggt | 960 |
| aaagcaagcc gtaccgtgcc ggttgttcat gcctatggct tcagcagcgc cggttaccaa | 1020 |
| caaggttggg gcgcagcttt agaagttcgt gatctggtgg accaagctat tggtagcagc | 1080 |
| agtagtgcca gtagtggccg ttatttagcc aaactg | 1116 |

<210> SEQ ID NO 49
<211> LENGTH: 372
<212> TYPE: PRT
<213> ORGANISM: Artificial Sequence
<220> FEATURE:
<223> OTHER INFORMATION: N54V-F58Q-C211G-M213W

<400> SEQUENCE: 49

Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

```
Phe Val Pro Gln Gly Leu Ala Met Trp Leu Lys Gly Thr Arg Arg Phe
                85                  90                  95
Ala Glu Thr Glu Ala Asp Leu Leu Gly His Trp Tyr Lys Asp Ile Val
            100                 105                 110
Pro Asn Tyr Arg His Leu Asn Pro Ser Asp Cys Pro Pro Gly Ala Ile
        115                 120                 125
Gly Val Thr Tyr Asp Thr Leu Ser Val Asn Ala Pro Lys Phe Cys Gln
    130                 135                 140
Tyr Leu Gln Arg Glu Ala Gln Lys Leu Gly Val Thr Phe Glu Arg Arg
145                 150                 155                 160
Leu Val Thr Ser Leu Glu Gln Ile Ala Asp Gly Ala Asp Leu Ile Val
                165                 170                 175
Asn Ala Thr Gly Leu Gly Ala Lys Ser Ile Ala Gly Val Glu Asp Gln
            180                 185                 190
Glu Val Glu Pro Ile Arg Gly Gln Thr Val Leu Ile Lys Ser Asn Cys
        195                 200                 205
Lys Arg Gly Thr Trp Asp Ser Ser Asp Pro Lys Ser Pro Ala Tyr Ile
    210                 215                 220
Ile Pro Arg Pro Gly Gly Glu Val Ile Cys Gly Gly Thr Tyr Leu Val
225                 230                 235                 240
Gly Asn Tyr Asp Leu Ser Val Asp Pro Ala Thr Ile Pro Arg Ile Leu
                245                 250                 255
Lys His Cys Leu Arg Leu Asp Pro Ser Ile Ser Thr Asp Gly Thr Leu
            260                 265                 270
Glu Gly Ile Glu Ile Leu Arg His Asn Val Gly Leu Arg Pro Ala Arg
        275                 280                 285
Arg Gly Gly Pro Arg Val Glu Leu Glu Arg Val Ser Phe Pro Leu Lys
    290                 295                 300
Arg Gly Gln Ser Leu Leu Ala Leu Gly Thr Ala Lys Ala Ala Glu Gly
305                 310                 315                 320
Lys Ala Ser Arg Thr Val Pro Val Val His Ala Tyr Gly Phe Ser Ser
                325                 330                 335
Ala Gly Tyr Gln Gln Gly Trp Gly Ala Ala Leu Glu Val Arg Asp Leu
            340                 345                 350
Val Asp Gln Ala Ile Gly Ser Ser Ser Ser Ala Ser Ser Gly Arg Tyr
        355                 360                 365
Leu Ala Lys Leu
    370

<210> SEQ ID NO 50
<211> LENGTH: 1116
<212> TYPE: DNA
<213> ORGANISM: Artificial Sequence
<220> FEATURE:
<223> OTHER INFORMATION: N54V-F58Q-C211G-M213W

<400> SEQUENCE: 50
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag tttggacccc gcagatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
```

```
agcgattgtc cgccgggcgc aattggcgtg acctacgata ctttaagcgt taacgccccg    420
aagttctgtc agtatctgca gcgcgaagca cagaaactgg gcgtgacctt cgaacgccgt    480
ttagttacct ctttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc gggacctggg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag gcatcgaaat tttacgccat    840
aacgttggtc tgcgtcccgc tcgtcgtggt ggtccgcgtg tggaattaga acgcgtgagc    900
ttcccgctga agcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg gcgcagcttt agaagttcgt gatctggtgg accaagctat tggtagcagc   1080
agtagtgcca gtagtggccg ttatttagcc aaactg                             1116
```

<210> SEQ ID NO 51
<211> LENGTH: 372
<212> TYPE: PRT
<213> ORGANISM: Artificial Sequence
<220> FEATURE:
<223> OTHER INFORMATION: N54V-F58Q-C211A-M213A

<400> SEQUENCE: 51

```
Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Val Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Ala Thr Ala Asp Ser Ser Asp Pro Lys Ser Pro Ala Tyr Ile
    210                 215                 220
```

| | | | | | | | | | | | | | | |
|---|---|---|---|---|---|---|---|---|---|---|---|---|---|---|
|Ile|Pro|Arg|Pro|Gly|Gly|Glu|Val|Ile|Cys|Gly|Thr|Tyr|Leu|Val|
|225| | | | |230| | | | |235| | | |240|

Gly Asn Tyr Asp Leu Ser Val Asp Pro Ala Thr Ile Pro Arg Ile Leu
            245                 250                 255

Lys His Cys Leu Arg Leu Asp Pro Ser Ile Ser Thr Asp Gly Thr Leu
        260                 265                 270

Glu Gly Ile Glu Ile Leu Arg His Asn Val Gly Leu Arg Pro Ala Arg
    275                 280                 285

Arg Gly Gly Pro Arg Val Glu Leu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ser Ala Ser Ser Gly Arg Tyr
        355                 360                 365

Leu Ala Lys Leu
    370

<210> SEQ ID NO 52
<211> LENGTH: 1116
<212> TYPE: DNA
<213> ORGANISM: Artificial Sequence
<220> FEATURE:
<223> OTHER INFORMATION: N54V-F58Q-C211A-M213A

<400> SEQUENCE: 52

```
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag tttggacccc gcagatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata cttttaagcg taacgccccg     420
aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtggaa gatcaagaag tggaacctat ccgcggccaa     600
acagtgctga ttaagagcaa ctgtaaacgc gcgaccgctg acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcattttaaa acattgtctg     780
cgtttagacc cgagtattag caccgacggc acactggaag gcatcgaaat tttacgccat     840
aacgttggtc tgcgtccgc tcgtcgtggt ggtccgcgtg tggaattaga acgcgtgagc     900
ttcccgctga gcgcggtca gagtctgtta gctttaggca ccgccaaagc agcagaaggt     960
aaagcaagcc gtaccgtgcc ggttgttcat gcctatggct tcagcagcgc cggttaccaa    1020
caaggttggg gcgcagcttt agaagttcgt gatctggtgg accaagctat tggtagcagc    1080
agtagtgcca gtagtggccg ttatttagcc aaactg                               1116
```

```
<210> SEQ ID NO 53
<211> LENGTH: 372
<212> TYPE: PRT
<213> ORGANISM: Artificial Sequence
<220> FEATURE:
<223> OTHER INFORMATION: N54V-F58Q-C211A-M213V

<400> SEQUENCE: 53
```

| Met<br>1 | Thr | Gln | Asn | Lys<br>5 | Arg | Val | Val | Leu | Gly<br>10 | Ser | Gly | Val | Ile | Gly<br>15 |
|---|---|---|---|---|---|---|---|---|---|---|---|---|---|---|
| Leu | Ser | Cys | Ala<br>20 | Leu | Ala | Leu | Ala | Gln<br>25 | Lys | Gly | Tyr | Lys | Val<br>30 | His | Val |
| Val | Ala | Arg<br>35 | Asp | Leu | Pro | Glu | Asp<br>40 | Thr | Val | Ala | Gln | Thr<br>45 | Phe | Ala | Ser |
| Pro | Trp<br>50 | Ala | Gly | Ala | Val | Trp<br>55 | Thr | Pro | Gln | Met | Ser<br>60 | Lys | Glu | Ala | Gly |
| Pro<br>65 | Arg | Gln | Ala | Lys | Trp<br>70 | Glu | Glu | Ala | Thr | Phe<br>75 | Lys | Gln | Trp | Val | Asp<br>80 |
| Phe | Val | Pro | Gln | Gly<br>85 | Leu | Ala | Met | Trp | Leu<br>90 | Lys | Gly | Thr | Arg | Arg<br>95 | Phe |
| Ala | Glu | Thr | Glu<br>100 | Ala | Asp | Leu | Leu | Gly<br>105 | His | Trp | Tyr | Lys | Asp<br>110 | Ile | Val |
| Pro | Asn | Tyr<br>115 | Arg | His | Leu | Asn | Pro<br>120 | Ser | Asp | Cys | Pro | Pro<br>125 | Gly | Ala | Ile |
| Gly | Val<br>130 | Thr | Tyr | Asp | Thr | Leu<br>135 | Ser | Val | Asn | Ala | Pro<br>140 | Lys | Phe | Cys | Gln |
| Tyr<br>145 | Leu | Gln | Arg | Glu | Ala<br>150 | Gln | Lys | Leu | Gly | Val<br>155 | Thr | Phe | Glu | Arg | Arg<br>160 |
| Leu | Val | Thr | Ser | Leu<br>165 | Glu | Gln | Ile | Ala | Asp<br>170 | Gly | Ala | Asp | Leu | Ile<br>175 | Val |
| Asn | Ala | Thr | Gly<br>180 | Leu | Gly | Ala | Lys | Ser<br>185 | Ile | Ala | Gly | Val | Glu<br>190 | Asp | Gln |
| Glu | Val<br>195 | Glu | Pro | Ile | Arg | Gly<br>200 | Gln | Thr | Val | Leu | Ile<br>205 | Lys | Ser | Asn | Cys |
| Lys<br>210 | Arg | Ala | Thr | Val | Asp<br>215 | Ser | Ser | Asp | Pro | Lys<br>220 | Ser | Pro | Ala | Tyr | Ile |
| Ile<br>225 | Pro | Arg | Pro | Gly | Gly<br>230 | Glu | Val | Ile | Cys | Gly<br>235 | Gly | Thr | Tyr | Leu | Val<br>240 |
| Gly | Asn | Tyr | Asp | Leu<br>245 | Ser | Val | Asp | Pro | Ala<br>250 | Thr | Ile | Pro | Arg | Ile<br>255 | Leu |
| Lys | His | Cys | Leu<br>260 | Arg | Leu | Asp | Pro | Ser<br>265 | Ile | Ser | Thr | Asp | Gly<br>270 | Thr | Leu |
| Glu | Gly | Ile<br>275 | Glu | Ile | Leu | Arg | His<br>280 | Asn | Val | Gly | Leu | Arg<br>285 | Pro | Ala | Arg |
| Arg | Gly<br>290 | Gly | Pro | Arg | Val | Glu<br>295 | Leu | Glu | Arg | Val | Ser<br>300 | Phe | Pro | Leu | Lys |
| Arg<br>305 | Gly | Gln | Ser | Leu | Leu<br>310 | Ala | Leu | Gly | Thr | Ala<br>315 | Lys | Ala | Ala | Glu | Gly<br>320 |
| Lys | Ala | Ser | Arg | Thr<br>325 | Val | Pro | Val | Val | His<br>330 | Ala | Tyr | Gly | Phe | Ser<br>335 | Ser |
| Ala | Gly | Tyr | Gln<br>340 | Gln | Gly | Trp | Gly | Ala<br>345 | Ala | Leu | Glu | Val | Arg<br>350 | Asp | Leu |
| Val | Asp | Gln | Ala | Ile<br>355 | Gly | Ser | Ser | Ser | Ala<br>360 | Ser | Ser | Gly | Arg<br>365 | Tyr |
| Leu | Ala | Lys | Leu | | | | | | | | | | | |

<210> SEQ ID NO 54
<211> LENGTH: 1116
<212> TYPE: DNA
<213> ORGANISM: Artificial Sequence
<220> FEATURE:
<223> OTHER INFORMATION: N54V-F58Q-C211A-M213V

<400> SEQUENCE: 54

```
atgacccaga ataagcgcgt ggttgttctg ggcagtggcg ttattggtct gagctgtgct        60
ttagctttag cccagaaggg ctataaagtg catgtggttg cccgcgatct gccggaagac       120
acagtggccc agacctttgc aagcccttgg gccggtgcag tttggacccc gcagatgagc       180
aaagaagctg gtccgcgtca agctaaatgg gaggaagcaa ccttcaaaca gtgggtggac       240
ttcgttccgc aaggtctggc aatgtggctg aaaggtaccc gccgctttgc agaaaccgaa       300
gccgatctgc tgggccattg gtataaggac atcgtgccga attaccgcca tctgaacccg       360
agcgattgtc cgccgggcgc aattggcgtg acctacgata cttttaagcg taacgccccg       420
aagttctgtc agtatctgca gcgcgaagca cagaaactgg gcgtgacctt cgaacgccgt       480
ttagttacct ctttagagca gattgcagat ggcgccgatc tgatcgttaa tgcaaccggt       540
ctgggcgcca aaagcatcgc cggtgtggaa gatcaagaag tggaacctat ccgcggccaa       600
acagtgctga ttaagagcaa ctgtaaacgc gcgaccgtgg acagtagtga cccgaaaagc       660
ccggcctaca ttattccgcg cccgggtggt gaagtgatct gtggtggtac ctatttagtg       720
ggtaactatg atttaagcgt ggatccggcc accattccgc gcattttaaa acattgtctg       780
cgtttagacc cgagtattag caccgacggc acactggaag gcatcgaaat tttacgccat       840
aacgttggtc tgcgtcccgc tcgtcgtggt ggtccgcgtg tggaattaga acgcgtgagc       900
ttcccgctga gcgcggtca gagtctgtta gctttaggca ccgccaaagc agcagaaggt       960
aaagcaagcc gtaccgtgcc ggttgttcat gcctatggct tcagcagcgc cggttaccaa      1020
caaggttggg gcgcagcttt agaagttcgt gatctggtgg accaagctat tggtagcagc      1080
agtagtgcca gtagtggccg ttatttagcc aaactg                                1116
```

<210> SEQ ID NO 55
<211> LENGTH: 372
<212> TYPE: PRT
<213> ORGANISM: Artificial Sequence
<220> FEATURE:
<223> OTHER INFORMATION: N54C- T56T- F58G-C211L-M213T

<400> SEQUENCE: 55

```
Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Cys Trp Thr Pro Gly Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
```

```
                100                 105                 110
Pro Asn Tyr Arg His Leu Asn Pro Ser Asp Cys Pro Pro Gly Ala Ile
            115                 120                 125

Gly Val Thr Tyr Asp Thr Leu Ser Val Asn Ala Pro Lys Phe Cys Gln
        130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Leu Thr Thr Asp Ser Ser Asp Pro Lys Ser Pro Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 56
<211> LENGTH: 1116
<212> TYPE: DNA
<213> ORGANISM: Artificial Sequence
<220> FEATURE:
<223> OTHER INFORMATION: N54C- T56T- F58G-C211L-M213T

<400> SEQUENCE: 56
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcat gttggacccc ggggatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata cttttaagcg taacgccccg     420
aagttctgtc agtatctgca gcgcgaagca cagaaactgg gcgtgacctt cgaacgccgt     480
```

-continued

```
ttagttacct ctttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc ctgaccactg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag gcatcgaaat tttacgccat    840
aacgttggtc tgcgtcccgc tcgtcgtggt ggtccgcgtg tggaattaga acgcgtgagc    900
ttcccgctga agcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg cgcagctttt agaagttcgt gatctggtgg accaagctat tggtagcagc   1080
agtagtgcca gtagtggccg ttatttagcc aaactg                             1116
```

<210> SEQ ID NO 57
<211> LENGTH: 372
<212> TYPE: PRT
<213> ORGANISM: Artificial Sequence
<220> FEATURE:
<223> OTHER INFORMATION: N54S- T56T- F58H-C211L-M213T

<400> SEQUENCE: 57

```
Met Thr Gln Asn Lys Arg Val Val Leu Gly Ser Gly Val Ile Gly
1               5                  10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Ser Trp Thr Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Leu Thr Thr Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255
```

Lys His Cys Leu Arg Leu Asp Pro Ser Ile Ser Thr Asp Gly Thr Leu
                260                 265                 270

Glu Gly Ile Glu Ile Leu Arg His Asn Val Gly Leu Arg Pro Ala Arg
            275                 280                 285

Arg Gly Gly Pro Arg Val Glu Leu Glu Arg Val Ser Phe Pro Leu Lys
        290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ser Ala Ser Ser Gly Arg Tyr
        355                 360                 365

Leu Ala Lys Leu
    370

<210> SEQ ID NO 58
<211> LENGTH: 1116
<212> TYPE: DNA
<213> ORGANISM: Artificial Sequence
<220> FEATURE:
<223> OTHER INFORMATION: N54S- T56T- F58H-C211L-M213T

<400> SEQUENCE: 58

```
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcaa gttggacccc gcatatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc gccgggcgc aattggcgtg acctacgata ctttaagcgt taacgccccg     420
aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtgaa gatcaagaag tggaacctat ccgcggccaa     600
acagtgctga ttaagagcaa ctgtaaacgc ctgaccactg acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcattttaaa acattgtctg     780
cgtttagacc cgagtattag caccgacggc acactggaag catcgaaat tttacgccat     840
aacgttggtc tgcgtcccgc tcgtcgtggt ggtccgcgtg tggaattaga acgcgtgagc     900
ttcccgctga gcgcggtca gagtctgtta gctttaggca ccgccaaagc agcagaaggt     960
aaagcaagcc gtaccgtgcc ggttgttcat gcctatggct cagcagcgc cggttaccaa    1020
caaggttggg gcgcagcttt agaagttcgt gatctggtgg accaagctat tggtagcagc    1080
agtagtgcca gtagtggccg ttatttagcc aaactg                              1116
```

<210> SEQ ID NO 59
<211> LENGTH: 372
<212> TYPE: PRT
<213> ORGANISM: Artificial Sequence
<220> FEATURE:

<223> OTHER INFORMATION: N54G- T56T- F58K-C211L-M213T

<400> SEQUENCE: 59

```
Met Thr Gln Asn Lys Arg Val Val Val Leu Gly Ser Gly Val Ile Gly
1               5                   10                  15
Leu Ser Cys Ala Leu Ala Leu Ala Gln Lys Gly Tyr Lys Val His Val
            20                  25                  30
Val Ala Arg Asp Leu Pro Glu Asp Thr Val Ala Gln Thr Phe Ala Ser
        35                  40                  45
Pro Trp Ala Gly Ala Gly Trp Thr Pro Lys Met Ser Lys Glu Ala Gly
    50                  55                  60
Pro Arg Gln Ala Lys Trp Glu Glu Ala Thr Phe Lys Gln Trp Val Asp
65                  70                  75                  80
Phe Val Pro Gln Gly Leu Ala Met Trp Leu Lys Gly Thr Arg Arg Phe
                85                  90                  95
Ala Glu Thr Glu Ala Asp Leu Leu Gly His Trp Tyr Lys Asp Ile Val
            100                 105                 110
Pro Asn Tyr Arg His Leu Asn Pro Ser Asp Cys Pro Pro Gly Ala Ile
        115                 120                 125
Gly Val Thr Tyr Asp Thr Leu Ser Val Asn Ala Pro Lys Phe Cys Gln
    130                 135                 140
Tyr Leu Gln Arg Glu Ala Gln Lys Leu Gly Val Thr Phe Glu Arg Arg
145                 150                 155                 160
Leu Val Thr Ser Leu Glu Gln Ile Ala Asp Gly Ala Asp Leu Ile Val
                165                 170                 175
Asn Ala Thr Gly Leu Gly Ala Lys Ser Ile Ala Gly Val Glu Asp Gln
            180                 185                 190
Glu Val Glu Pro Ile Arg Gly Gln Thr Val Leu Ile Lys Ser Asn Cys
        195                 200                 205
Lys Arg Leu Thr Thr Asp Ser Ser Asp Pro Lys Ser Pro Ala Tyr Ile
    210                 215                 220
Ile Pro Arg Pro Gly Gly Glu Val Ile Cys Gly Gly Thr Tyr Leu Val
225                 230                 235                 240
Gly Asn Tyr Asp Leu Ser Val Asp Pro Ala Thr Ile Pro Arg Ile Leu
                245                 250                 255
Lys His Cys Leu Arg Leu Asp Pro Ser Ile Ser Thr Asp Gly Thr Leu
            260                 265                 270
Glu Gly Ile Glu Ile Leu Arg His Asn Val Gly Leu Arg Pro Ala Arg
        275                 280                 285
Arg Gly Gly Pro Arg Val Glu Leu Glu Arg Val Ser Phe Pro Leu Lys
    290                 295                 300
Arg Gly Gln Ser Leu Leu Ala Leu Gly Thr Ala Lys Ala Ala Glu Gly
305                 310                 315                 320
Lys Ala Ser Arg Thr Val Pro Val Val His Ala Tyr Gly Phe Ser Ser
                325                 330                 335
Ala Gly Tyr Gln Gln Gly Trp Gly Ala Ala Leu Glu Val Arg Asp Leu
            340                 345                 350
Val Asp Gln Ala Ile Gly Ser Ser Ser Ser Ala Ser Ser Gly Arg Tyr
        355                 360                 365
Leu Ala Lys Leu
    370
```

<210> SEQ ID NO 60
<211> LENGTH: 1116

<212> TYPE: DNA
<213> ORGANISM: Artificial Sequence
<220> FEATURE:
<223> OTHER INFORMATION: N54G- T56T- F58K-C211L-M213T

<400> SEQUENCE: 60

```
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag ggtggacccc gaagatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata cttaagcgt taacgccccg      420
aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtggaa gatcaagaag tggaacctat ccgcggccaa     600
acagtgctga ttaagagcaa ctgtaaacgc ctgaccactg acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcattttaaa acattgtctg     780
cgtttagacc cgagtattag caccgacggc acactggaag gcatcgaaat tttacgccat     840
aacgttggtc tgcgtcccgc tcgtcgtggt ggtccgcgtg tggaattaga acgcgtgagc     900
ttcccgctga gcgcggtca gagtctgtta gctttaggca ccgccaaagc agcagaaggt     960
aaagcaagcc gtaccgtgcc ggttgttcat gcctatggct tcagcagcgc cggttaccaa    1020
caaggttggg gcgcagcttt agaagttcgt gatctggtgg accaagctat tggtagcagc    1080
agtagtgcca gtagtggccg ttatttagcc aaactg                              1116
```

<210> SEQ ID NO 61
<211> LENGTH: 372
<212> TYPE: PRT
<213> ORGANISM: Artificial Sequence
<220> FEATURE:
<223> OTHER INFORMATION: N54A- T56T- F58H-C211L-M213T

<400> SEQUENCE: 61

```
Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Ala Trp Thr Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125
```

Gly Val Thr Tyr Asp Thr Leu Ser Val Asn Ala Pro Lys Phe Cys Gln
        130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
            165                 170                 175

Asn Ala Thr Gly Leu Gly Ala Lys Ser Ile Ala Gly Val Glu Asp Gln
        180                 185                 190

Glu Val Glu Pro Ile Arg Gly Gln Thr Val Leu Ile Lys Ser Asn Cys
    195                 200                 205

Lys Arg Leu Thr Thr Asp Ser Ser Asp Pro Lys Ser Pro Ala Tyr Ile
210                 215                 220

Ile Pro Arg Pro Gly Gly Glu Val Ile Cys Gly Thr Tyr Leu Val
225                 230                 235                 240

Gly Asn Tyr Asp Leu Ser Val Asp Pro Ala Thr Ile Pro Arg Ile Leu
            245                 250                 255

Lys His Cys Leu Arg Leu Asp Pro Ser Ile Ser Thr Asp Gly Thr Leu
        260                 265                 270

Glu Gly Ile Glu Ile Leu Arg His Asn Val Gly Leu Arg Pro Ala Arg
    275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
            325                 330                 335

Ala Gly Tyr Gln Gln Gly Trp Gly Ala Ala Leu Glu Val Arg Asp Leu
        340                 345                 350

Val Asp Gln Ala Ile Gly Ser Ser Ser Ala Ser Ser Gly Arg Tyr
    355                 360                 365

Leu Ala Lys Leu
    370

<210> SEQ ID NO 62
<211> LENGTH: 1116
<212> TYPE: DNA
<213> ORGANISM: Artificial Sequence
<220> FEATURE:
<223> OTHER INFORMATION: N54A- T56T- F58H-C211L-M213T

<400> SEQUENCE: 62
atgacccaga ataagcgcgt ggttgttctg ggcagtggcg ttattggtct gagctgtgct      60
ttagctttag cccagaaggg ctataaagtg catgtggttg cccgcgatct gccggaagac    120
acagtggccc agacctttgc aagcccttgg gccggtgcag cttggacccc gcatatgagc    180
aaagaagctg gtccgcgtca agctaaatgg gaggaagcaa ccttcaaaca gtgggtggac    240
ttcgttccgc aaggtctggc aatgtggctg aaaggtaccc gccgctttgc agaaaccgaa    300
gccgatctgc tgggccattg gtataaggac atcgtgccga attaccgcca tctgaacccg    360
agcgattgtc cgccgggcgc aattggcgtg acctacgata cttttaagcg taacgccccg    420
aagttctgtc agtatctgca gcgcgaagca cagaaactgg gcgtgacctt cgaacgccgt    480
ttagttacct ctttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc ctgaccactg acagtagtga cccgaaaagc    660

```
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag gcatcgaaat tttacgccat    840
aacgttggtc tgcgtcccgc tcgtcgtggt ggtccgcgtg tggaattaga acgcgtgagc    900
ttcccgctga agcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg gcgcagcttt agaagttcgt gatctggtgg accaagctat tggtagcagc   1080
agtagtgcca gtagtggccg ttatttagcc aaactg                             1116
```

<210> SEQ ID NO 63
<211> LENGTH: 372
<212> TYPE: PRT
<213> ORGANISM: Artificial Sequence
<220> FEATURE:
<223> OTHER INFORMATION: N54A- T56T- F58K-C211L-M213T

<400> SEQUENCE: 63

```
Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
                20                  25                  30

Val Ala Arg Asp Leu Pro Glu Asp Thr Val Ala Gln Thr Phe Ala Ser
            35                  40                  45

Pro Trp Ala Gly Ala Ala Trp Thr Pro Lys Met Ser Lys Glu Ala Gly
50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Leu Thr Thr Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
```

```
            275                 280                 285
Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
                355                 360                 365

Leu Ala Lys Leu
    370
```

<210> SEQ ID NO 64
<211> LENGTH: 1116
<212> TYPE: DNA
<213> ORGANISM: Artificial Sequence
<220> FEATURE:
<223> OTHER INFORMATION: N54A- T56T- F58K-C211L-M213T

<400> SEQUENCE: 64

```
atgacccaga ataagcgcgt ggttgttctg ggcagtggcg ttattggtct gagctgtgct      60
ttagctttag cccagaaggg ctataaagtg catgtggttg cccgcgatct gccgaagac     120
acagtggccc agacctttgc aagcccttgg gccggtgcag cgtggacccc gaagatgagc    180
aaagaagctg tccgcgtca agctaaatgg gaggaagcaa ccttcaaaca gtgggtggac     240
ttcgttccgc aaggtctggc aatgtggctg aaaggtaccc gccgctttgc agaaaccgaa    300
gccgatctgc tgggccattg gtataaggac atcgtgccga attaccgcca tctgaacccg    360
agcgattgtc cgccgggcgc aattggcgtg acctacgata cttttaagcg taacgccccg    420
aagttctgtc agtatctgca gcgcgaagca cagaaactgg gcgtgacctt cgaacgccgt    480
ttagttacct cttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc ctgaccactg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag catcgaaat tttacgccat    840
aacgttggtc tgcgtccgc tcgtcgtggt ggtccgcgtg tggaattaga acgcgtgagc    900
ttcccgctga gcgcggtca gagtctgtta gctttaggca ccgccaaagc agcagaaggt    960
aaagcaagcc gtaccgtgcc ggttgttcat gcctatggct cagcagcgc cggttaccaa   1020
caaggttggg gcgcagcttt agaagttcgt gatctggtgg accaagctat tggtagcagc   1080
agtagtgcca gtagtggccg ttatttagcc aaactg                              1116
```

<210> SEQ ID NO 65
<211> LENGTH: 372
<212> TYPE: PRT
<213> ORGANISM: Artificial Sequence
<220> FEATURE:
<223> OTHER INFORMATION: N54C- T56T- F58A-C211L-M213T

<400> SEQUENCE: 65

Met Thr Gln Asn Lys Arg Val Val Val Leu Gly Ser Gly Val Ile Gly

```
1               5                   10                  15
Leu Ser Cys Ala Leu Ala Leu Ala Gln Lys Gly Tyr Lys Val His Val
                20                  25                  30
Val Ala Arg Asp Leu Pro Glu Asp Thr Val Gln Thr Phe Ala Ser
                35                  40                  45
Pro Trp Ala Gly Ala Cys Trp Thr Pro Ala Met Ser Lys Glu Ala Gly
 50                  55                  60
Pro Arg Gln Ala Lys Trp Glu Glu Ala Thr Phe Lys Gln Trp Val Asp
 65                  70                  75                  80
Phe Val Pro Gln Gly Leu Ala Met Trp Leu Lys Gly Thr Arg Arg Phe
                85                  90                  95
Ala Glu Thr Glu Ala Asp Leu Leu Gly His Trp Tyr Lys Asp Ile Val
                100                 105                 110
Pro Asn Tyr Arg His Leu Asn Pro Ser Asp Cys Pro Pro Gly Ala Ile
                115                 120                 125
Gly Val Thr Tyr Asp Thr Leu Ser Val Asn Ala Pro Lys Phe Cys Gln
 130                 135                 140
Tyr Leu Gln Arg Glu Ala Gln Lys Leu Gly Val Thr Phe Glu Arg Arg
 145                 150                 155                 160
Leu Val Thr Ser Leu Glu Gln Ile Ala Asp Gly Ala Asp Leu Ile Val
                165                 170                 175
Asn Ala Thr Gly Leu Gly Ala Lys Ser Ile Ala Gly Val Glu Asp Gln
                180                 185                 190
Glu Val Glu Pro Ile Arg Gly Gln Thr Val Leu Ile Lys Ser Asn Cys
                195                 200                 205
Lys Arg Leu Thr Thr Asp Ser Ser Asp Pro Lys Ser Pro Ala Tyr Ile
 210                 215                 220
Ile Pro Arg Pro Gly Gly Glu Val Ile Cys Gly Gly Thr Tyr Leu Val
 225                 230                 235                 240
Gly Asn Tyr Asp Leu Ser Val Asp Pro Ala Thr Ile Pro Arg Ile Leu
                245                 250                 255
Lys His Cys Leu Arg Leu Asp Pro Ser Ile Ser Thr Asp Gly Thr Leu
                260                 265                 270
Glu Gly Ile Glu Ile Leu Arg His Asn Val Gly Leu Arg Pro Ala Arg
                275                 280                 285
Arg Gly Gly Pro Arg Val Glu Leu Glu Arg Val Ser Phe Pro Leu Lys
 290                 295                 300
Arg Gly Gln Ser Leu Leu Ala Leu Gly Thr Ala Lys Ala Ala Glu Gly
 305                 310                 315                 320
Lys Ala Ser Arg Thr Val Pro Val Val His Ala Tyr Gly Phe Ser Ser
                325                 330                 335
Ala Gly Tyr Gln Gln Gly Trp Gly Ala Ala Leu Glu Val Arg Asp Leu
                340                 345                 350
Val Asp Gln Ala Ile Gly Ser Ser Ser Ala Ser Ser Gly Arg Tyr
                355                 360                 365
Leu Ala Lys Leu
                370

<210> SEQ ID NO 66
<211> LENGTH: 1116
<212> TYPE: DNA
<213> ORGANISM: Artificial Sequence
<220> FEATURE:
<223> OTHER INFORMATION: N54C- T56T- F58A-C211L-M213T
```

<400> SEQUENCE: 66

```
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcat gttggacccc ggcgatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata cttttaagcg taacgccccg     420
aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtggaa gatcaagaag tggaacctat ccgcggccaa     600
acagtgctga ttaagagcaa ctgtaaacgc ctgaccactg acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcattttaaa acattgtctg     780
cgtttagacc cgagtattag caccgacggc acactggaag gcatcgaaat tttacgccat     840
aacgttggtc tgcgtcccgc tcgtcgtggt ggtccgcgtg tggaattaga acgcgtgagc     900
ttcccgctga gcgcggtca gagtctgtta gctttaggca ccgccaaagc agcagaaggt     960
aaagcaagcc gtaccgtgcc ggttgttcat gcctatggct tcagcagcgc cggttaccaa    1020
caaggttggg gcgcagcttt agaagttcgt gatctggtgg accaagctat tggtagcagc    1080
agtagtgcca gtagtggccg ttatttagcc aaactg                              1116
```

<210> SEQ ID NO 67
<211> LENGTH: 1116
<212> TYPE: DNA
<213> ORGANISM: Artificial Sequence
<220> FEATURE:
<223> OTHER INFORMATION: N54A- T56T- F58H-C211L-M213T

<400> SEQUENCE: 67

```
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag cttggacccc gcatatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata cttttaagcg taacgccccg     420
aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtggaa gatcaagaag tggaacctat ccgcggccaa     600
acagtgctga ttaagagcaa ctgtaaacgc ctgaccactg acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcattttaaa acattgtctg     780
cgtttagacc cgagtattag caccgacggc acactggaag gcatcgaaat tttacgccat     840
aacgttggtc tgcgtcccgc tcgtcgtggt ggtccgcgtg tggaattaga acgcgtgagc     900
```

```
ttcccgctga agcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg gcgcagcttt agaagttcgt gatctggtgg accaagctat tggtagcagc   1080
agtagtgcca gtagtggccg ttatttagcc aaactg                             1116
```

<210> SEQ ID NO 68
<211> LENGTH: 372
<212> TYPE: PRT
<213> ORGANISM: Artificial Sequence
<220> FEATURE:
<223> OTHER INFORMATION: N54G- T56T- F58A-C211L-M213T

<400> SEQUENCE: 68

```
Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Gly Trp Thr Pro Ala Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Leu Thr Thr Asp Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320
```

```
Lys Ala Ser Arg Thr Val Pro Val Val His Ala Tyr Gly Phe Ser Ser
            325                 330                 335

Ala Gly Tyr Gln Gln Gly Trp Gly Ala Ala Leu Glu Val Arg Asp Leu
        340                 345                 350

Val Asp Gln Ala Ile Gly Ser Ser Ser Ala Ser Ser Gly Arg Tyr
    355                 360                 365

Leu Ala Lys Leu
    370

<210> SEQ ID NO 69
<211> LENGTH: 1116
<212> TYPE: DNA
<213> ORGANISM: Artificial Sequence
<220> FEATURE:
<223> OTHER INFORMATION: N54G- T56T- F58A-C211L-M213T

<400> SEQUENCE: 69
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag gtggaccccg gctatgagc      180 aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata ctttaagcgt taacgccccg     420
aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtggaa gatcaagaag tggaacctat ccgcggccaa     600
acagtgctga ttaagagcaa ctgtaaacgc ctgaccactg acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcattttaaa acattgtctg     780
cgtttagacc cgagtattag caccgacggc acactggaag catcgaaat tttacgccat     840 aacgttggtc tgcgtcccgc tcgtcgtggt ggtccgcgtg tggaattaga acgcgtgagc     900
ttcccgctga gcgcggtca gagtctgtta gctttaggca ccgccaaagc agcagaaggt     960
aaagcaagcc gtaccgtgcc ggttgttcat gcctatggct cagcagcgc cggttaccaa    1020 caaggttggg gcgcagcttt agaagttcgt gatctggtgg accaagctat tggtagcagc    1080
agtagtgcca gtagtggccg ttatttagcc aaactg                              1116

<210> SEQ ID NO 70
<211> LENGTH: 372
<212> TYPE: PRT
<213> ORGANISM: Artificial Sequence
<220> FEATURE:
<223> OTHER INFORMATION: N54V- T56T- F58H-C211L-M213T

<400> SEQUENCE: 70

Met Thr Gln Asn Lys Arg Val Val Val Leu Gly Ser Gly Val Ile Gly
1               5                  10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45
```

Pro Trp Ala Gly Ala Val Trp Thr Pro His Met Ser Lys Glu Ala Gly
    50                  55                  60

Pro Arg Gln Ala Lys Trp Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Gly Ala Ile
        115                 120                 125

Gly Val Thr Tyr Asp Thr Leu Ser Val Asn Ala Pro Lys Phe Cys Gln
130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Leu Thr Thr Asp Ser Ser Asp Pro Lys Ser Pro Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 71
<211> LENGTH: 1116
<212> TYPE: DNA
<213> ORGANISM: Artificial Sequence
<220> FEATURE:
<223> OTHER INFORMATION: N54V- T56T- F58H-C211L-M213T

<400> SEQUENCE: 71
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag tttggacccc gcatatgagc     180

| | |
|---|---|
| aaagaagctg gtccgcgtca agctaaatgg gaggaagcaa ccttcaaaca gtgggtggac | 240 |
| ttcgttccgc aaggtctggc aatgtggctg aaaggtaccc gccgctttgc agaaaccgaa | 300 |
| gccgatctgc tgggccattg gtataaggac atcgtgccga attaccgcca tctgaacccg | 360 |
| agcgattgtc cgccgggcgc aattggcgtg acctacgata ctttaagcgt taacgccccg | 420 |
| aagttctgtc agtatctgca gcgcgaagca cagaaactgg gcgtgacctt cgaacgccgt | 480 |
| ttagttacct ctttagagca gattgcagat ggcgccgatc tgatcgttaa tgcaaccggt | 540 |
| ctgggcgcca aaagcatcgc cggtgtggaa gatcaagaag tggaacctat ccgcggccaa | 600 |
| acagtgctga ttaagagcaa ctgtaaacgc ctgaccactg acagtagtga cccgaaaagc | 660 |
| ccggcctaca ttattccgcg cccgggtggt gaagtgatct gtggtggtac ctatttagtg | 720 |
| ggtaactatg atttaagcgt ggatccggcc accattccgc gcattttaaa acattgtctg | 780 |
| cgtttagacc cgagtattag caccgacggc acactggaag catcgaaat tttacgccat | 840 |
| aacgttggtc tgcgtcccgc tcgtcgtggt ggtccgcgtg tggaattaga acgcgtgagc | 900 |
| ttcccgctga agcgcggtca gagtctgtta gctttaggca ccgccaaagc agcagaaggt | 960 |
| aaagcaagcc gtaccgtgcc ggttgttcat gcctatggct tcagcagcgc cggttaccaa | 1020 |
| caaggttggg gcgcagcttt agaagttcgt gatctggtgg accaagctat tggtagcagc | 1080 |
| agtagtgcca gtagtggccg ttatttagcc aaactg | 1116 |

<210> SEQ ID NO 72
<211> LENGTH: 372
<212> TYPE: PRT
<213> ORGANISM: Artificial Sequence
<220> FEATURE:
<223> OTHER INFORMATION: N54T- T56T- F58Q-C211L-M213T

<400> SEQUENCE: 72

Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Thr Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys

| | | | | | 195 | | | | 200 | | | | 205 | | |
|---|---|---|---|---|---|---|---|---|---|---|---|---|---|---|---|
| Lys | Arg | Leu | Thr | Thr | Asp | Ser | Ser | Asp | Pro | Lys | Ser | Pro | Ala | Tyr | Ile |
| 210 | | | | | 215 | | | | | 220 | | | | | |
| Ile | Pro | Arg | Pro | Gly | Gly | Glu | Val | Ile | Cys | Gly | Thr | Tyr | Leu | Val | |
| 225 | | | | | 230 | | | | | 235 | | | | 240 | |
| Gly | Asn | Tyr | Asp | Leu | Ser | Val | Asp | Pro | Ala | Thr | Ile | Pro | Arg | Ile | Leu |
| | | | | 245 | | | | | 250 | | | | | 255 | |
| Lys | His | Cys | Leu | Arg | Leu | Asp | Pro | Ser | Ile | Ser | Thr | Asp | Gly | Thr | Leu |
| | | | 260 | | | | | 265 | | | | | 270 | | |
| Glu | Gly | Ile | Glu | Ile | Leu | Arg | His | Asn | Val | Gly | Leu | Arg | Pro | Ala | Arg |
| | | 275 | | | | | 280 | | | | | 285 | | | |
| Arg | Gly | Pro | Arg | Val | Glu | Leu | Glu | Arg | Val | Ser | Phe | Pro | Leu | Lys | |
| 290 | | | | 295 | | | | | 300 | | | | | | |
| Arg | Gly | Gln | Ser | Leu | Leu | Ala | Leu | Gly | Thr | Ala | Lys | Ala | Ala | Glu | Gly |
| 305 | | | | 310 | | | | 315 | | | | | | 320 | |
| Lys | Ala | Ser | Arg | Thr | Val | Pro | Val | Val | His | Ala | Tyr | Gly | Phe | Ser | Ser |
| | | | | 325 | | | | | 330 | | | | | 335 | |
| Ala | Gly | Tyr | Gln | Gln | Gly | Trp | Gly | Ala | Ala | Leu | Glu | Val | Arg | Asp | Leu |
| | | | | 340 | | | | | 345 | | | | 350 | | |
| Val | Asp | Gln | Ala | Ile | Gly | Ser | Ser | Ser | Ala | Ser | Ser | Gly | Arg | Tyr | |
| | | 355 | | | | | 360 | | | | | 365 | | | |
| Leu | Ala | Lys | Leu | | | | | | | | | | | | |
| | 370 | | | | | | | | | | | | | | |

<210> SEQ ID NO 73
<211> LENGTH: 1116
<212> TYPE: DNA
<213> ORGANISM: Artificial Sequence
<220> FEATURE:
<223> OTHER INFORMATION: N54T- T56T- F58Q-C211L-M213T

<400> SEQUENCE: 73

| | | |
|---|---|---|
| atgacccaga taagcgcgt ggttgttctg ggcagtggcg ttattggtct gagctgtgct | 60 |
| ttagctttag cccagaaggg ctataaagtg catgtggttg cccgcgatct gccggaagac | 120 |
| acagtggccc agacctttgc aagcccttgg gccggtgcaa cttggacccc gcagatgagc | 180 |
| aaagaagctg gtccgcgtca agctaaatgg gaggaagcaa ccttcaaaca gtgggtggac | 240 |
| ttcgttccgc aaggtctggc aatgtggctg aaaggtaccc gccgctttgc agaaaccgaa | 300 |
| gccgatctgc tgggccattg gtataaggac atcgtgccga attaccgcca tctgaacccg | 360 |
| agcgattgtc cgccgggcgc aattggcgtg acctacgata cttttaagcgt taacgccccg | 420 |
| aagttctgtc agtatctgca gcgcgaagca cagaaactgg gcgtgacctt cgaacgccgt | 480 |
| ttagttacct ctttagagca gattgcagat ggcgccgatc tgatcgttaa tgcaaccggt | 540 |
| ctgggcgcca aaagcatcgc cggtgtggaa gatcaagaag tggaacctat ccgcggccaa | 600 |
| acagtgctga ttaagagcaa ctgtaaacgc ctgaccactg acagtagtga cccgaaaagc | 660 |
| ccggcctaca ttattccgcg cccgggtggt gaagtgatct gtggtggtac ctatttagtg | 720 |
| ggtaactatg atttaagcgt ggatccggcc accattccgc gcattttaaa acattgtctg | 780 |
| cgtttagacc cgagtattag caccgacggc acactggaag catcgaaat tttacgccat | 840 |
| aacgttggtc tgcgtcccgc tcgtcgtggt ggtccgcgtg tggaattaga acgcgtgagc | 900 |
| ttcccgctga agcgcggtca gagtctgtta gctttaggca ccgccaaagc agcagaaggt | 960 |
| aaagcaagcc gtaccgtgcc ggttgttcat gcctatggct cagcagcgc cggttaccaa | 1020 |

```
caaggttggg gcgcagcttt agaagttcgt gatctggtgg accaagctat tggtagcagc   1080
agtagtgcca gtagtggccg ttatttagcc aaactg                              1116
```

<210> SEQ ID NO 74
<211> LENGTH: 1116
<212> TYPE: DNA
<213> ORGANISM: Artificial Sequence
<220> FEATURE:
<223> OTHER INFORMATION: N54A- T56T- F58H-C211L-M213T

<400> SEQUENCE: 74

```
atgacccaga ataagcgcgt ggttgttctg ggcagtggcg ttattggtct gagctgtgct    60
ttagctttag cccagaaggg ctataaagtg catgtggttg cccgcgatct gccggaagac   120
acagtggccc agacctttgc aagcccttgg gccggtgcag cgtggacccc gcatatgagc   180
aaagaagctg gtccgcgtca agctaaatgg gaggaagcaa ccttcaaaca gtgggtggac   240
ttcgttccgc aaggtctggc aatgtggctg aaaggtaccc gccgctttgc agaaaccgaa   300
gccgatctgc tgggccattg gtataaggac atcgtgccga attaccgcca tctgaacccg   360
agcgattgtc cgccgggcgc aattggcgtg acctacgata ctttaagcgt aacgccccg    420 aagttctgtc agtatctgca gcgcgaagca cagaaactgg gcgtgacctt cgaacgccgt   480
ttagttacct cttttagaca gattgcagat ggcgccgatc tgatcgttaa tgcaaccggt   540
ctgggcgcca aaagcatcgc cggtgtggaa gatcaagaag tggaacctat ccgcggccaa   600
acagtgctga ttaagagcaa ctgtaaacgc ctgaccactg acagtagtga cccgaaaagc   660
ccggcctaca ttattccgcg cccgggtggt gaagtgatct gtggtggtac ctatttagtg   720
ggtaactatg atttaagcgt ggatccggcc accattccgc gcattttaaa acattgtctg   780
cgtttagacc cgagtattag caccgacggc acactggaag gcatcgaaat tttacgccat   840
aacgttggtc tgcgtcccgc tcgtcgtggt ggtccgcgtg tggaattaga acgcgtgagc   900
ttcccgctga gcgcggtca gagtctgtta gctttaggca ccgccaaagc agcagaaggt   960
aaagcaagcc gtaccgtgcc ggttgttcat gcctatggct tcagcagcgc cggttaccaa  1020
caaggttggg gcgcagcttt agaagttcgt gatctggtgg accaagctat tggtagcagc  1080
agtagtgcca gtagtggccg ttatttagcc aaactg                             1116
```

<210> SEQ ID NO 75
<211> LENGTH: 372
<212> TYPE: PRT
<213> ORGANISM: Artificial Sequence
<220> FEATURE:
<223> OTHER INFORMATION: 54A- T56T- F58Q-C211L-M213T

<400> SEQUENCE: 75

```
Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Ala Trp Thr Pro Gln Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95
```

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Leu Thr Thr Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 76
<211> LENGTH: 1116
<212> TYPE: DNA
<213> ORGANISM: Artificial Sequence
<220> FEATURE:
<223> OTHER INFORMATION: 54A- T56T- F58Q-C211L-M213T

<400> SEQUENCE: 76
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag cttggacccc gcagatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata ctttaagcgt taacgccccg     420

| aagttctgtc agtatctgca gcgcgaagca cagaaactgg gcgtgacctt cgaacgccgt | 480 |
| ttagttacct ctttagagca gattgcagat ggcgccgatc tgatcgttaa tgcaaccggt | 540 |
| ctgggcgcca aaagcatcgc cggtgtggaa gatcaagaag tggaacctat ccgcggccaa | 600 |
| acagtgctga ttaagagcaa ctgtaaacgc ctgaccactg acagtagtga cccgaaaagc | 660 |
| ccggcctaca ttattccgcg cccgggtggt gaagtgatct gtggtggtac ctatttagtg | 720 |
| ggtaactatg atttaagcgt ggatccggcc accattccgc gcattttaaa acattgtctg | 780 |
| cgtttagacc cgagtattag caccgacggc acactggaag gcatcgaaat tttacgccat | 840 |
| aacgttggtc tgcgtcccgc tcgtcgtggt ggtccgcgtg tggaattaga acgcgtgagc | 900 |
| ttcccgctga gcgcggtca gagtctgtta gctttaggca ccgccaaagc agcagaaggt | 960 |
| aaagcaagcc gtaccgtgcc ggttgttcat gcctatggct tcagcagcgc cggttaccaa | 1020 |
| caaggttggg gcgcagcttt agaagttcgt gatctggtgg accaagctat tggtagcagc | 1080 |
| agtagtgcca gtagtggccg ttatttagcc aaactg | 1116 |

<210> SEQ ID NO 77
<211> LENGTH: 1116
<212> TYPE: DNA
<213> ORGANISM: Artificial Sequence
<220> FEATURE:
<223> OTHER INFORMATION: N54A- T56T- F58K-C211L-M213

<400> SEQUENCE: 77

| atgacccaga ataagcgcgt ggttgttctg ggcagtggcg ttattggtct gagctgtgct | 60 |
| ttagctttag cccagaaggg ctataaagtg catgtggttg cccgcgatct gccggaagac | 120 |
| acagtggccc agacctttgc aagcccttgg gccggtgcag cgtggactcc gaagatgagc | 180 |
| aaagaagctg gtccgcgtca agctaaatgg gaggaagcaa ccttcaaaca gtgggtggac | 240 |
| ttcgttccgc aaggtctggc aatgtggctg aaaggtaccc gccgctttgc agaaaccgaa | 300 |
| gccgatctgc tgggccattg gtataaggac atcgtgccga attaccgcca tctgaacccg | 360 |
| agcgattgtc cgccgggcgc aattggcgtg acctacgata ctttaagcgt taacgccccg | 420 |
| aagttctgtc agtatctgca gcgcgaagca cagaaactgg gcgtgacctt cgaacgccgt | 480 |
| ttagttacct ctttagagca gattgcagat ggcgccgatc tgatcgttaa tgcaaccggt | 540 |
| ctgggcgcca aaagcatcgc cggtgtggaa gatcaagaag tggaacctat ccgcggccaa | 600 |
| acagtgctga ttaagagcaa ctgtaaacgc ctgaccactg acagtagtga cccgaaaagc | 660 |
| ccggcctaca ttattccgcg cccgggtggt gaagtgatct gtggtggtac ctatttagtg | 720 |
| ggtaactatg atttaagcgt ggatccggcc accattccgc gcattttaaa acattgtctg | 780 |
| cgtttagacc cgagtattag caccgacggc acactggaag gcatcgaaat tttacgccat | 840 |
| aacgttggtc tgcgtcccgc tcgtcgtggt ggtccgcgtg tggaattaga acgcgtgagc | 900 |
| ttcccgctga gcgcggtca gagtctgtta gctttaggca ccgccaaagc agcagaaggt | 960 |
| aaagcaagcc gtaccgtgcc ggttgttcat gcctatggct tcagcagcgc cggttaccaa | 1020 |
| caaggttggg gcgcagcttt agaagttcgt gatctggtgg accaagctat tggtagcagc | 1080 |
| agtagtgcca gtagtggccg ttatttagcc aaactg | 1116 |

<210> SEQ ID NO 78
<211> LENGTH: 1116
<212> TYPE: DNA
<213> ORGANISM: Artificial Sequence
<220> FEATURE:
<223> OTHER INFORMATION: N54A- T56T- F58K-C211L-M213T

<400> SEQUENCE: 78

```
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag cgtggacgcc gaagatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata ctttaagcgt taacgccccg     420
aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtggaa gatcaagaag tggaacctat ccgcggccaa     600
acagtgctga ttaagagcaa ctgtaaacgc ctgaccactg acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcatttttaaa acattgtctg     780
cgtttagacc cgagtattag caccgacggc acactggaag gcatcgaaat tttacgccat     840
aacgttggtc tgcgtcccgc tcgtcgtggt ggtccgcgtg tggaattaga acgcgtgagc     900
ttcccgctga agcgcggtca gagtctgtta gctttaggca ccgccaaagc agcagaaggt     960
aaagcaagcc gtaccgtgcc ggttgttcat gcctatggct tcagcagcgc cggttaccaa    1020
caaggttggg gcgcagcttt agaagttcgt gatctggtgg accaagctat tggtagcagc    1080
agtagtgcca gtagtggccg ttatttagcc aaactg                              1116
```

<210> SEQ ID NO 79
<211> LENGTH: 372
<212> TYPE: PRT
<213> ORGANISM: Artificial Sequence
<220> FEATURE:
<223> OTHER INFORMATION: N54A- T56N- F58H-C211L-M213T

<400> SEQUENCE: 79

```
Met Thr Gln Asn Lys Arg Val Val Val Leu Gly Ser Gly Val Ile Gly
  1               5                  10                  15

Leu Ser Cys Ala Leu Ala Leu Ala Gln Lys Gly Tyr Lys Val His Val
             20                  25                  30

Val Ala Arg Asp Leu Pro Glu Asp Thr Val Ala Gln Thr Phe Ala Ser
         35                  40                  45

Pro Trp Ala Gly Ala Ala Trp Asn Pro His Met Ser Lys Glu Ala Gly
     50                  55                  60

Pro Arg Gln Ala Lys Trp Glu Glu Ala Thr Phe Lys Gln Trp Val Asp
 65                  70                  75                  80

Phe Val Pro Gln Gly Leu Ala Met Trp Leu Lys Gly Thr Arg Arg Phe
                 85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
```

```
                145                 150                 155                 160
Leu Val Thr Ser Leu Glu Gln Ile Ala Asp Gly Ala Asp Leu Ile Val
                    165                 170                 175

Asn Ala Thr Gly Leu Gly Ala Lys Ser Ile Ala Gly Val Glu Asp Gln
                180                 185                 190

Glu Val Glu Pro Ile Arg Gly Gln Thr Val Leu Ile Lys Ser Asn Cys
            195                 200                 205

Lys Arg Leu Thr Thr Asp Ser Ser Asp Pro Lys Ser Pro Ala Tyr Ile
        210                 215                 220

Ile Pro Arg Pro Gly Gly Glu Val Ile Cys Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 80
<211> LENGTH: 1116
<212> TYPE: DNA
<213> ORGANISM: Artificial Sequence
<220> FEATURE:
<223> OTHER INFORMATION: N54A- T56N- F58H-C211L-M213T

<400> SEQUENCE: 80
atgacccaga taagcgcgt ggttgttctg ggcagtggcg ttattggtct gagctgtgct      60
ttagctttag cccagaaggg ctataaagtg catgtggttg cccgcgatct gccggaagac    120
acagtggccc agacctttgc aagcccttgg gccggtgcag cttggaatcc gcatatgagc    180
aaagaagctg gtccgcgtca agctaaatgg gaggaagcaa ccttcaaaca gtgggtggac    240
ttcgttccgc aaggtctggc aatgtggctg aaaggtaccc gccgctttgc agaaaccgaa    300
gccgatctgc tgggccattg gtataaggac atcgtgccga attaccgcca tctgaacccg    360
agcgattgtc cgccgggcgc aattggcgtg acctacgata ctttaagcgt taacgccccg    420
aagttctgtc agtatctgca gcgcgaagca cagaaactgg gcgtgacctt cgaacgccgt    480
ttagttacct ctttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc tgaccactg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
```

```
cgtttagacc cgagtattag caccgacggc acactggaag gcatcgaaat tttacgccat      840
aacgttggtc tgcgtcccgc tcgtcgtggt ggtccgcgtg tggaattaga acgcgtgagc      900
ttcccgctga agcgcggtca gagtctgtta gctttaggca ccgccaaagc agcagaaggt      960
aaagcaagcc gtaccgtgcc ggttgttcat gcctatggct tcagcagcgc cggttaccaa     1020
caaggttggg gcgcagcttt agaagttcgt gatctggtgg accaagctat tggtagcagc     1080
agtagtgcca gtagtggccg ttatttagcc aaactg                               1116
```

<210> SEQ ID NO 81
<211> LENGTH: 1116
<212> TYPE: DNA
<213> ORGANISM: Artificial Sequence
<220> FEATURE:
<223> OTHER INFORMATION: N54A- T56N- F58H-C211L-M213T

<400> SEQUENCE: 81

```
atgacccaga ataagcgcgt ggttgttctg ggcagtggcg ttattggtct gagctgtgct       60
ttagctttag cccagaaggg ctataaagtg catgtggttg cccgcgatct gccggaagac      120
acagtggccc agacctttgc aagcccttgg gccggtgcag cttggaatcc gcatatgagc      180
aaagaagctg gtccgcgtca agctaaatgg gaggaagcaa ccttcaaaca gtgggtggac      240
ttcgttccgc aaggtctggc aatgtggctg aaaggtaccc gccgctttgc agaaaccgaa      300
gccgatctgc tgggccattg gtataaggac atcgtgccga attaccgcca tctgaacccg      360
agcgattgtc cgccgggcgc aattggcgtg acctacgata ctttaagcgt taacgccccg      420
aagttctgtc agtatctgca gcgcgaagca cagaaactgg gcgtgacctt cgaacgccgt      480
ttagttacct ctttagagca gattgcagat ggcgccgatc tgatcgttaa tgcaaccggt      540
ctgggcgcca aaagcatcgc cggtgtggaa gatcaagaag tggaacctat ccgcggccaa      600
acagtgctga ttaagagcaa ctgtaaacgc ctgaccactg acagtagtga cccgaaaagc      660
ccggcctaca ttattccgcg cccgggtggt gaagtgatct gtggtggtac ctatttagtg      720
ggtaactatg atttaagcgt ggatccggcc accattccgc gcattttaaa acattgtctg      780
cgtttagacc cgagtattag caccgacggc acactggaag gcatcgaaat tttacgccat      840
aacgttggtc tgcgtcccgc tcgtcgtggt ggtccgcgtg tggaattaga acgcgtgagc      900
ttcccgctga agcgcggtca gagtctgtta gctttaggca ccgccaaagc agcagaaggt      960
aaagcaagcc gtaccgtgcc ggttgttcat gcctatggct tcagcagcgc cggttaccaa     1020
caaggttggg gcgcagcttt agaagttcgt gatctggtgg accaagctat tggtagcagc     1080
agtagtgcca gtagtggccg ttatttagcc aaactg                               1116
```

<210> SEQ ID NO 82
<211> LENGTH: 372
<212> TYPE: PRT
<213> ORGANISM: Artificial Sequence
<220> FEATURE:
<223> OTHER INFORMATION: N54A- T56S- F58H-C211L-M213T

<400> SEQUENCE: 82

```
Met Thr Gln Asn Lys Arg Val Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45
```

Pro Trp Ala Gly Ala Ala Trp Ser Pro His Met Ser Lys Glu Ala Gly
 50                  55                  60

Pro Arg Gln Ala Lys Trp Glu Glu Ala Thr Phe Lys Gln Trp Val Asp
 65                  70                  75                  80

Phe Val Pro Gln Gly Leu Ala Met Trp Leu Lys Gly Thr Arg Arg Phe
                 85                  90                  95

Ala Glu Thr Glu Ala Asp Leu Leu Gly His Trp Tyr Lys Asp Ile Val
             100                 105                 110

Pro Asn Tyr Arg His Leu Asn Pro Ser Asp Cys Pro Pro Gly Ala Ile
         115                 120                 125

Gly Val Thr Tyr Asp Thr Leu Ser Val Asn Ala Pro Lys Phe Cys Gln
130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Leu Thr Thr Asp Ser Ser Asp Pro Lys Ser Pro Ala Tyr Ile
210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu
            340                 345                 350

Val Asp Gln Ala Ile Gly Ser Ser Ser Ala Ser Ser Gly Arg Tyr
        355                 360                 365

Leu Ala Lys Leu
    370

<210> SEQ ID NO 83
<211> LENGTH: 1116
<212> TYPE: DNA
<213> ORGANISM: Artificial Sequence
<220> FEATURE:
<223> OTHER INFORMATION: N54A- T56S- F58H-C211L-M213T

<400> SEQUENCE: 83
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag cttggtcgcc gcatatgagc     180

```
aaagaagctg gtccgcgtca agctaaatgg gaggaagcaa ccttcaaaca gtgggtggac    240
ttcgttccgc aaggtctggc aatgtggctg aaaggtaccc gccgctttgc agaaaccgaa    300
gccgatctgc tgggccattg gtataaggac atcgtgccga attaccgcca tctgaacccg    360
agcgattgtc cgccgggcgc aattggcgtg acctacgata ctttaagcgt taacgccccg    420
aagttctgtc agtatctgca gcgcgaagca cagaaactgg gcgtgacctt cgaacgccgt    480
ttagttacct ctttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc ctgaccactg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag gcatcgaaat tttacgccat    840
aacgttggtc tgcgtcccgc tcgtcgtggt ggtccgcgtg tggaattaga acgcgtgagc    900
ttcccgctga gcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg gcgcagcttt agaagttcgt gatctggtgg accaagctat tggtagcagc   1080
agtagtgcca gtagtggccg ttatttagcc aaactg                              1116

<210> SEQ ID NO 84
<211> LENGTH: 1116
<212> TYPE: DNA
<213> ORGANISM: Artificial Sequence
<220> FEATURE:
<223> OTHER INFORMATION: N54A- T56S- F58H-C211L-M213T

<400> SEQUENCE: 84
atgacccaga ataagcgcgt ggttgttctg ggcagtggcg ttattggtct gagctgtgct     60
ttagctttag cccagaaggg ctataaagtg catgtggttg cccgcgatct gccggaagac    120
acagtggccc agacctttgc aagcccttgg gccggtgcag cttggtcgcc gcatatgagc    180
aaagaagctg gtccgcgtca agctaaatgg gaggaagcaa ccttcaaaca gtgggtggac    240
ttcgttccgc aaggtctggc aatgtggctg aaaggtaccc gccgctttgc agaaaccgaa    300
gccgatctgc tgggccattg gtataaggac atcgtgccga attaccgcca tctgaacccg    360
agcgattgtc cgccgggcgc aattggcgtg acctacgata ctttaagcgt taacgccccg    420
aagttctgtc agtatctgca gcgcgaagca cagaaactgg gcgtgacctt cgaacgccgt    480
ttagttacct ctttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc ctgaccactg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag gcatcgaaat tttacgccat    840
aacgttggtc tgcgtcccgc tcgtcgtggt ggtccgcgtg tggaattaga acgcgtgagc    900
ttcccgctga gcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg gcgcagcttt agaagttcgt gatctggtgg accaagctat tggtagcagc   1080
```
agtagtgcca gtagtggccg ttatttagcc aaactg        1116

<210> SEQ ID NO 85
<211> LENGTH: 1116
<212> TYPE: DNA
<213> ORGANISM: Artificial Sequence
<220> FEATURE:
<223> OTHER INFORMATION: N54A- T56S- F58H-C211L-M213T

<400> SEQUENCE: 85

```
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag cgtggtcgcc gcatatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata cttttaagcgt taacgccccg     420
aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtggaa gatcaagaag tggaacctat ccgcggccaa     600
acagtgctga ttaagagcaa ctgtaaacgc ctgaccactg acagtagtga cccgaaaagc     660
ccggcctaca ttattccgcg cccgggtggt gaagtgatct gtggtggtac ctatttagtg     720
ggtaactatg atttaagcgt ggatccggcc accattccgc gcattttaaa acattgtctg     780
cgtttagacc cgagtattag caccgacggc acactggaag gcatcgaaat tttacgccat     840
aacgttggtc tgcgtcccgc tcgtcgtggt ggtccgcgtg tggaattaga acgcgtgagc     900
ttcccgctga gcgcggtca gagtctgtta gctttaggca ccgccaaagc agcagaaggt     960
aaagcaagcc gtaccgtgcc ggttgttcat gcctatggct tcagcagcgc cggttaccaa    1020
caaggttggg gcgcagcttt agaagttcgt gatctggtgg accaagctat tggtagcagc    1080
agtagtgcca gtagtggccg ttatttagcc aaactg                              1116
```

<210> SEQ ID NO 86
<211> LENGTH: 1116
<212> TYPE: DNA
<213> ORGANISM: Artificial Sequence
<220> FEATURE:
<223> OTHER INFORMATION: N54A- T56T- F58H-C211L-M213T

<400> SEQUENCE: 86

```
atgacccaga ataagcgcgt ggttgttctg ggcagtggcg ttattggtct gagctgtgct      60
ttagctttag cccagaaggg ctataaagtg catgtggttg cccgcgatct gccggaagac     120
acagtggccc agacctttgc aagcccttgg gccggtgcag cgtggacgcc gcatatgagc     180
aaagaagctg gtccgcgtca agctaaatgg gaggaagcaa ccttcaaaca gtgggtggac     240
ttcgttccgc aaggtctggc aatgtggctg aaaggtaccc gccgctttgc agaaaccgaa     300
gccgatctgc tgggccattg gtataaggac atcgtgccga attaccgcca tctgaacccg     360
agcgattgtc cgccgggcgc aattggcgtg acctacgata cttttaagcgt taacgccccg     420
aagttctgtc agtatctgca gcgcgaagca cagaaactgg gcgtgacctt cgaacgccgt     480
ttagttacct ctttagagca gattgcagat ggcgccgatc tgatcgttaa tgcaaccggt     540
ctgggcgcca aaagcatcgc cggtgtggaa gatcaagaag tggaacctat ccgcggccaa     600
```

```
acagtgctga ttaagagcaa ctgtaaacgc ctgaccactg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag gcatcgaaat tttacgccat    840
aacgttggtc tgcgtcccgc tcgtcgtggt ggtccgcgtg tggaattaga acgcgtgagc    900
ttcccgctga agcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg gcgcagcttt agaagttcgt gatctggtgg accaagctat tggtagcagc   1080
agtagtgcca gtagtggccg ttatttagcc aaactg                             1116
```

<210> SEQ ID NO 87
<211> LENGTH: 1116
<212> TYPE: DNA
<213> ORGANISM: Artificial Sequence
<220> FEATURE:
<223> OTHER INFORMATION: N54A- T56T- F58H-C211L-M213T

<400> SEQUENCE: 87

```
atgacccaga ataagcgcgt ggttgttctg ggcagtggcg ttattggtct gagctgtgct     60
ttagctttag cccagaaggg ctataaagtg catgtggttg cccgcgatct gccggaagac    120
acagtggccc agacctttgc aagcccttgg gccggtgcag cgtggactcc gcatatgagc    180
aaagaagctg gtccgcgtca agctaaatgg gaggaagcaa ccttcaaaca gtgggtggac    240
ttcgttccgc aaggtctggc aatgtggctg aaaggtaccc gccgctttgc agaaaccgaa    300
gccgatctgc tgggccattg gtataaggac atcgtgccga attaccgcca tctgaacccg    360
agcgattgtc cgccgggcgc aattggcgtg acctacgata cttttaagcgt taacgccccg    420 aagttctgtc agtatctgca gcgcgaagca cagaaactgg gcgtgacctt cgaacgccgt    480
ttagttacct ctttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc ctgaccactg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag gcatcgaaat tttacgccat    840
aacgttggtc tgcgtcccgc tcgtcgtggt ggtccgcgtg tggaattaga acgcgtgagc    900
ttcccgctga agcgcggtca gagtctgtta gctttaggca ccgccaaagc agcagaaggt    960
aaagcaagcc gtaccgtgcc ggttgttcat gcctatggct tcagcagcgc cggttaccaa   1020
caaggttggg gcgcagcttt agaagttcgt gatctggtgg accaagctat tggtagcagc   1080
agtagtgcca gtagtggccg ttatttagcc aaactg                             1116
```

<210> SEQ ID NO 88
<211> LENGTH: 1116
<212> TYPE: DNA
<213> ORGANISM: Artificial Sequence
<220> FEATURE:
<223> OTHER INFORMATION: N54A- T56S- F58H-C211L-M213T

<400> SEQUENCE: 88

```
atgacccaga ataagcgcgt ggttgttctg ggcagtggcg ttattggtct gagctgtgct     60
```

```
ttagctttag cccagaaggg ctataaagtg catgtggttg cccgcgatct gccggaagac    120
acagtggccc agacctttgc aagcccttgg gccggtgcag cgtggagtcc gcatatgagc    180
aaagaagctg gtccgcgtca agctaaatgg gaggaagcaa ccttcaaaca gtgggtggac    240
ttcgttccgc aaggtctggc aatgtggctg aaaggtaccc gccgctttgc agaaaccgaa    300
gccgatctgc tgggccattg gtataaggac atcgtgccga attaccgcca tctgaacccg    360
agcgattgtc cgccgggcgc aattggcgtg acctacgata cttttaagcgt taacgccccg    420 aagttctgtc agtatctgca gcgcgaagca cagaaactgg gcgtgaccctt cgaacgccgt    480 ttagttacct cttttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc ctgaccactg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag gcatcgaaat tttacgccat    840
aacgttggtc tgcgtcccgc tcgtcgtggt ggtccgcgtg tggaattaga acgcgtgagc    900
ttcccgctga gcgcggtca gagtctgtta gctttaggca ccgccaaagc agcagaaggt    960
aaagcaagcc gtaccgtgcc ggttgttcat gcctatggct tcagcagcgc cggttaccaa    1020
caaggttggg gcgcagcttt agaagttcgt gatctggtgg accaagctat tggtagcagc    1080
agtagtgcca gtagtggccg ttatttagcc aaactg                            1116
```

<210> SEQ ID NO 89
<211> LENGTH: 1116
<212> TYPE: DNA
<213> ORGANISM: Artificial Sequence
<220> FEATURE:
<223> OTHER INFORMATION: N54A- T56N- F58H-C211L-M213T

<400> SEQUENCE: 89

```
atgacccaga ataagcgcgt ggttgttctg ggcagtggcg ttattggtct gagctgtgct     60
ttagctttag cccagaaggg ctataaagtg catgtggttg cccgcgatct gccggaagac    120
acagtggccc agacctttgc aagcccttgg gccggtgcag cgtggaatcc gcatatgagc    180
aaagaagctg gtccgcgtca agctaaatgg gaggaagcaa ccttcaaaca gtgggtggac    240
ttcgttccgc aaggtctggc aatgtggctg aaaggtaccc gccgctttgc agaaaccgaa    300
gccgatctgc tgggccattg gtataaggac atcgtgccga attaccgcca tctgaacccg    360
agcgattgtc cgccgggcgc aattggcgtg acctacgata cttttaagcgt taacgccccg    420 aagttctgtc agtatctgca gcgcgaagca cagaaactgg gcgtgaccctt cgaacgccgt    480 ttagttacct cttttagagca gattgcagat ggcgccgatc tgatcgttaa tgcaaccggt    540
ctgggcgcca aaagcatcgc cggtgtggaa gatcaagaag tggaacctat ccgcggccaa    600
acagtgctga ttaagagcaa ctgtaaacgc ctgaccactg acagtagtga cccgaaaagc    660
ccggcctaca ttattccgcg cccgggtggt gaagtgatct gtggtggtac ctatttagtg    720
ggtaactatg atttaagcgt ggatccggcc accattccgc gcattttaaa acattgtctg    780
cgtttagacc cgagtattag caccgacggc acactggaag gcatcgaaat tttacgccat    840
aacgttggtc tgcgtcccgc tcgtcgtggt ggtccgcgtg tggaattaga acgcgtgagc    900
ttcccgctga gcgcggtca gagtctgtta gctttaggca ccgccaaagc agcagaaggt    960
aaagcaagcc gtaccgtgcc ggttgttcat gcctatggct tcagcagcgc cggttaccaa    1020
```
caaggttggg gcgcagcttt agaagttcgt gatctggtgg accaagctat tggtagcagc    1080
agtagtgcca gtagtggccg ttatttagcc aaactg                              1116

<210> SEQ ID NO 90
<211> LENGTH: 372
<212> TYPE: PRT
<213> ORGANISM: Artificial Sequence
<220> FEATURE:
<223> OTHER INFORMATION: N54A- T56L- F58H-C211L-M213T

<400> SEQUENCE: 90

Met Thr Gln Asn Lys Arg Val Val Leu Gly Ser Gly Val Ile Gly
1               5                   10                  15

Leu Ser Cys Ala Leu Ala Leu Ala Gln Lys Gly Tyr Lys Val His Val
            20                  25                  30

Val Ala Arg Asp Leu Pro Glu Asp Thr Val Ala Gln Thr Phe Ala Ser
        35                  40                  45

Pro Trp Ala Gly Ala Ala Trp Leu Pro His Met Ser Lys Glu Ala Gly
    50                  55                  60

Pro Arg Gln Ala Lys Trp Glu Glu Ala Thr Phe Lys Gln Trp Val Asp
65                  70                  75                  80

Phe Val Pro Gln Gly Leu Ala Met Trp Leu Lys Gly Thr Arg Arg Phe
                85                  90                  95

Ala Glu Thr Glu Ala Asp Leu Leu Gly His Trp Tyr Lys Asp Ile Val
            100                 105                 110

Pro Asn Tyr Arg His Leu Asn Pro Ser Asp Cys Pro Pro Gly Ala Ile
        115                 120                 125

Gly Val Thr Tyr Asp Thr Leu Ser Val Asn Ala Pro Lys Phe Cys Gln
    130                 135                 140

Tyr Leu Gln Arg Glu Ala Gln Lys Leu Gly Val Thr Phe Glu Arg Arg
145                 150                 155                 160

Leu Val Thr Ser Leu Glu Gln Ile Ala Asp Gly Ala Asp Leu Ile Val
                165                 170                 175

Asn Ala Thr Gly Leu Gly Ala Lys Ser Ile Ala Gly Val Glu Asp Gln
            180                 185                 190

Glu Val Glu Pro Ile Arg Gly Gln Thr Val Leu Ile Lys Ser Asn Cys
        195                 200                 205

Lys Arg Leu Thr Thr Asp Ser Ser Asp Pro Lys Ser Pro Ala Tyr Ile
    210                 215                 220

Ile Pro Arg Pro Gly Gly Glu Val Ile Cys Gly Gly Thr Tyr Leu Val
225                 230                 235                 240

Gly Asn Tyr Asp Leu Ser Val Asp Pro Ala Thr Ile Pro Arg Ile Leu
                245                 250                 255

Lys His Cys Leu Arg Leu Asp Pro Ser Ile Ser Thr Asp Gly Thr Leu
            260                 265                 270

Glu Gly Ile Glu Ile Leu Arg His Asn Val Gly Leu Arg Pro Ala Arg
        275                 280                 285

Arg Gly Gly Pro Arg Val Glu Leu Glu Arg Val Ser Phe Pro Leu Lys
    290                 295                 300

Arg Gly Gln Ser Leu Leu Ala Leu Gly Thr Ala Lys Ala Ala Glu Gly
305                 310                 315                 320

Lys Ala Ser Arg Thr Val Pro Val Val His Ala Tyr Gly Phe Ser Ser
                325                 330                 335

Ala Gly Tyr Gln Gln Gly Trp Gly Ala Ala Leu Glu Val Arg Asp Leu

```
             340                 345                 350
Val Asp Gln Ala Ile Gly Ser Ser Ser Ala Ser Ser Gly Arg Tyr
            355                 360                 365

Leu Ala Lys Leu
    370
```

<210> SEQ ID NO 91
<211> LENGTH: 1116
<212> TYPE: DNA
<213> ORGANISM: Artificial Sequence
<220> FEATURE:
<223> OTHER INFORMATION: N54A- T56L- F58H-C211L-M213T

<400> SEQUENCE: 91

| | | |
|---|---|---|
| atgacccaga ataagcgcgt ggttgttctg ggcagtggcg ttattggtct gagctgtgct | 60 |
| ttagctttag cccagaaggg ctataaagtg catgtggttg cccgcgatct gccggaagac | 120 |
| acagtggccc agacctttgc aagcccttgg gccggtgcag cgtggcttcc gcatatgagc | 180 |
| aaagaagctg gtccgcgtca agctaaatgg gaggaagcaa ccttcaaaca gtgggtggac | 240 |
| ttcgttccgc aaggtctggc aatgtggctg aaaggtaccc gccgctttgc agaaaccgaa | 300 |
| gccgatctgc tgggccattg gtataaggac atcgtgccga attaccgcca tctgaacccg | 360 |
| agcgattgtc gccgggcgc aattggcgtg acctacgata ctttaagcgt taacgccccg | 420 |
| aagttctgtc agtatctgca gcgcgaagca cagaaactgg gcgtgacctt cgaacgccgt | 480 |
| ttagttacct ctttagagca gattgcagat ggcgccgatc tgatcgttaa tgcaaccggt | 540 |
| ctgggcgcca aaagcatcgc cggtgtggaa gatcaagaag tggaacctat ccgcggccaa | 600 |
| acagtgctga ttaagagcaa ctgtaaacgc ctgaccactg acagtagtga cccgaaaagc | 660 |
| ccggcctaca ttattccgcg cccgggtggt gaagtgatct gtggtggtac ctatttagtg | 720 |
| ggtaactatg atttaagcgt ggatccggcc accattccgc gcattttaaa acattgtctg | 780 |
| cgtttagacc cgagtattag caccgacggc acactggaag catcgaaat tttacgccat | 840 |
| aacgttggtc tgcgtcccgc tcgtcgtggt ggtccgcgtg tggaattaga acgcgtgagc | 900 |
| ttcccgctga gcgcggtca gagtctgtta gctttaggca ccgccaaagc agcagaaggt | 960 |
| aaagcaagcc gtaccgtgcc ggttgttcat gcctatggct tcagcagcgc cggttaccaa | 1020 |
| caaggttggg gcgcagcttt agaagttcgt gatctggtgg accaagctat tggtagcagc | 1080 |
| agtagtgcca gtagtggccg ttatttagcc aaactg | 1116 |

<210> SEQ ID NO 92
<211> LENGTH: 368
<212> TYPE: PRT
<213> ORGANISM: Artificial Sequence
<220> FEATURE:
<223> OTHER INFORMATION: rtDAAO(N54V-F58Q-M213S)

<400> SEQUENCE: 92

```
Met His Ser Gln Lys Arg Val Val Leu Gly Ser Gly Val Ile Gly
1               5                  10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Val Trp Thr Pro Gln Met Thr Leu Thr Asp Gly
    50                  55                  60

Pro Arg Gln Ala Lys Trp Glu Glu Ser Thr Phe Lys Lys Trp Val Glu
```

| | | 65 | | | 70 | | | 75 | | | 80 |
|---|---|---|---|---|---|---|---|---|---|---|---|

Leu Val Pro Thr Gly His Ala Met Trp Leu Lys Gly Thr Arg Arg Phe
                    85                  90                  95

Ala Gln Asn Glu Asp Gly Leu Leu Gly His Trp Tyr Lys Asp Ile Thr
                    100                 105                 110

Pro Asn Tyr Arg Pro Leu Pro Ser Ser Glu Cys Pro Pro Gly Ala Ile
                    115                 120                 125

Gly Val Thr Tyr Asp Thr Leu Ser Val His Ala Pro Lys Tyr Cys Gln
                130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                    165                 170                 175

Asn Ala Thr Gly Leu Gly Ala Lys Ser Ile Ala Gly Ile Asp Asp Gln
                    180                 185                 190

Ala Ala Glu Pro Ile Arg Gly Gln Thr Val Leu Val Lys Ser Pro Cys
                    195                 200                 205

Lys Arg Cys Thr Ser Asp Ser Ser Asp Pro Ala Ser Pro Ala Tyr Ile
                210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                    245                 250                 255

Lys His Cys Leu Arg Leu Asp Pro Thr Ile Ser Ser Asp Gly Thr Ile
                    260                 265                 270

Glu Gly Ile Glu Val Leu Arg His Asn Val Gly Leu Arg Pro Ala Arg
                275                 280                 285

Arg Gly Gly Pro Arg Val Glu Ala Glu Arg Ile Val Leu Pro Leu Asp
290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                    325                 330                 335

Gly Tyr Gln Gln Ser Trp Gly Ala Ala Glu Asp Val Ala Gln Leu Val
                340                 345                 350

Asp Glu Ala Phe Gln Arg Tyr His Gly Ala Ala Arg Glu Ser Lys Leu
                355                 360                 365

<210> SEQ ID NO 93
<211> LENGTH: 1104
<212> TYPE: DNA
<213> ORGANISM: Artificial Sequence
<220> FEATURE:
<223> OTHER INFORMATION: rtDAAO(N54V-F58Q-M213S)

<400> SEQUENCE: 93

```
atgcactctc agaaacgtgt tgttgttctg ggttctggtg ttatcggtct gtcttctgct      60
ctgatcctgg ctcgtaaagg ttactctgtt cacatcctgg ctcgtgacct gccggaagac     120
gtttcttctc agaccttcgc ttctccgtgg gctggtgctg tttggacccc gcagatgacc     180
ctgaccgacg tccgcgtca ggctaaatgg aagaatcta ccttcaaaaa atgggttgaa      240
ctggttccga ccggtcacgc tatgtggctg aaaggtaccc gtcgtttcgc tcagaacgaa     300
gacggtctgc tgggtcactg gtacaaagac atcaccccga actaccgtcc gctgccgtct     360
tctgaatgcc cgccgggtgc tatcggtgtt acctacgaca ccctgtctgt tcacgctccg     420
```

```
aaatactgcc agtacctggc tcgtgaactg cagaaactgg gtgctacctt cgaacgtcgt     480
accgttacct ctctggaaca ggctttcgac ggtgctgacc tggttgttaa cgctaccggt     540
ctgggtgcta atctatcgc tggtatcgac gaccaggctg ctgaaccgat ccgtggtcag      600
accgttctgg ttaaatctcc gtgcaaacgt tgcacctctg actcttctga cccggcttct     660
ccggcttaca tcatcccgcg tccgggtggt gaagttatct gcggtggtac ctacggtgtt     720
ggtgactggg acctgtctgt taacccggaa accgttcagc gtatcctgaa acactgcctg     780
cgtctggacc cgaccatctc ttctgacggt accatcgaag gtatcgaagt tctgcgtcac     840
aacgttggtc tgcgtccggc tcgtcgtggt ggtccgcgtg ttgaagctga acgtatcgtt     900
ctgccgctgg accgtaccaa atctccgctg tctctgggtc gtggttctgc tcgtgctgct     960
aaagaaaaag aagttaccct ggttcacgct acggtttct cttctgctgg ttaccagcag    1020
tcttggggtg ctgctgaaga cgttgctcag ctggttgacg aagctttcca gcgttaccac    1080
ggtgctgctc gtgaatctaa actg                                           1104
```

<210> SEQ ID NO 94
<211> LENGTH: 368
<212> TYPE: PRT
<213> ORGANISM: Artificial Sequence
<220> FEATURE:
<223> OTHER INFORMATION: rtDAAO(N54A-F58H)

<400> SEQUENCE: 94

```
Met His Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
                20                  25                  30

Leu Ala Arg Asp Leu Pro Glu Asp Val Ser Ser Gln Thr Phe Ala Ser
            35                  40                  45

Pro Trp Ala Gly Ala Ala Trp Thr Pro His Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Arg Cys Thr Met Asp Ser Ser Asp Pro Ala Ser Pro Ala Tyr Ile
    210                 215                 220

Ile Pro Arg Pro Gly Gly Glu Val Ile Cys Gly Gly Thr Tyr Gly Val
225                 230                 235                 240
```

-continued

```
Gly Asp Trp Asp Leu Ser Val Asn Pro Glu Thr Val Gln Arg Ile Leu
            245                 250                 255
Lys His Cys Leu Arg Leu Asp Pro Thr Ile Ser Ser Asp Gly Thr Ile
        260                 265                 270
Glu Gly Ile Glu Val Leu Arg His Asn Val Gly Leu Arg Pro Ala Arg
            275                 280                 285
Arg Gly Gly Pro Arg Val Glu Ala Glu Arg Ile Val Leu Pro Leu Asp
        290                 295                 300
Arg Thr Lys Ser Pro Leu Ser Leu Gly Arg Gly Ser Ala Arg Ala Ala
305                 310                 315                 320
Lys Glu Lys Glu Val Thr Leu Val His Ala Tyr Gly Phe Ser Ser Ala
            325                 330                 335
Gly Tyr Gln Gln Ser Trp Gly Ala Ala Glu Asp Val Ala Gln Leu Val
        340                 345                 350
Asp Glu Ala Phe Gln Arg Tyr His Gly Ala Ala Arg Glu Ser Lys Leu
    355                 360                 365
```

<210> SEQ ID NO 95
<211> LENGTH: 1104
<212> TYPE: DNA
<213> ORGANISM: Artificial Sequence
<220> FEATURE:
<223> OTHER INFORMATION: rtDAAO(N54A-F58H)

<400> SEQUENCE: 95

```
atgcactctc agaaacgtgt tgttgttctg ggttctggtg ttatcggtct gtcttctgct      60
ctgatcctgg ctcgtaaagg ttactctgtt cacatcctgg ctcgtgacct gccggaagac     120
gtttcttctc agaccttcgc ttctccgtgg gctggtgctg cttggacccc gcacatgacc     180
ctgaccgacg gtccgcgtca ggctaaatgg aagaatctac cttcaaaaa atgggttgaa     240
ctggttccga ccggtcacgc tatgtggctg aaaggtaccc gtcgtttcgc tcagaacgaa     300
gacggtctgc tgggtcactg gtacaaagac atcaccccga actaccgtcc gctgccgtct     360
tctgaatgcc cgccgggtgc tatcggtgtt acctacgaca ccctgtctgt tcacgctccg     420
aaatactgcc agtacctggc tcgtgaactg cagaaactgg tgctacctt cgaacgtcgt     480
accgttacct ctctggaaca ggctttcgac ggtgctgacc tggttgttaa cgctaccggt     540
ctgggtgcta aatctatcgc tggtatcgac gaccaggctg ctgaaccgat ccgtggtcag     600
accgttctgg ttaaatctcc gtgcaaacgt tgcaccatgg actcttctga cccggcttct     660
ccggcttaca tcatcccgcg tccgggtggt gaagttatct gcggtggtac ctacggtgtt     720
ggtgactggg acctgtctgt taacccggaa accgttcagc gtatcctgaa acactgcctg     780
cgtctggacc cgaccatctc ttctgacggt accatcgaag gtatcgaagt tctgcgtcac     840
aacgttggtc tgcgtccggc tcgtcgtggt ggtccgcgtg ttgaagctga acgtatcgtt     900
ctgccgctgg accgtaccaa atctccgctg tctctgggtc gtggttctgc tcgtgctgct     960
aaagaaaaag aagttaccct ggttcacgct tacggtttct cttctgctgg ttaccagcag    1020
tcttggggtg ctgctgaaga cgttgctcag ctggttgacg aagctttcca gcgttaccac    1080
ggtgctgctc gtgaatctaa actg                                           1104
```

<210> SEQ ID NO 96
<211> LENGTH: 368
<212> TYPE: PRT
<213> ORGANISM: Artificial Sequence
<220> FEATURE:

<223> OTHER INFORMATION: rtDAAO(N54A-56N-F58H)

<400> SEQUENCE: 96

```
Met His Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Ala Trp Asn Pro His Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Arg Cys Thr Met Asp Ser Ser Asp Pro Ala Ser Pro Ala Tyr Ile
    210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
    290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365
```

<210> SEQ ID NO 97
<211> LENGTH: 1104
<212> TYPE: DNA
<213> ORGANISM: Artificial Sequence
<220> FEATURE:

<223> OTHER INFORMATION: rtDAAO(N54A-56N-F58H)

<400> SEQUENCE: 97

```
atgcactctc agaaacgtgt tgttgttctg ggttctggtg ttatcggtct gtcttctgct    60
ctgatcctgg ctcgtaaagg ttactctgtt cacatcctgg ctcgtgacct gccggaagac   120
gtttcttctc agaccttcgc ttctccgtgg gctggtgctg cttggaaccc gcacatgacc   180
ctgaccgacg gtccgcgtca ggctaaatgg gaagaatcta ccttcaaaaa atgggttgaa   240
ctggttccga ccggtcacgc tatgtggctg aaaggtaccc gtcgtttcgc tcagaacgaa   300
gacggtctgc tgggtcactg gtacaaagac atcaccccga actaccgtcc gctgccgtct   360
tctgaatgcc cgccgggtgc tatcggtgtt acctacgaca ccctgtctgt tcacgctccg   420
aaatactgcc agtacctggc tcgtgaactg cagaaactgg gtgctacctt cgaacgtcgt   480
accgttacct ctctggaaca ggctttcgac ggtgctgacc tggttgttaa cgctaccggt   540
ctgggtgcta atctatcgc tggtatcgac gaccaggctg ctgaaccgat ccgtggtcag   600
accgttctgg ttaaatctcc gtgcaaacgt tgcaccatgg actcttctga cccggcttct   660
ccggcttaca tcatcccgcg tccgggtggt gaagttatct gcggtggtac ctacggtgtt   720
ggtgactggg acctgtctgt taacccggaa accgttcagc gtatcctgaa acactgcctg   780
cgtctggacc cgaccatctc ttctgacggt accatcgaag gtatcgaagt tctgcgtcac   840
aacgttggtc tgcgtccggc tctcgtggt ggtccgcgtg ttgaagctga acgtatcgtt   900
ctgccgctgg accgtaccaa atcccgctg tctctgggtc gtggttctgc tcgtgctgct   960
aaagaaaaag aagttaccct ggttcacgct tacggtttct cttctgctgg ttaccagcag  1020
tcttggggtg ctgctgaaga cgttgctcag ctggttgacg aagctttcca gcgttaccac  1080
ggtgctgctc gtgaatctaa actg                                         1104
```

<210> SEQ ID NO 98
<211> LENGTH: 368
<212> TYPE: PRT
<213> ORGANISM: Artificial Sequence
<220> FEATURE:
<223> OTHER INFORMATION: rtDAAO(C211L-M213T)

<400> SEQUENCE: 98

```
Met His Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Asn Trp Thr Pro Phe Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
    130                 135                 140
```

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
            165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Arg Leu Thr Thr Asp Ser Ser Asp Pro Ala Ser Pro Ala Tyr Ile
    210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
    290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365

<210> SEQ ID NO 99
<211> LENGTH: 1104
<212> TYPE: DNA
<213> ORGANISM: Artificial Sequence
<220> FEATURE:
<223> OTHER INFORMATION: rtDAAO(C211L-M213T)

<400> SEQUENCE: 99

```
atgcactctc agaaacgtgt tgttgttctg ggttctggtg ttatcggtct gtcttctgct      60
ctgatcctgg ctcgtaaagg ttactctgtt cacatcctgg ctcgtgacct gccggaagac     120
gtttcttctc agaccttcgc ttctccgtgg gctggtgcta actggacccc gttcatgacc     180
ctgaccgacg gtccgcgtca ggctaaatgg gaagaatcta ccttcaaaaa atgggttgaa     240
ctggttccga ccggtcacgc tatgtggctg aaaggtaccc gtcgtttcgc tcagaacgaa     300
gacggtctgc tgggtcactg gtacaaagac atcacccccga actaccgtcc gctgccgtct     360
tctgaatgcc cgccgggtgc tatcggtgtt acctacgaca ccctgtctgt tcacgctccg     420
aaatactgcc agtacctggc tcgtgaactg cagaaactgg gtgctacctt cgaacgtcgt     480
accgttacct ctctggaaca ggctttcgac ggtgctgacc tggttgttaa cgctaccggt     540
ctgggtgcta aatctatcgc tggtatcgac gaccaggctg ctgaaccgat ccgtggtcag     600
accgttctgg ttaaatctcc gtgcaaacgt ctgaccaccg actcttctga cccggcttct     660
ccggcttaca tcatcccgcg tccgggtggt gaagttatct gcggtggtac ctacggtgtt     720
ggtgactggg acctgtctgt taacccggaa accgttcagc gtatcctgaa acactgcctg     780
cgtctggacc cgaccatctc ttctgacggt accatcgaag gtatcgaagt tctgcgtcac     840
```

```
aacgttggtc tgcgtccggc tcgtcgtggt ggtccgcgtg ttgaagctga acgtatcgtt    900
ctgccgctgg accgtaccaa atctccgctg tctctgggtc gtggttctgc tcgtgctgct    960
aaagaaaaag aagttaccct ggttcacgct tacggtttct cttctgctgg ttaccagcag   1020
tcttggggtg ctgctgaaga cgttgctcag ctggttgacg aagctttcca gcgttaccac   1080
ggtgctgctc gtgaatctaa actg                                          1104
```

<210> SEQ ID NO 100
<211> LENGTH: 368
<212> TYPE: PRT
<213> ORGANISM: Artificial Sequence
<220> FEATURE:
<223> OTHER INFORMATION: rtDAAO(N54A-F58H-C211L-M213T)

<400> SEQUENCE: 100

```
Met His Ser Gln Lys Arg Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Ala Trp Thr Pro His Met Thr Leu Thr Asp Gly
    50                  55                  60

Pro Arg Gln Ala Lys Trp Glu Glu Ser Thr Phe Lys Lys Trp Val Glu
65                  70                  75                  80

Leu Val Pro Thr Gly His Ala Met Trp Leu Lys Gly Thr Arg Arg Phe
                85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
    130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Arg Leu Thr Thr Asp Ser Ser Asp Pro Ala Ser Pro Ala Tyr Ile
    210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
    290                 295                 300

Arg Thr Lys Ser Pro Leu Ser Leu Gly Arg Gly Ser Ala Arg Ala Ala
```

```
                305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
                340                 345                 350

Asp Glu Ala Phe Gln Arg Tyr His Gly Ala Ala Arg Glu Ser Lys Leu
            355                 360                 365

<210> SEQ ID NO 101
<211> LENGTH: 1104
<212> TYPE: DNA
<213> ORGANISM: Artificial Sequence
<220> FEATURE:
<223> OTHER INFORMATION: rtDAAO(N54A-F58H-C211L-M213T)

<400> SEQUENCE: 101
atgcactctc agaaacgtgt tgttgttctg ggttctggtg ttatcggtct gtcttctgct     60
ctgatcctgg ctcgtaaagg ttactctgtt cacatcctgg ctcgtgacct gccggaagac    120
gtttcttctc agaccttcgc ttctccgtgg gctggtgctg cttggacccc gcacatgacc    180
ctgaccgacg gtccgcgtca ggctaaatgg aagaatcta ccttcaaaaa atgggttgaa     240
ctggttccga ccggtcacgc tatgtggctg aaaggtaccc gtcgtttcgc tcagaacgaa    300
gacggtctgc tggtcactg gtacaaagac atcaccccga actaccgtcc gctgccgtct    360
tctgaatgcc gccgggtgc tatcggtgtt acctacgaca ccctgtctgt tcacgctccg    420
aaatactgcc agtacctggc tcgtgaactg cagaaactgg gtgctacctt cgaacgtcgt    480
accgttacct ctctggaaca ggctttcgac ggtgctgacc tggttgttaa cgctaccggt    540
ctgggtgcta atctatcgc tggtatcgac gaccaggctg ctgaaccgat ccgtggtcag    600
accgttctgg ttaaatctcc gtgcaaacgt ctgaccaccg actcttctga cccggcttct    660
ccggcttaca tcatcccgcg tccgggtggt gaagttatct gcggtggtac ctacggtgtt    720
ggtgactggg acctgtctgt taacccggaa accgttcagc gtatcctgaa acactgcctg    780
cgtctggacc cgaccatctc ttctgacggt accatcgaag gtatcgaagt tctgcgtcac    840
aacgttggtc tgcgtccggc tcgtcgtggt ggtccgcgtg ttgaagctga acgtatcgtt    900
ctgccgctgg accgtaccaa atctccgctg tctctgggtc gtggttctgc tcgtgctgct    960
aaagaaaaag aagttaccct ggttcacgct tacggtttct cttctgctgg ttaccagcag   1020
tcttggggtg ctgctgaaga cgttgctcag ctggttgacg aagctttcca gcgttaccac   1080
ggtgctgctc gtgaatctaa actg                                           1104

<210> SEQ ID NO 102
<211> LENGTH: 368
<212> TYPE: PRT
<213> ORGANISM: Artificial Sequence
<220> FEATURE:
<223> OTHER INFORMATION: rtDAAO(N54A-T56N-F58H-C211L-M213T)

<400> SEQUENCE: 102

Met His Ser Gln Lys Arg Val Val Val Leu Gly Ser Gly Val Ile Gly
1               5                   10                  15

Leu Ser Ser Ala Leu Ile Leu Ala Arg Lys Gly Tyr Ser Val His Ile
            20                  25                  30

Leu Ala Arg Asp Leu Pro Glu Asp Val Ser Ser Gln Thr Phe Ala Ser
        35                  40                  45

Pro Trp Ala Gly Ala Ala Trp Asn Pro His Met Thr Leu Thr Asp Gly
```

```
            50                  55                  60
Pro Arg Gln Ala Lys Trp Glu Glu Ser Thr Phe Lys Lys Trp Val Glu
 65                  70                  75                  80

Leu Val Pro Thr Gly His Ala Met Trp Leu Lys Gly Thr Arg Arg Phe
                 85                  90                  95

Ala Gln Asn Glu Asp Gly Leu Leu Gly His Trp Tyr Lys Asp Ile Thr
            100                 105                 110

Pro Asn Tyr Arg Pro Leu Pro Ser Ser Glu Cys Pro Pro Gly Ala Ile
        115                 120                 125

Gly Val Thr Tyr Asp Thr Leu Ser Val His Ala Pro Lys Tyr Cys Gln
130                 135                 140

Tyr Leu Ala Arg Glu Leu Gln Lys Leu Gly Ala Thr Phe Glu Arg Arg
145                 150                 155                 160

Thr Val Thr Ser Leu Glu Gln Ala Phe Asp Gly Ala Asp Leu Val Val
                165                 170                 175

Asn Ala Thr Gly Leu Gly Ala Lys Ser Ile Ala Gly Ile Asp Asp Gln
            180                 185                 190

Ala Ala Glu Pro Ile Arg Gly Gln Thr Val Leu Val Lys Ser Pro Cys
        195                 200                 205

Lys Arg Leu Thr Thr Asp Ser Ser Asp Pro Ala Ser Pro Ala Tyr Ile
210                 215                 220

Ile Pro Arg Pro Gly Gly Glu Val Ile Cys Gly Gly Thr Tyr Gly Val
225                 230                 235                 240

Gly Asp Trp Asp Leu Ser Val Asn Pro Glu Thr Val Gln Arg Ile Leu
                245                 250                 255

Lys His Cys Leu Arg Leu Asp Pro Thr Ile Ser Ser Asp Gly Thr Ile
            260                 265                 270

Glu Gly Ile Glu Val Leu Arg His Asn Val Gly Leu Arg Pro Ala Arg
        275                 280                 285

Arg Gly Gly Pro Arg Val Glu Ala Glu Arg Ile Val Leu Pro Leu Asp
290                 295                 300

Arg Thr Lys Ser Pro Leu Ser Leu Gly Arg Gly Ser Ala Arg Ala Ala
305                 310                 315                 320

Lys Glu Lys Glu Val Thr Leu Val His Ala Tyr Gly Phe Ser Ser Ala
                325                 330                 335

Gly Tyr Gln Gln Ser Trp Gly Ala Ala Glu Asp Val Ala Gln Leu Val
            340                 345                 350

Asp Glu Ala Phe Gln Arg Tyr His Gly Ala Ala Arg Glu Ser Lys Leu
        355                 360                 365

<210> SEQ ID NO 103
<211> LENGTH: 1104
<212> TYPE: DNA
<213> ORGANISM: Artificial Sequence
<220> FEATURE:
<223> OTHER INFORMATION: rtDAAO(N54A-T56N-F58H-C211L-M213T)

<400> SEQUENCE: 103
atgcactctc agaaacgtgt tgttgttctg ggttctggtg ttatcggtct gtcttctgct    60
ctgatcctgg ctcgtaaagg ttactctgtt cacatcctgg ctcgtgacct gccggaagac   120
gtttcttctc agaccttcgc ttctccgtgg gctggtgctg cttggaaccc gcacatgacc   180
ctgaccgacg tccgcgtca ggctaaatgg gaagaatcta ccttcaaaaa atgggttgaa   240
ctggttccga ccggtcacgc tatgtggctg aaaggtaccc gtcgtttcgc tcagaacgaa   300
```

```
gacggtctgc tgggtcactg gtacaaagac atcaccccga actaccgtcc gctgccgtct    360
tctgaatgcc cgccgggtgc tatcggtgtt acctacgaca ccctgtctgt tcacgctccg    420
aaatactgcc agtacctggc tcgtgaactg cagaaactgg gtgctacctt cgaacgtcgt    480
accgttacct ctctggaaca ggctttcgac ggtgctgacc tggttgttaa cgctaccggt    540
ctgggtgcta atctatcgc tggtatcgac gaccaggctg ctgaaccgat ccgtggtcag    600
accgttctgg ttaaatctcc gtgcaaacgt ctgaccaccg actcttctga cccggcttct    660
ccggcttaca tcatcccgcg tccgggtggt gaagttatct gcggtggtac ctacggtgtt    720
ggtgactggg acctgtctgt taacccggaa accgttcagc gtatcctgaa acactgcctg    780
cgtctggacc cgaccatctc ttctgacggt accatcgaag gtatcgaagt tctgcgtcac    840
aacgttggtc tgcgtccggc tcgtcgtggt ggtccgcgtg ttgaagctga acgtatcgtt    900
ctgccgctgg accgtaccaa atctccgctg tctctgggtc gtggttctgc tcgtgctgct    960
aaagaaaaag aagttaccct ggttcacgct tacggtttct cttctgctgg ttaccagcag   1020
tcttggggtg ctgctgaaga cgttgctcag ctggttgacg aagctttcca gcgttaccac   1080
ggtgctgctc gtgaatctaa actg                                           1104
```

```
<210> SEQ ID NO 104
<211> LENGTH: 39
<212> TYPE: DNA
<213> ORGANISM: Artificial Sequence
<220> FEATURE:
<223> OTHER INFORMATION: forward primer sequence for the construction of
      mutant libraries with mutations at positions 211 and 213 of the
      mutated D-amino acid oxidase sequence (N54V, F58Q)
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (18)..(18)
<223> OTHER INFORMATION: k is g or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t

<400> SEQUENCE: 104
agcaactgta aacgcnnkac cnnkgacagt agtgacccg                            39
```

```
<210> SEQ ID NO 105
<211> LENGTH: 39
<212> TYPE: DNA
<213> ORGANISM: Artificial Sequence
<220> FEATURE:
<223> OTHER INFORMATION: reverse primer sequence for the construction of
      mutant libraries with mutations at positions 211 and 213 of the
      mutated D-amino acid oxidase sequence (N54V, F58Q)
<220> FEATURE:
<221> NAME/KEY: misc_feature
<222> LOCATION: (16)..(16)
<223> OTHER INFORMATION: m is a or c
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (22)..(22)
<223> OTHER INFORMATION: m is a or c
```

```
<220> FEATURE:
<221> NAME/KEY: misc_feature
<222> LOCATION: (23)..(24)
<223> OTHER INFORMATION: n is a, c, g, or t

<400> SEQUENCE: 105
cgggtcacta ctgtcmnngg tmnngcgttt acagttgct                            39

<210> SEQ ID NO 106
<211> LENGTH: 45
<212> TYPE: DNA
<213> ORGANISM: Artificial Sequence
<220> FEATURE:
<223> OTHER INFORMATION: forward primer sequence for the construction of
      mutant library with mutations at positions 54, 56 and 58 of DAAO
      oxidase mutant 11
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (18)..(18)
<223> OTHER INFORMATION: k is g or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (24)..(24)
<223> OTHER INFORMATION: k is g or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (30)..(30)
<223> OTHER INFORMATION: k is g or t

<400> SEQUENCE: 106
cccttgggcc ggtgcnnktt gnnkcccnnk gatgagcaaa gaagc                     45

<210> SEQ ID NO 107
<211> LENGTH: 45
<212> TYPE: DNA
<213> ORGANISM: Artificial Sequence
<220> FEATURE:
<223> OTHER INFORMATION: reverse primer sequence for the construction of
      mutant library with mutations at positions 54, 56 and 58 of DAAO
      oxidase mutant 11
<220> FEATURE:
<221> NAME/KEY: misc_feature
<222> LOCATION: (16)..(16)
<223> OTHER INFORMATION: m is a or c
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (22)..(22)
<223> OTHER INFORMATION: m is a or c
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (28)..(28)
<223> OTHER INFORMATION: m is a or c
<220> FEATURE:
<221> NAME/KEY: misc_feature
<222> LOCATION: (29)..(30)
```

```
<223> OTHER INFORMATION: n is a, c, g, or t

<400> SEQUENCE: 107
gcttctttgc tcatcmnngg gmnncaamnn gcaccggccc aaggg                45
```